(12) United States Patent
Kakinuma et al.

(10) Patent No.: US 7,973,012 B2
(45) Date of Patent: Jul. 5, 2011

(54) C-PHENYL GLYCITOL COMPOUND

(75) Inventors: Hiroyuki Kakinuma, Tokyo (JP); Yohei Kobashi, Tokyo (JP); Yuko Hashimoto, Tokyo (JP); Takahiro Oi, Toyko (JP); Hitomi Takahashi, Tokyo (JP); Hideaki Amada, Toshima-ku (JP); Yuki Iwata, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 262 days.

(21) Appl. No.: 12/301,463

(22) PCT Filed: May 18, 2007

(86) PCT No.: PCT/JP2007/060653
§ 371 (c)(1),
(2), (4) Date: Nov. 18, 2008

(87) PCT Pub. No.: WO2007/136116
PCT Pub. Date: Nov. 29, 2007

(65) Prior Publication Data
US 2010/0022460 A1      Jan. 28, 2010

(30) Foreign Application Priority Data

May 19, 2006 (JP) .................. 2006-139891
Jul. 21, 2006 (JP) .................. 2006-200033

(51) Int. Cl.
*A01N 43/04* (2006.01)
*A61K 31/70* (2006.01)
*C07H 1/00* (2006.01)
*C07H 5/04* (2006.01)

(52) U.S. Cl. .................. 514/23; 536/18.7; 536/29.2

(58) Field of Classification Search .................. None
See application file for complete search history.

(56) References Cited

U.S. PATENT DOCUMENTS

| | | | |
|---|---|---|---|
| 6,414,126 B1 * | 7/2002 | Ellsworth et al. | 536/17.2 |
| 6,683,056 B2 * | 1/2004 | Washburn et al. | 514/25 |
| 7,217,697 B2 | 5/2007 | Shiohara et al. | |
| 2004/0176308 A1 | 9/2004 | Shiohara et al. | |
| 2005/0272669 A1 | 12/2005 | Fushimi et al. | |
| 2006/0035844 A1 | 2/2006 | Ito et al. | |
| 2007/0197623 A1 | 8/2007 | Brummerhop et al. | |

FOREIGN PATENT DOCUMENTS

| | | |
|---|---|---|
| CA | 2557801 A1 | 10/2005 |
| EP | 0850948 A1 | 7/1998 |
| EP | 1270584 A1 | 1/2003 |
| EP | 1544208 A1 | 6/2005 |
| WO | 98/31697 A1 | 7/1998 |
| WO | 01/27128 A1 | 4/2001 |
| WO | 01/68660 A1 | 9/2001 |
| WO | 02/098893 A1 | 12/2002 |
| WO | 2004/014932 A1 | 2/2004 |
| WO | 2004/018491 A1 | 3/2004 |
| WO | 2004/019958 A1 | 3/2004 |
| WO | 2004/050122 A1 | 6/2004 |
| WO | 2005/092877 A1 | 10/2005 |
| WO | 2005/121161 A1 | 12/2005 |

OTHER PUBLICATIONS

Byrn et al. Solid-State Chemistry of Drugs, 2d, Chapter 11 Hydrates and Solvates, 233-247,1999.*
Morissette et al. Adv. Drug Delivery Rev. 2004, 56, 275-300.*
Adachi et al., Metabolism, vol. 49, No. 8, Aug. 2000, pp. 990-995.*
Tomoichiro Asano, et al., "Glucose Transporter and Na+/glucose Cotransporter as Molecular Targets of Anti-Diabetic Drugs", Current Medicinal Chemistry, vol. 11, pp. 2717-2724, 2004.

* cited by examiner

*Primary Examiner* — Travis C McIntosh, III
(74) *Attorney, Agent, or Firm* — Sughrue Mion, PLLC

(57) ABSTRACT

Provided is a novel C-phenyl glycitol compound that may serve as a prophylactic or therapeutic agent for diabetes by inhibiting both SGLT1 activity and SGLT2 activity, thereby exhibiting a glucose absorption suppression action and a urine glucose excretion action. A C-phenyl glycitol compound represented by Formula (I) below or a pharmaceutically acceptable salt thereof or a hydrate thereof

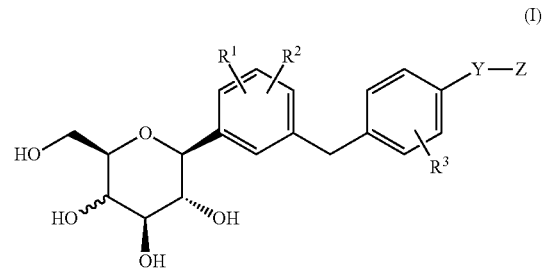

(I)

wherein $R^1$ and $R^2$ are the same or different and represent a hydrogen atom, a hydroxyl group, a $C_{1-6}$ alkyl group, a $C_{1-6}$ alkoxy group or a halogen atom,
$R^3$ is a hydrogen atom, a $C_{1-6}$ alkyl group, a $C_{1-6}$ alkoxy group or a halogen atom,
Y is a $C_{1-6}$ alkylene group, —O—$(CH_2)$n- (n is an integer of 1 to 4) or a $C_{2-6}$ alkenylene group, provided that when Z is —NHC(=NH)$NH_2$ or —NHCON($R^B$)$R^C$, n is not 1,
Z is —CONH$R^A$, —NHC(=NH)$NH_2$ or —NHCON($R^B$)$R^C$,

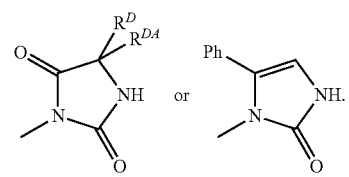

19 Claims, No Drawings

C-PHENYL GLYCITOL COMPOUND

TECHNICAL FIELD

The present invention relates to a C-phenyl glycitol compound having an inhibitory activity for a sodium dependent glucose cotransporter 1 (SGLT1) and a sodium dependent glucose cotransporter 2 (SGLT2).

BACKGROUND ART

When a person suffers from diabetes, the fasting blood glucose level exhibits 126 mg/dL or more. Even though the fasting blood glucose level falls within a normal range, there is a person exhibiting a postprandial blood glucose level as high as 140 to 200 mg/dL. Such a person is diagnosed as impaired glucose tolerance (hereinafter referred to as "IGT"). It has been considered that the risk of a cardiovascular disorder can be reduced by delaying onset of diabetes from IGT, and several supportive findings for this have been obtained. For example, the Da Qing IGT and Diabetes Study carried out in China in 1997 has reported that progression of IGT into Type II diabetes is significantly suppressed by diet and exercise (see Pan X R, et al., Diabets Care, vol 20, p. 534, 1997). As cases where medication is effective, when an α-glucosidase inhibitor, acarbose, which inhibits a hydrolysis of an oligosaccharide to delay glucose absorption from the small intestine, is administered, development of Type II diabetes from IGT is suppressed and further onset of hypertension is significantly suppressed. This is reported in the document (J.-L. Chiasson, et al., Lancent, vol. 359, p. 2072, 2002).

From the above, to suppress the onset of diabetes, it is important to control IGT by diet therapy, exercise therapy and medication.

Nevertheless, when a person suffers from diabetes, it comes to be necessary to control the blood glucose level at all times. Diabetes is basically treated by diet therapy and exercise therapy; however, when sufficient effect is not obtained by these therapies, medicament must be chosen.

On the small intestine epithelium of a mammal, a sodium dependent glucose cotransporter 1 (SGLT1) is expressed at a high frequency. It is known that SGLT1 serves depending upon sodium and plays a role in active transportation of glucose or galactose in the small intestine. Therefore, if glucose taken from a meal can be suppressed, IGT may be prevented or treated. Based on the concept, a pyrazole derivative inhibiting the activity of SGLT1 has been reported (see International Publication WO2002/098893, 2004/014932, 2004/018491, 2004/019958, 2005/121161 and 2004/050122).

Furthermore, a sodium dependent glucose cotransporter 2 (SGLT2) is expressed at a high frequency in the kidney. Glucose once filtrated by the glomerulus is reabsorbed via SGLT2 (see E. M. Wright, Am. J. Physiol. Renal. Physiol., vol. 280, p. F10, 2001). When an SGLT2 inhibitor is administered to a diabetic rat, glucose excretion into urine is facilitated, promoting a hypoglycemic action. From this, an SGLT2-specific inhibitor has been considered as a target molecule serving as a therapeutic agent for diabetes (see G. Toggenburger, et al. Biochem. Biophys. Acta., vol. 688, p. 557, 1982). In these circumstances, studies have been conducted on an SGLT2 inhibitor and various types of O-aryl glycoside derivatives have been provided (see EP Patent Application Publication No. 0850948A1 and International Publication WO2001/068660).

Accordingly, if the SGLT1 and SGLT2 activities can be simultaneously inhibited, a novel type of therapeutic agent for diabetes can be provided, which has not only a high postprandial glucose level suppression action ascribed to SGLT1 inhibition but also a progressive hypoglycemic action ascribed to SGLT2 inhibition.

Up to now, a C-phenyl glycoside derivative having a selective inhibitory activity to SGLT2 has been reported (see International Publication WO 2001/027128); however, a C-phenyl glycoside derivative strongly inhibiting both of SGLT1 and SGLT2 has not yet been reported.

DISCLOSURE OF THE INVENTION

An object of the present invention is to provide a C-phenyl glycitol compound, which is expected as a novel-type pharmaceutical for treating diabetes, capable of inhibiting both of SGLT1 and SGLT2 activities, having not only a glucose absorption suppression action from the digestive tract but also a urine glucose excretion action.

The present inventors conducted intensive studies to solve the aforementioned object. As a result, they found that a C-phenyl glycitol compound, which is formed by introducing a specific side-chain to an end of an aglycone, has excellent inhibitory actions for SGLT1 and SGLT2 activities. Based on the finding, the present invention was accomplished.

The C-phenyl glycitol compound of the present invention (hereinafter, referred to as "the compound of the invention") will be explained below.

By virtue of the present invention, a novel C-phenyl glycitol compound capable of inhibiting both SGLT1 and SGLT 2 activities can be provided.

First embodiment (1 embodiment) of the present invention is directed to a C-phenyl glycitol compound of the following formula or a pharmaceutically acceptable salt thereof or a hydrate thereof:

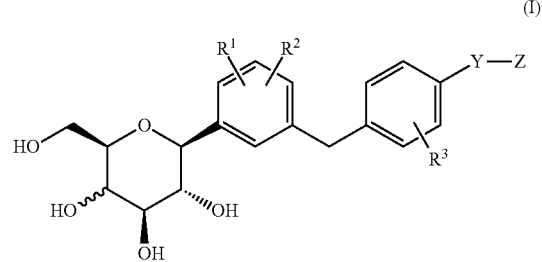

(I)

where
$R^1$ and $R^2$ are the same or different and represent a hydrogen atom, a hydroxyl group, a $C_{1-6}$ alkyl group, a $C_{1-6}$ alkoxy group or a halogen atom,
$R^3$ is a hydrogen atom, a $C_{1-6}$ alkyl group, a $C_{1-6}$ alkoxy group or a halogen atom,
Y is a $C_{1-6}$ alkylene group, —O—$(CH_2)$n- (n is an integer of 1 to 4) or a $C_{2-6}$ alkenylene group, provided that when Z is —NHC(=NH)$NH_2$ or —NHCON($R^B$)$R^C$, n is not 1,
Z is —CONH$R^A$, —NHC(=NH)$NH_2$ or —NHCON($R^B$)$R^C$,

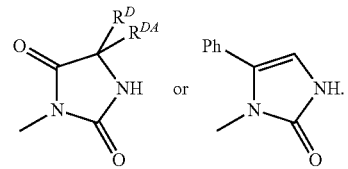

where
$R^A$ is
a $C_{1-6}$ alkyl group substituted with 1 to 3 substituents selected from the group consisting of a hydroxyl group, an amino group and a carbamoyl group,
$R^B$ is
(1) a hydrogen atom,
(2) a $C_{1-6}$ alkyl group that may be substituted with 1 to 3 substituents selected from Group A,
(3) a $C_{3-12}$ cycloalkyl group which may be substituted with 1 to 3 substituents selected from a hydroxyl group and a $C_{1-6}$ hydroxyalkyl group,
(4) a 3 to 12-membered heterocycloalkyl group or a 5 to 13-membered heteroaryl group that may be partially saturated, each of which contains one to three ring-constituting atom(s) selected from the group consisting of O, N, S, $SO_2$, CO and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group), and may be substituted with 1 to 3 substituents selected from the group consisting of a hydroxyl group and a $C_{1-6}$ hydroxyalkyl group, or
(5) a $C_{6-13}$ aryl group which may be partially saturated and may be substituted with 1 or 2 substituents selected from a hydroxyl group, and a $C_{1-6}$ alkyl group, a phenyl-$C_{1-6}$ alkyl group and a $C_{1-6}$ alkylsulfonyl group, each of which may be substituted with a hydroxyl group(s)
in which
Group A consists of
a halogen atom, a hydroxyl group, a $C_{1-6}$ alkoxy group which may be substituted with a hydroxyl group(s), a carboxyl group, a $C_{2-6}$ alkoxycarbonyl group, a carbamoyl group, an amino group, a $C_{1-6}$ alkylamino group, a di-$C_{1-6}$ alkylamino group, a $C_{2-6}$ acylamino group, a $C_{1-6}$ alkylthio group which may be substituted with a hydroxyl group(s),
a phenoxy group,
a phenyl group which may be substituted with 1 to 3 substituents selected from Group B (Group B consists of a hydroxyl group, a halogen atom, a $C_{1-6}$ alkoxy group, a $C_{1-6}$ alkyl group which may be substituted with a hydroxyl group(s), a $C_{1-6}$ alkylthio group, a thienyl group, a phenylthio group which may be substituted with a hydroxyl group(s) or a $C_{1-6}$ hydroxyalkyl group(s), and a piperidino group which may be substituted with a hydroxyl group(s) or a $C_{1-6}$ hydroxyalkyl group(s)),
a $C_{3-12}$ cycloalkyl group which may be substituted with 1 to 3 substituents selected from the group consisting of a hydroxyl group and a $C_{1-6}$ hydroxyalkyl group,
a 3 to 12-membered heterocycloalkyl group or a 5 to 13-membered heteroaryl group that may be partially saturated, each of which contains one to three ring-constituting atom(s) selected from the group consisting of O, N, S, $SO_2$, CO and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group), and may be substituted with 1 to 3 substituents selected from the group consisting of a hydroxyl group and a $C_{1-6}$ hydroxyalkyl group, and
—$CONR^{B1}R^{B2}$ wherein $R^{B1}$ and $R^{B2}$ together with the nitrogen atom to which they are attached form a 5 to 6 membered heterocycloalkyl group which may contain as another ring-constituting atom, an oxygen atom, a nitrogen atom or a sulfur atom and may be substituted with 1 or 2 substituents selected from the group consisting of a $C_{1-6}$ alkyl group which may be substituted with a hydroxyl group(s), a $C_{2-6}$ alkoxycarbonyl group and a phenyl$C_{1-6}$ alkyl group, $R^C$ is
a hydrogen atom, a $C_{1-6}$ alkyl group which may be substituted with 1 or 2 substituents selected from the group consisting of a hydroxyl group, a di-$C_{1-6}$ alkylamino group, a $C_{2-6}$ alkoxycarbonyl group and a $C_{1-6}$ alkoxy group, or a $C_{3-12}$ cycloalkyl group which may be substituted with a hydroxyl group(s), and
$R^B$ and $R^C$ together with the nitrogen atom to which they are attached may form a 3 to 12 membered heterocycloalkyl group or a 5 to 13 membered heteroaryl group that may be partially saturated, each of which may contain 1 or 2 ring-constituting atom selected from O, N, $NR^{11}$, S, $SO_2$ and CO and which may be substituted with 1 or 2 substituents selected from the group consisting of a hydroxyl group, a $C_{2-6}$ alkoxycarbonyl group, a carbamoyl group, a $C_{2-6}$ acyl ($C_{1-6}$ alkyl)amino group, a di-$C_{1-6}$ alkylaminocarbonyl group, a pyrrolidinyl group, a morpholino group, a pyrrolidin-1-yl-carbonyl group, a $C_{1-6}$ alkyl group that may be substituted with 1 to 3 substituents selected from the group consisting of a hydroxyl group, a pyrrolidin-1-yl group, a phenyl group and a $C_{2-6}$ alkoxycarbonyl group, and a phenyl group that may be substituted with 1 to 3 substituents selected from the group consisting of a $C_{1-6}$ alkyl group, a $C_{1-6}$ alkoxy group and a halogen atom
where $R^{11}$ is a hydrogen atom, a $C_{2-6}$ acyl group, a phenyl group that may be substituted with a hydroxyl group(s), a pyridyl group, a furylcarbonyl group, an oxolanylcarbonyl group, a $C_{2-6}$ alkoxycarbonyl group or a $C_{1-6}$ alkyl group that may be substituted with 1 or 2 substituents selected from the group consisting of a hydroxyl group, a phenyl group, a di-$C_{1-6}$ alkylamino group, a morpholino group and a pyrrolidin-1-yl-carbonyl group, and
$R^D$ is a hydrogen atom or a $C_{1-6}$ alkyl group which may be substituted with 1 or 2 substituents from the group consisting of a hydroxyl group, a $C_{3-12}$ cycloalkyl group, a phenyl group that may be substituted with a hydroxyl group(s), a pyridyl group, a $C_{2-6}$ alkoxycarbonyl group, an imidazolyl group and a 1-benzylimidazolyl group, and $R^{DA}$ is a hydrogen atom or a $C_{1-6}$ alkyl group.

BEST MODE FOR CARRYING OUT THE INVENTION

The present invention provide the following other embodiments 2 to 19:
2. The C-phenyl glycitol compound which is a C-phenyl glucitol compound represented by Formula (II) below or a pharmaceutically acceptable salt thereof, or a hydrate thereof,

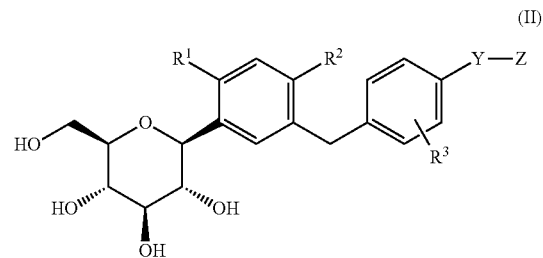

(II)

where $R^1$, $R^2$, $R^3$, Y and Z are the same as defined in Formula (I).
3. The C-phenyl glycitol compound or a pharmaceutically acceptable salt thereof, or a hydrate thereof in Formula (II), wherein $R^1$ is a hydrogen atom, a hydroxyl group, a $C_{1-4}$ alkyl group or a $C_{1-4}$ alkoxy group, and $R^2$ is a $C_{1-4}$ alkyl group or a halogen atom.

4. The C-phenyl glycitol compound according to the embodiment 2 or 3 or a pharmaceutically acceptable salt thereof, or a hydrate thereof, where $R^3$ is a hydrogen atom.

5. The C-phenyl glycitol compound or a pharmaceutically acceptable salt thereof, or a hydrate thereof according to embodiment 3 or 4, wherein Y is a $C_{1-6}$ alkylene group or —O—$(CH_2)$n- (n is an integer of 2 to 4), and Z is —NH-$CON(R^B)R^C$ wherein $R^B$ and $R^C$ are as defined in Formula (I).

6. The C-phenyl glycitol compound or a pharmaceutically acceptable salt thereof, or a hydrate thereof according to embodiment 3 or 4, wherein Y is a $C_{1-6}$ alkylene group or —O—$(CH_2)$n- (n is an integer of 2 to 4), and Z is —$NHCON(R^B)R^C$, where $R^B$ is (1) a $C_{1-6}$ alkyl group which may be substituted with 1 to 3 substituents selected from Group A, (2) a $C_{3-12}$ cycloalkyl group which may be substituted with 1 to 3 substituents selected from a hydroxyl group and a $C_{1-6}$ hydroxyalkyl group, (3) a 3 to 12-membered heterocycloalkyl group or a 5 to 13-membered heteroaryl group that may be partially saturated, each of which contains one to three ring-constituting atom(s) selected from the group consisting of O, N, S and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group) and may be substituted with 1 to 3 substituents selected from the group consisting of a hydroxyl group and a $C_{1-6}$ hydroxyalkyl group, or (4) a $C_{6-13}$ aryl group which may be partially saturated and may be substituted with 1 or 2 substituents selected from a hydroxyl group, and a $C_{1-6}$ alkyl group, a phenyl-$C_{1-6}$ alkyl group and a $C_{1-6}$ alkylsulfonyl group, each of which may be substituted with a hydroxyl group(s)

in which

Group A consists of a halogen atom, a hydroxyl group, a $C_{1-6}$ alkoxy group which may be substituted with a hydroxyl group(s), a $C_{2-6}$ alkoxycarbonyl group, a carbamoyl group, a di-$C_{1-6}$ alkylamino group, a $C_{1-6}$ alkylthio group which may be substituted with a hydroxyl group(s), a phenoxy group, a thienyl group, benzothienyl group, furyl group, a phenyl group which may be substituted with 1 to 3 substituents selected from the group consisting of a hydroxyl group, a halogen atom, a $C_{1-6}$ alkoxy group, a $C_{1-6}$ alkyl group which may be substituted with a hydroxyl group(s), a $C_{1-6}$ alkylthio group, a phenylthio group which may be substituted with a hydroxyl group(s) or a $C_{1-6}$ hydroxyalkyl group(s), and a piperidino group which may be substituted with a hydroxyl group(s) or a $C_{1-6}$ hydroxyalkyl group(s), a $C_{3-12}$ cycloalkyl group which may be substituted with 1 to 3 substituents selected from the group consisting of a hydroxyl group and a $C_{1-6}$ hydroxyalkyl group, a 3 to 12-membered heterocycloalkyl group which contains one to three ring-constituting atom(s) selected from the group consisting of O, N, S and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group) and may be substituted with 1 to 3 substituents selected from the group consisting of a hydroxyl group and a $C_{1-6}$ hydroxyalkyl group, and 4-$C_{1-6}$ alkylpiperadine-1-ylcarbonyl group, $R^C$ is a hydrogen atom, and $R^B$ and $R^C$ together with the nitrogen atom to which they are attached may form a piperidine group which may be substituted with a pyrrolidinyl group or a $C_{1-6}$ alkyl group which is substituted with a di$C_{1-6}$alkylamino group or a pyrrolidin-1-yl group, or a thiomorpholine group or a decahydroisoquinoline group.

7. The C-phenyl glycitol compound or a pharmaceutically acceptable salt thereof or a hydrate thereof according to any one of embodiments 2 to 4, wherein Y is a $C_{1-6}$ alkylene group, Z is —$CONHR^A$, where $R^A$ is a $C_{1-6}$ alkyl group substituted with 1 to 3 substituents selected from the group consisting of a hydroxyl group and a carbamoyl group.

8. The C-phenyl glycitol compound or a pharmaceutically acceptable salt thereof or a hydrate thereof according to any one of embodiments 2 to 4, wherein Y is a $C_{1-6}$ alkylene group, and Z is —NHC(=NH)$NH_2$.

9. The C-phenyl glycitol compound or a pharmaceutically acceptable salt thereof or a hydrate thereof according to any one of embodiments 2 to 4, wherein Y is a $C_{1-6}$ alkylene group, and Z is

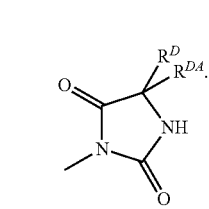

$R^D$ is a $C_{1-6}$ alkyl group which is substituted with a $C_{3-12}$ cycloalkyl group or a phenyl group and $R^{DA}$ is a hydrogen atom or a $C_{1-6}$ alkyl group.

10. The C-phenyl glycitol compound according to embodiment 1 which is a C-phenyl galacitol compound represented by Formula (III) below or a pharmaceutically acceptable salt thereof or a hydrate thereof,

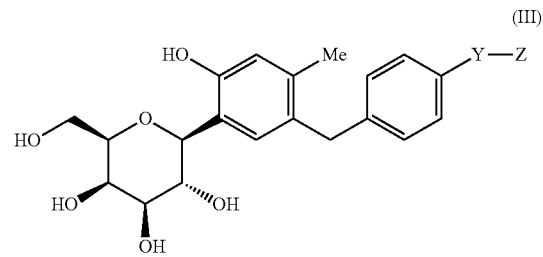

where

Y is a $C_{1-6}$ alkylene group, and

Z is

—$CONHR^A$, where $R^A$ is a $C_{1-6}$ alkyl group substituted with 1 to 3 substituents selected from the group consisting of a hydroxyl group and a carbamoyl group.

11. The C-phenyl glycitol compound according to embodiment 1 which is a C-phenyl glucitol compound represented by Formula (IV) below or a pharmaceutically acceptable salt thereof or a hydrate thereof,

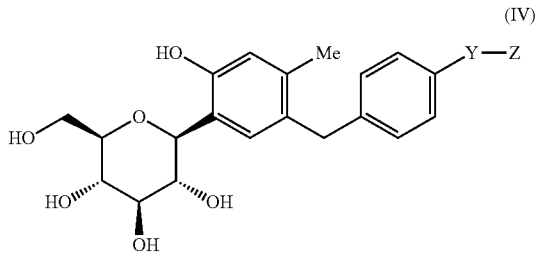

(IV)

where
Y is a $C_{1-6}$ alkylene group, and
Z is —$CONHR^{A1}$, —$NHC(=NH)NH_2$ or —$NHCOR^{B1}$,
where
$R^{A1}$ is a $C_{1-6}$ alkyl group substituted with 1 to 3 substituents selected from the group consisting of a hydroxyl group, an amino group and a carbamonyl group, and
$R^{B1}$ is
a $C_{1-6}$ alkylamino group which may be substituted with 1 to 3 hydroxyl groups or a 4-$C_{1-6}$ alkylpiperazin-1-yl-carbonyl group, or a 4-$C_{1-6}$ alkylpiperazin-1-yl group.

12. The C-phenyl glycitol compound according to embodiment 11 or a pharmaceutically acceptable salt thereof or a hydrate thereof, wherein,
Y is a $C_{1-6}$ alkylene group,
Z is —$CONHR^{A1}$ or —$NHC(=NH)NH_2$, or

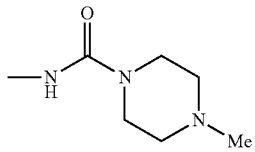

where
$R^{A1}$ is a $C_{1-6}$ alkyl group substituted with 1 to 3 substituents selected from the group consisting of a hydroxyl group, an amino group and a carbamonyl group.

13. The C-phenyl glycitol compound according to embodiment 11 or a pharmaceutically acceptable salt thereof or a hydrate thereof, wherein
Y is a $C_{1-6}$ alkylene group, and
Z is —$CONHR^{A1}$
where $R^{A1}$ is a $C_{1-6}$ alkyl group substituted with 1 to 3 substituents selected from the group consisting of a hydroxyl group, an amino group and a carbamonyl group.

14. The C-phenyl glycitol compound according to embodiment 11 or a pharmaceutically acceptable salt thereof or a hydrate thereof, wherein
Y is a $C_{1-6}$ alkylene group, and
Z is —$NHC(=NH)NH_2$.

15. The C-phenyl glycitol compound according to embodiment 11 or a pharmaceutically acceptable salt thereof or a hydrate thereof, wherein
Y is a $C_{1-6}$ alkylene group, and
Z is —$NHCOR^{B1}$ (where $R^{B1}$ is a $C_{1-6}$ alkylamino group substituted with 1 to 3 hydroxyl groups or a 4-$C_{1-6}$ alkylpiperazin-1-yl-carbonyl group, or a 4-$C_{1-6}$ alkylpiperazin-1-yl group).

16. The C-phenyl glycitol compound according to embodiment 11 or a pharmaceutically acceptable salt thereof or a hydrate thereof, wherein
Y is a $C_{1-6}$ alkylene group, and
Z is represented by

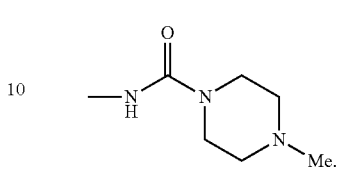

17. A pharmaceutical preparation, which comprises the C-phenyl glycitol compound according to any one of embodiments 1 to 16 or a pharmaceutically acceptable salt thereof or a hydrate thereof as an active ingredient.

18. The pharmaceutical preparation according to embodiment 17, which is an inhibitor of a sodium dependent glucose cotransporter 1 (SGLT1) activity and a sodium dependent glucose cotransporter 2 (SGLT2) activity.

19. The pharmaceutical preparation according to embodiment 17, which is a prophylactic or therapeutic agent for diabetes.

DETAILED DESCRIPTION OF THE PREFERRED EMBODIMENTS

The terms used in the present invention will be defined as follows.

The term of "a $C_{1-6}$ alkyl group" refers to a linear or branched alkyl group having 1 to 6 carbon atoms. Examples thereof may include a methyl group, an ethyl group, an n-propyl group, an isopropyl group, an n-butyl group, an isobutyl group, a tert-butyl group, a sec-butyl group, an n-pentyl group, a tert-pentyl group, an n-hexyl group and an isohexyl group.

The term of "a $C_{1-6}$ alkoxy group" refers to a linear or branched alkoxy group having 1 to 6 carbon atoms. Of them, a $C_{1-4}$ alkoxy group is preferable. Examples of the $C_{1-4}$ alkoxy group may include a methoxy group, an ethoxy group, a propoxy group, an isopropoxy group, an n-butoxy group, an isobutoxy group and a tert-butoxy group.

The term of "a halogen atom" refers to a fluorine atom, a chlorine atom, a bromine atom or an iodine atom.

The term of "a $C_{1-6}$ alkylene group" refers to a bivalent group formed by removing a hydrogen atom from a carbon atom of a $C_{1-6}$ alkyl group. Examples of the linear alkylene group may include a methylene group, an ethylene group, a trimethylene group, a tetramethylene group, a pentamethylene group and a hexamethylene group.

The term of "a $C_{2-6}$ alkenylene group" refers to a bivalent group formed by removing a hydrogen atom from a carbon atom of a $C_{2-6}$ alkenyl group. Examples of the linear alkenylene may include a vinylene (ethenylene) group, a propenylene group, a butenylene group, a pentenylene group and a hexenylene group.

The term of "a $C_{1-6}$ alkyl group substituted with 1 to 3 substituents selected from the group consisting of a hydroxyl group, an amino group and a carbamoyl group" refers to a linear or branched $C_{1-6}$ alkyl group in which 1 to 3 hydrogen atom(s) of a $C_{1-6}$ alkyl group is (are) replaced with at least one member selected from the group consisting of a hydroxyl group, an amino group and a carbamoyl group. Examples thereof may include a hydroxymethyl group, a hydroxyethyl group, a 2-hydroxy-1,1-dimethylethyl group, a 1,3-dihydroxy-2-methyl propan-2-yl group, a 1,3-dihydroxy-2-hydroxymethylpropan-2-yl group, a carbamoylmethyl group and a 2-carbamoylethyl group.

The term of "a $C_{3-12}$ cycloalkyl group" refers to a cyclic alkyl group having 3 to 12 carbon atoms and includes monocyclic, dicyclic and spiro-hydrocarbons. Examples of the monocyclic hydrocarbon may include a cyclopropyl group, a cyclobutyl group, a cyclopentyl group, a cyclohexyl group, a cycloheptyl group and a cyclooctyl group. Examples of the dicyclic hydrocarbon may include an adamantyl group, a bicyclo[2.2.1]heptyl group and a bicyclo[2.2.2]heptyl group. Examples of the spiro-hydrocarbon may include a spiro[3.4]octyl group and a spiro[4.5]decanyl group.

The term of "a 3 to 12-membered heterocycloalkyl group which contains one to three ring-constituting atom(s) selected from the group consisting of O, N, $NR^{10}$, S, $SO_2$ and CO" refers to the above-defined $C_{3-12}$ cycloalkyl group in which 1 to 3 methylene groups or methine groups are replaced with atom(s) selected from the group consisting of O, N, $NR^{10}$, S, $SO_2$ and CO. Examples thereof may include an oxanyl group, a 2-oxooxanyl group, a 1,3-dioxanyl group, a pyrrolidinyl group, a piperidino group, a 2-piperidyl group, a 4-piperidyl group, a piperazinyl group, a morpholino group, a thiomorpholino group, a quinuclidinyl group, a decahydroisoquinolinyl group, a decahydroquinolinyl group,

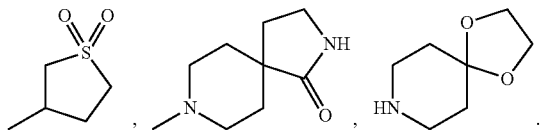

The term of "a 5 to 13-membered heteroaryl group that may be partially saturated which contains one to three ring-constituting atom(s) selected from group consisting of O, N, $NR^{10}$, S, $SO_2$ and CO" refers to a 5 to 13-membered unsaturated monocyclic, dicyclic or tricyclic heterocyclic ring, and may include a furyl group, an imidazolyl group, a thienyl group, a pyridyl group, a benzothienyl group, a 2,3-dihydrobenzofuranyl group, a 2,3-dihydro-1H-benzo[de]isoquinolinyl group, a 2,3-dihydro-1H-indolyl group, a 2,3-dihydro-1H-isoindolyl group and a 2,3,4,9-tetrahydro-1H-b-carbolynyl group.

The term of "a $C_{6-13}$ ary group which may be partially saturated" refers to an unsaturated monocyclic, dicyclic or tricyclic hydrocarbon ring having 6 to 13 carbon atoms. Examples thereof may include a phenyl group, a naphthyl group, a fluorenyl group, a 1,2,3,4-tetrahydronaphthyl group, an indanyl group.

The term of "a 5 to 6-membered heterocycloalkyl group which $R^{B1}$ and $R^{B2}$ together with the nitrogen atom to which they are attached form and which may contain as another ring-constituting atom, an oxygen atom, a nitrogen atom or a sulfur atom" may include a piperidino group, a piperazino group, a morpholino group, a thiomorpholino group.

The term of "a phenyl $C_{1-6}$ alkyl group" refers to a linear or branched $C_{1-6}$ alkyl group which is substituted with a phenyl group. Examples thereof may include a benzyl group and a phenylethyl group.

The term of "a $C_{2-6}$ alkoxycarbonyl group" has a structure composed of a linear or branched $C_{1-5}$ alkoxy group and a carbonyl group and is preferably a $C_{2-5}$ alkoxycarbonyl group. Examples thereof may include a methoxycarbonyl group, an ethoxycarbonyl group, a propoxycarbonyl group, an isopropoxycarbonyl group, an n-butoxycarbonyl group and a t-butoxycarbonyl group.

The term of "a $C_{1-6}$ alkylthio group" has a structure composed of a linear or branched $C_{1-6}$ alkyl group and a single thio group (—S—) and is preferably a $C_{1-4}$ alkylthio group. Examples of the $C_{1-6}$ alkylthio group include a methylthio group, an ethylthio group and a propylthio group.

The term of "a $C_{1-6}$ alkylamino group" has a structure composed of a linear or branched $C_{1-6}$ alkyl group and an amino group. Examples thereof may include a methylamino group and an ethylamino group.

The term of "a di-$C_{1-6}$ alkylamino group" has a structure composed of two linear or branched $C_{1-6}$ alkyl groups and an amino group. Examples thereof may include a dimethylamino group and a diethylamino group.

The term of "a $C_{2-6}$ acyl group" refers to a linear or branched aliphatic acyl group which contains 2 to 6 carbon atoms. Examples include an acetyl group, a propionyl group, a pivaloyl group, a butyryl group, an isobutyryl group and a valeryl group.

The term of "a $C_{2-6}$ acylamino group" has a structure composed of a $C_{2-6}$ acyl group and an amino group and is preferably an acetylamino group.

The term of "a $C_{2-6}$ acyl($C_{1-6}$ alkyl)amino group" has a structure composed of a $C_{2-6}$ acyl group, a $C_{1-6}$ alkyl group and an amino group.

The term of "a di-$C_{1-6}$ alkylaminocarbonyl group" has a structure composed of a di-$C_{1-6}$ alkylamino group and a carbonyl group.

The term of "a $C_{1-6}$ hydroxyalkyl group" refers to a $C_{1-6}$ alkyl group which is substituted with at least one hydroxyl group. Examples include a hydroxymethyl group, a 1-hydroxyethyl group, a 2-hydroxyethyl group, a 3-hydroxypentyl group and a 2-hydroxy-2-methylbutyl group.

The term of "3 to 12 membered heterocycloalkyl group or 5 to 13 membered heteroaryl group which $R^B$ and $R^C$ together with the nitrogen atom to which they are attached may form and each of which may contain 1 or 2 ring-constituting atom selected from O, N, $NR^{11}$, S, $SO_2$ and CO" refers to the 3 to 12 membered heterocycloalkyl group or 5 to 13 membered heteroaryl group as defined above.

The term of "a pharmaceutically acceptable salt" refers to a salt of an alkali metal, an alkaline earth metal, ammonium, alkyl ammonium, or a salt of a mineral acid or an organic acid. Examples thereof may include a sodium salt, a potassium salt, a calcium salt, an ammonium salt, an aluminum salt, a triethylammonium salt, an acetate salt, a propionate salt, a butyrate salt, a formate salt, a trifluoroacetate salt, a maleate salt, a tartrate salt, a citrate salt, a stearate salt, a succinate salt, an ethyl succinate salt, a lactobionate salt, a gluconate salt, a glucoheptonate salt, a benzoate salt, a methanesulfonate salt, an ethanesulfonate salt, a 2-hydroxyethanesulfonate salt, a benzenesulfonate salt, a p-toluenesulfonate salt, a lauryl sulfate salt, a malate salt, an aspartate salt, a glutamate salt, an adipate salt, a salt with cysteine, a salt with N-acetylcysteine, a hydrochloride salt, a hydrobromate salt, a phosphate salt, a sulfate salt, a hydroiodate salt, a nicotinate salt, an oxalate salt, a picrate salt, a thiocyanate salt, an undecanoate salt, a salt with an acrylate polymer and a salt with a carboxyvinyl polymer.

The term of "hydrate" refers to a pharmaceutically acceptable hydrate of the compound of the invention or a salt thereof. The compound of the invention or a salt thereof absorbs moisture when exposed to the air or recrystallized, with the result that it optionally has hygroscopic water or becomes a hydrate. Such a hydrate may be included in the hydrate in the present invention.

Some compounds of the invention and intermediates thereof which have a chiral center may be present in the form of a diastereomer or an enantiomer. Furthermore, some compounds of the invention and intermediates may be present as a keto-enol tautomer. Moreover, some compounds of the invention and intermediates thereof may be present as a geometric isomer (E, Z form). Therefore, isomers and mixtures thereof mentioned above are all included in the compound of the invention and an intermediate thereof.

In particular, in a compound represented by Formula (I), the steric configuration of the hydroxyl group at the 4-position of the glucose moiety is either an R-form or an S-form, which is indicated by a wavy line.

Preferable examples of the compound of the invention will be described below.

In Formula (I), preferable substitution positions of $R^1$ and $R^2$ are those as shown in Formula (II).

$R^1$ is preferably a hydrogen atom, a hydroxyl group, a $C_{1-4}$ alkyl group and a $C_{1-4}$ alkoxy group, more preferably, a hydroxyl group and a $C_{1-4}$ alkoxy group, and further preferably, a hydroxyl group and a methoxy group.

$R^2$ is preferably a hydroxyl group, a $C_{1-6}$ alkyl group and a halogen atom, more preferably, a $C_{1-4}$ alkyl group and a halogen atom, and further preferably, a methyl group and a chlorine atom.

In Formula (I) or (II), $R^3$ is preferably a hydrogen atom, a $C_{1-4}$ alkyl group and a halogen atom, more preferably, a hydrogen atom, a methyl group and a fluorine atom, and most preferably, a hydrogen atom. When $R^3$ is other than a hydrogen atom, a preferable substitution position is the ortho position relative to the benzyl moiety in Formula (I) or (II).

In Formula (I) or (II), Y may be preferably a $C_{1-4}$ alkylene group, —O—$(CH_2)_2$— or a $C_{2-4}$ alkenylene group, more preferably, a $C_{1-3}$ alkylene group, or —O—$(CH_2)_2$—, and further preferably, a $C_{1-3}$ alkylene group. When Z is —NH-CON($R^B$)$R^C$, Y is most preferably —$(CH_2)_2$—.

In Formula (I) or (II) where Z is —NHCON($R^B$)$R^C$, $R^B$ and $R^C$ are preferably the following (i) to (v) embodiments.

(i) $R^C$ is a hydrogen atom and $R^B$ is a $C_{1-6}$ alkyl group that may be substituted with 1, 2 or 3 substituents selected from Group A.

Group A herein is a halogen atom, a hydroxyl group, a $C_{1-6}$ alkoxy group which may be substituted with a hydroxyl group(s), a $C_{2-6}$ alkoxycarbonyl group, a carbamoyl group, a di-$C_{1-6}$ alkylamino group, a $C_{2-6}$ acylamino group, a $C_{1-6}$ alkylthio group which may be substituted with a hydroxyl group(s), a phenoxy group, a furyl group, a thienyl group, a benzothienyl group, a 2,3-dihydro-benzofuranyl group, a phenyl group that may be substituted with 1 to 3 substituents selected from Group B (Group B consists of a hydroxyl group, a halogen atom, a $C_{1-6}$ alkoxy group, a $C_{1-6}$ alkyl group which may be substituted with a hydroxyl group(s), a $C_{1-6}$ alkylthio group, a phenylthio group which may be substituted with a hydroxyl group(s) or a $C_{1-6}$ hydroxyalkyl group(s), and a piperidino group which may be substituted with a hydroxyl group(s) or a $C_{1-6}$ hydroxyalkyl group(s)), a $C_{3-12}$ cycloalkyl group which may be substituted with 1 to 3 substituents selected from the group consisting of a hydroxyl group and a $C_{1-6}$ hydroxyalkyl group, a 3 to 12-membered heterocycloalkyl group which contains one to three ring-constituting atom(s) selected from the group consisting of O, N, S and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group) and may be substituted with 1 to 3 substituents selected from the group consisting of a hydroxyl group and a $C_{1-6}$ hydroxyalkyl group, and 4-$C_{1-6}$ alkylpiperadine-1-ylcarbonyl group.

More preferable examples of Group A include a hydroxyl group, a methoxy group, an ethoxy group, a $C_{3-6}$ cycloalkyl group (a cyclopropyl group, a cyclobutyl group, a cyclopentyl group, a cyclohexyl group), which may be substituted with 1 to 3 substituents selected from the group consisting of a hydroxyl group and a $C_{1-6}$ hydroxyalkyl group, a methoxycarbonyl group, a carbamoyl group, a dimethylamino group, an acetylamino group, a methylthio group, a phenyl group, a 4-hydroxyphenyl group, a 4-methylthiophenyl group, a 3-methoxyphenyl group, a 3,4-dimethoxyphenyl group, a phenoxy group, a 2-(hydroxymethylphenylthio)phenyl group, a thienyl group, a furyl group, a benzothienyl group, a 2,3-dihydro-benzofuranyl group, a 4-methylpiperazin-1-yl carbonyl group, a 1-pyrrolidinyl group, a 1,3-dioxane-2-yl group, a 2-oxanyl group and a piperidino group.

(ii) $R^C$ is a hydrogen atom and $R^B$ is a $C_{3-12}$ cycloalkyl group that may be substituted with 1, 2 or 3 substituents selected from a hydroxyl group and a $C_{1-6}$ hydroxyalkyl group.

The $C_{3-12}$ cycloalkyl group herein is preferably a cyclopropyl group, a cyclobutyl group, a cyclopentyl group, a cyclohexyl group, a cycloheptyl, a cyclooctyl group, an adamantyl group, a bicyclo[2.2.1]heptyl group, a bicyclo[2.2.2]heptyl group, more preferably, a cyclopentyl group, a cyclohexyl group, a bicyclo[2.2.1]heptyl group or an adamantyl group.

(iii) $R^C$ is a hydrogen atom and $R^B$ is a "3 to 12-membered heterocycloalkyl group or a 5 to 13-membered heteroaryl group that may be partially saturated, each of which contains one to three ring-constituting atom(s) selected from the group consisting of O, N, S and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group)", preferably a pyrrolidinyl group, a piperidyl group and a quinuclidinyl group, more preferably, a pyrrolidinyl group, a 4-piperidyl group in which a nitrogen atom is substituted with a phenyl $C_{1-6}$ alkyl group or a $C_{2-6}$ alkoxycarbonyl group, and further preferably, a 3-(1-benzyl)pyrrolidinyl group, a 4-(1-benzyl)piperidyl group, or a 4-(1-ethoxycarbonyl)piperidyl group.

(iv) $R^C$ is a hydrogen atom and $R^B$ is a 6 to 13-membered aryl group which may be substituted with 1 or 2 substituents selected from a hydroxyl group, and a $C_{1-6}$ alkyl group, a phenyl-$C_{1-6}$ alkyl group and a $C_{1-6}$ alkylsulfonyl group, each of which may be substituted with a hydroxyl group(s) or a 6 to 13-membered aryl group which is partially saturated which may be substituted with 1 or 2 hydroxyl group(s). Herein the "6 to 13-membered aryl group" includes a phenyl group or a naphthyl group, and the "6 to 13-membered aryl group which is partially saturated" includes a fluorenyl group, a 1,2,3,4-tetrahydro-naphthyl group or an indanyl group.

Of them, a preferable $R^B$ is a phenyl group substituted with a phenyl-$C_{1-6}$ alkyl group, or a fluorenyl group, a 1,2,3,4-tetrahydro-naphthyl group or an indanyl group, each of which may be substituted with 1 or 2 hydroxyl group(s).

(v) As another preferable example, $R^B$ and $R^C$ together with the nitrogen atom to which they are attached form a 3 to 12 membered heterocycloalkyl group which may contain 1 or 2 ring-constituting atom selected from O, N, S and $NR^{11}$ ($R^{11}$ is a $C_{1-6}$ alkyl group that may be substituted with a di-$C_{1-6}$ alkylamino group), and which may be substituted with 1 or 2 substituents selected from a pyrrolidinyl group and a $C_{1-6}$ alkyl group that may be substituted with a substituent selected from the group consisting of a hydroxyl group and a pyrrolidin-1-yl group.

Examples of the (v) embodiment include a piperidino group, a 4-methylpiperidino group, a 2-decahydroisoquinolinyl group, a thiomorpholino group, a 4-[2-(pyrrolidin-1-yl)

ethyl]piperidino group, a 4-(pyrrolidin-1-yl)piperidino group, a 3-decahydroquinolinyl group, a 4-[2-(N,N-dimethylamino)ethyl]piperazin-1-yl group and a 3-hydroxymethylpiperidino group.

In Formula (I) or (II) where Z is —CONHR$^A$, R$^A$ is preferably a $C_{1-6}$ alkyl group substituted with 1 to 3 substituents selected from the group consisting of a hydroxyl group and a carbamoyl group.

Processes for producing the compound (I) of the invention will be described below.

Production Process 1

The compound (I) of the invention where Y is a $C_{2-6}$ alkylene group or a $C_{2-6}$ alkenylene group and Z is —CONHR$^A$ can be synthesized by the following method.

(1) Step 1 (Heck Reaction)

A compound (IA) and olefin acetic acid (IB) are allowed to react in the presence of a palladium catalyst, a phosphine ligand and an appropriate base in accordance with the Heck reaction to synthesize a compound (IC). Examples of the palladium catalyst used herein may include palladium acetate, tetrakis(triphenylphosphine)palladium, dibenzylideneacetonepalladium, bis(triphenylphosphine)palladium chloride and palladium-activated carbon. Examples of the phosphine ligand may include triphenylphosphine and tris(2-methylphenyl)phosphine. Examples of the base include triethylamine, N,N-diisopropylethylamine, potassium carbonate, calcium carbonate, cesium carbonate and potassium t-butoxide. Examples of the solvent to be used in this reaction

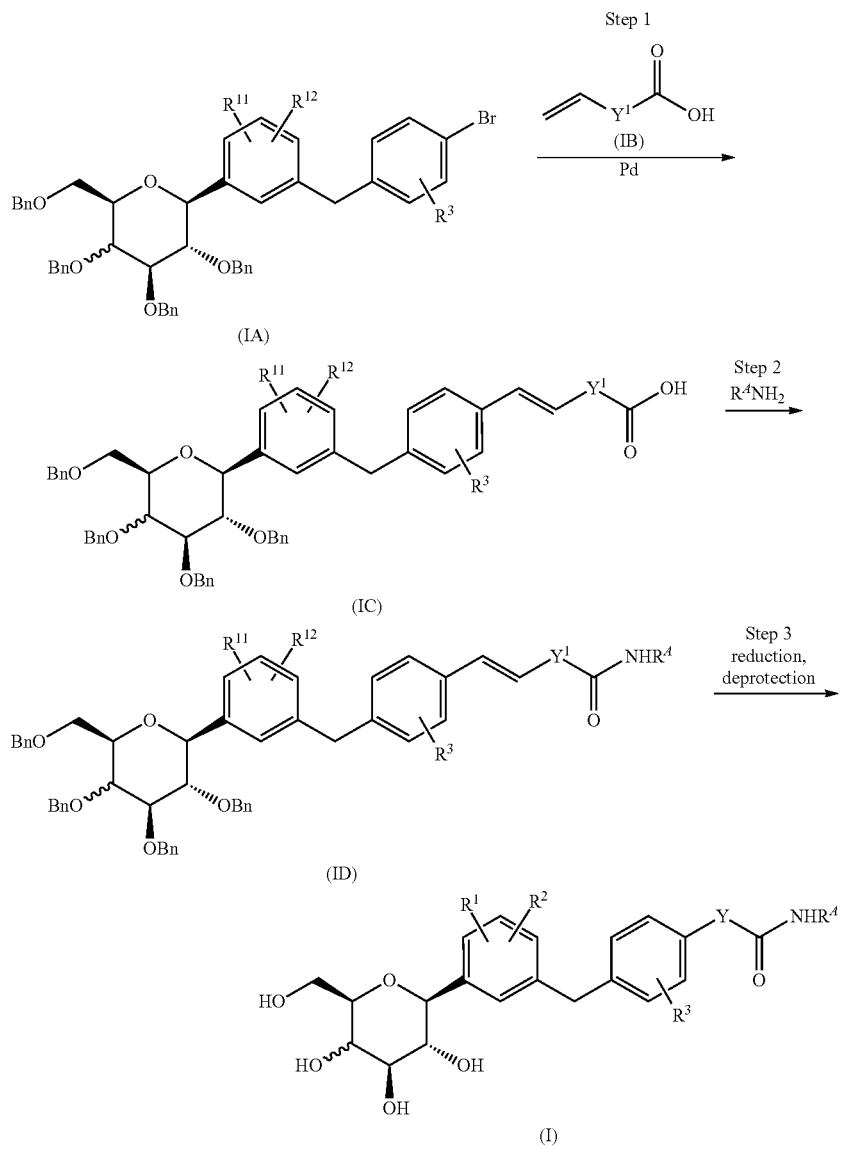

Note that, in the formula, R$^{11}$ and R$^{12}$ may be the same or different and represent a hydrogen atom, a benzyloxy group, a methoxymethoxy group, a ($C_{1-6}$ alkyl)$_3$SiO—, a $C_{1-6}$ alkyl group, a $C_{1-6}$ alkoxy group or halogen atom, Y$^1$ represents a single bond or a $C_{1-4}$ alkylene group, and other reference symbols are the same as defined above.

may include acetonitrile, toluene and tetrahydrofuran. The reaction temperature is from 0° C. to a reflux temperature; however, a microwave is optionally used.

(2) Step 2 (Conversion to Amide Group)

The compound (IC) is subjected to dehydration condensation with an amine (R$^A$NH$_2$) to obtain a compound (ID).

Preferable examples of the solvent to be used in this reaction include chloroform, dichloromethane and N,N-dimethylformamide. Preferable examples of the dehydration condensation agent include N,N'-dicyclohexylcarbodiimide (DCC), N-ethyl-N'-(3-dimethylaminopropyl) carbodiimide hydrochloride (WSC), 1,1'-carbonyldiimidazole (CDI) and WSC/1-hydroxybenzotriazol monohydrate. The reaction temperature herein is 0° C. to 60° C.

(3) Step 3 (Reduction and Deprotection)

Catalytic hydrogenation of the compound (ID) obtained above is performed by using a catalyst such as palladium activated carbon, palladium hydroxide or a platinum-palladium activated carbon under a hydrogen atmosphere. In this way, reduction of the olefin and debenzylation can be simultaneously performed to obtain the compound (I) of the invention. Of the catalysts mentioned above, palladium activated carbon or palladium hydroxide is preferable. Examples of the solvent to be used in this reaction may include methanol, ethanol, 2-propanol, ethyl acetate, acetic acid and solvent mixtures thereof. The reaction temperature is from room temperature to a reflux temperature; however, room temperature is preferable.

Alternatively, in the debenzylation, a Lewis acid such as $BF_3 \cdot Et_2O$, $BCl_3$, $BCl_3 \cdot Me_2S$, $BBr_3$, $AlCl_3$, $CF_3COOH$, or TfOH can be used. Examples of the solvent to be used in this reaction may include chloroform, dichloromethane, acetonitrile, diethyl ether, tetrahydrofuran, dimethylsulfide and anisole. Of them, it is preferable to use $CF_3COOH$, TfOH or ethanedithiol in dimethylsulfide. The reaction temperature is preferably −78° C. to 40° C.

Production Process 2

The compound (I) of the invention where Y is a $C_{2-6}$ alkylene group or a $C_{2-6}$ alkenylene group and Z is —NHC(=NH)NH$_2$ or —NHCON($R^B$)$R^C$ can be synthesized by the following method. Note that, in the formula, $Z^1$ represents a guanidino group protected with a benzyloxycarbonyl group or —NHCON($R^B$)$R^C$, and other reference symbols are the same as defined above.

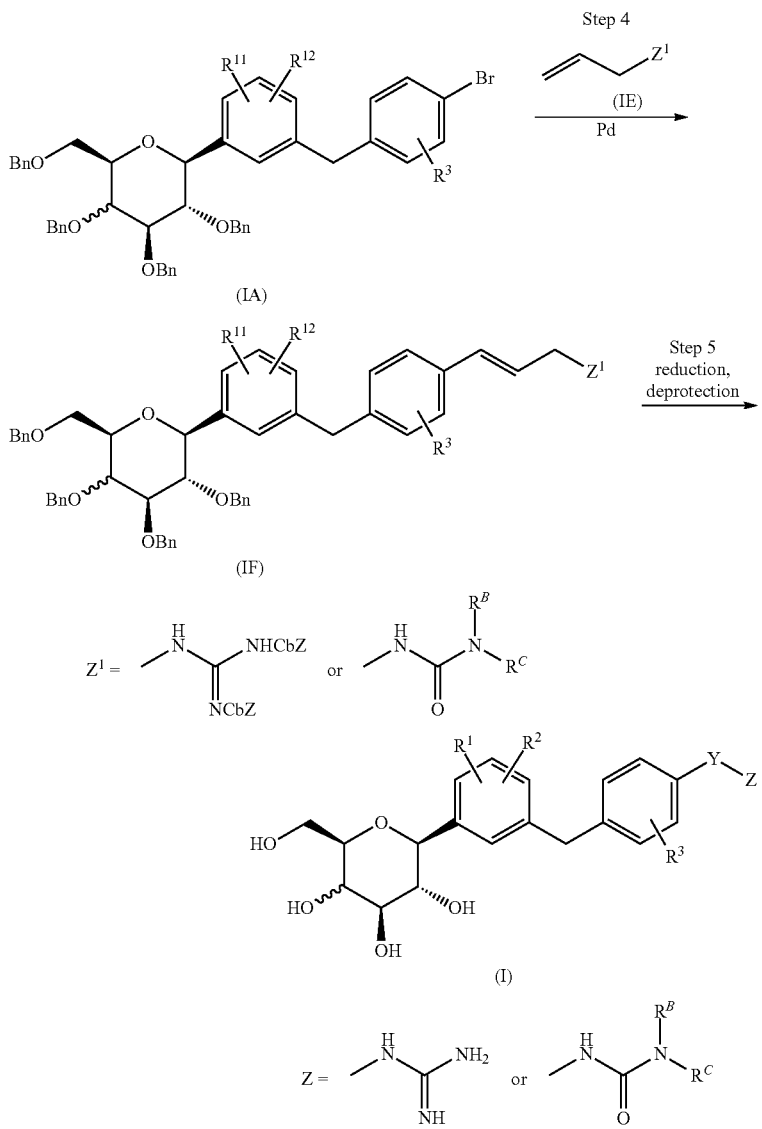

(4) Step 4 (Heck Reaction)

The Compound (IA) and an allylamine (IE) can be converted into a compound (IF) by the Heck reaction described in Step 1.

(5) Step 5 (Reduction and Deprotection)

The Compound (IF) obtained above is subjected to deprotection with catalytic hydrogenation or a Lewis acid as described in Step 3 to obtain the compound (I) of the invention where Z is a guanidino group or an ureido group.

Production Process 3

The compound (I) of the invention where Y is a single bond or a $C_{1-6}$ alkylene group and Z is —NHCON($R^B$)$R^C$ can be synthesized also by the following method.

Note that, in the formula, $R^{13}$ and $R^{14}$ may be the same or different and represent a hydrogen atom, a benzyloxy group, a $C_{1-6}$ alkyl group, $C_{1-6}$ alkoxy group or a halogen atom, $P^1$ represents a methoxymethyl group, tetrahydropyranyl group or a $(C_{1-6}$ alkyl$)_3$Si—, and other reference symbols are the same as defined above. The intermediate (IIB) or the intermediate (IIF) wherein Y is a single bond or a $C_{1-6}$ alkylene group can be also synthesized in the same manner as in Steps 34 to 36 below.

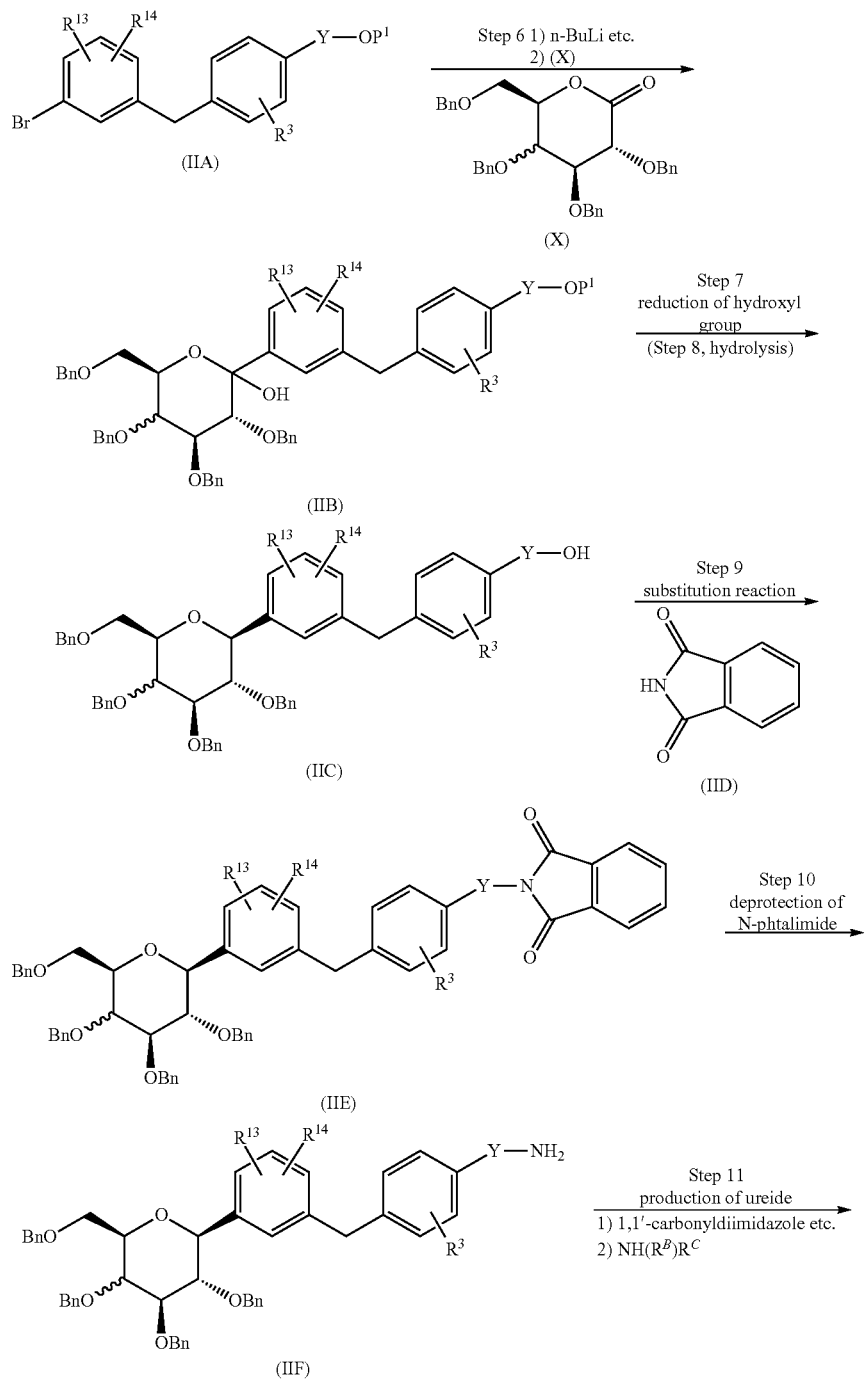

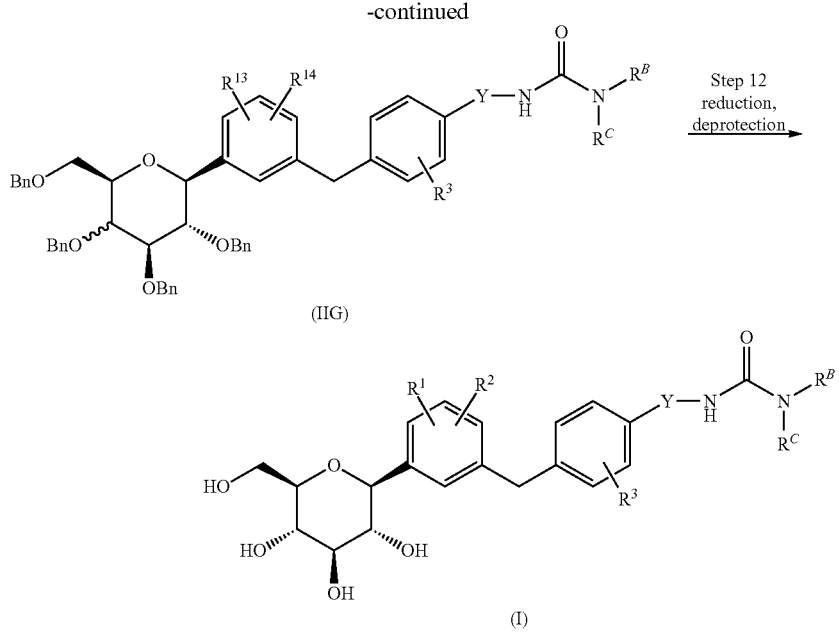

(6) Step 6

An aryllithium reagent can be prepared from an intermediate compound (IIA) (which can be synthesized in accordance with the disclosure of WO06/073197) by use of an organic metal reagent such as n-butyllithium, sec-butyllithium or tert-butyllithium. This is condensed with δ-lactone (X) to obtain a compound (IIB). Examples of the solvent to be used in this reaction may include tetrahydrofuran, diethyl ether and toluene. The reaction temperature is −80° C. to room temperature, and preferably, −78° C. to −25° C.

(7) Step 7 (Reduction of Hydroxyl Group)

The compound (IIB) and $Et_3SiH$, $i-Pr_3SiH$, $t-BuMe_2SiH$ or $Ph_2SiHCl$ are allowed to react in the presence of a Lewis acid to reduce a hydroxyl group. Examples of the Lewis acid to be used in this reaction may include $BF_3.Et_2O$, $CF_3COOH$, $InCl_3$, $TiCl_4$, TMSOTf, p-toluenesulfonic acid and methanesulfonic acid. Examples of the solvent include chloroform, dichloromethane, toluene, tetrahydrofuran, acetonitrile and solvent mixtures thereof, preferably, a solvent mixture containing acetonitrile such as acetonitrile/chloroform, acetonitrile/dichloromethane, acetonitrile/tetrahydrofuran and acetonitrile/tetrahydrofuran/toluene. The reaction temperature herein is −60° C. to 25° C., and preferably, −30° C. to 25° C.

In the reaction mentioned above, a protecting group $P^1$ is optionally removed depending upon the reaction temperature. In this case, a compound (IIC) from which $P^1$ is removed is optionally obtained.

(8) Step 8 (Hydrolysis)

Following Step 7, a protecting group $P^1$ can be removed by use of hydrochloric acid, sulfuric acid, p-toluenesulfonic acid monohydrate, pyridinium p-toluenesulfonate, hydrogen fluoride pyridine, $n-Bu_4NF$ or the like. Examples of the solvent to be used in this reaction may include methanol, ethanol, 2-propanol, chloroform, dichloromethane, toluene, tetrahydrofuran, acetonitrile, diisopropyl ether, water and solvent mixtures thereof. When $P^1$ is a methoxymethyl group, a preferable acid is hydrochloric acid and a preferable solvent is methanol, diisopropyl ether, toluene or tetrahydrofuran, and more preferably, a solvent mixture containing methanol such as methanol/toluene, methanol/diisopropyl ether or methanol/toluene/diisopropyl ether. The reaction temperature differs depending upon the solvent or acid to be used; however, it is 0° C. to 100° C., and preferably, 0° C. to 80° C.

(9) Step 9 (Substitution Reaction)

The compound (IIC) where Y is a $C_{1-6}$alkylene group and a reagent (IID) are condensed in the conditions of the Mitsunobu reaction (Org. Reactions, Vol. 42, p. 335) using an azo reagent and a phosphine to obtain the compound (IIE).

Examples of the phosphine that can be used in the Mitsunobu reaction may include triphenylphosphine, tri-n-butylphosphine, tri-t-butylphosphine, tritolylphosphine and diphenyl-2-pyridylphosphine. Of them, triphenylphosphine and diphenyl-2-pyridyl phosphine are preferable, and triphenylphosphine is more preferable. Examples of the azo reagent include diethyl azodicarboxylate, diisopropyl azodicarboxylate, di-tert-butyl azodicarboxylate, 1,1'-azobis(N,N-dimethylformamide) and 1,1'-(azodicarbonyl)dipiperidine. Of them, diethyl azodicarboxylate and diisopropyl azodicarboxylate are preferable. Examples of the solvent include tetrahydrofuran, dioxane, toluene, methylene chloride, chloroform, acetonitrile, ethyl acetate, dimethylsulfoxide and N,N-dimethylformamide, and preferably tetrahydrofuran and toluene. The reaction temperature is preferably from −20° C. to room temperature.

(10) Step 10 (Removing Phthalimide)

The compound (IIE) and a hydrazine hydrate or methylhydrazine are allowed to react in an appropriate solvent to obtain an amine (IIF). Preferable examples of the solvent used herein include methanol, ethanol, tetrahydrofuran, water and solvent mixtures thereof. The reaction temperature is from room temperature to 100° C., and preferably from room temperature to 60° C.

The obtained amine (IIF) can be purified by forming a salt with a mineral acid or an organic acid as mentioned above. Examples of the salt preferably used for purification include a hydrochloride, methanesulfonate, ethanesulfonate, 2-hydroxyethanesulfonate, benzenesulfonate and p-toluenesulfonate, and more preferably, benzenesulfonate.

(11) Step 11 (Formation of Urea)

The compound (IIF) can be synthesized with a carbonylation reagent and NH($R^B$)$R^C$ to synthesize a compound (IIG). Examples of the carbonylation reagent include 1,1'-carbonyldiimidazole, p-nitrophenylchloroformate and triphosgene. In this reaction, a base such as triethylamine, pyridine or N-methylmorpholine may be preferably used. Examples of the solvent to be used herein include chloroform, dichloromethane, tetrahydrofuran, N,N-dimethylformamide and dimethylsulfoxide. A mixture solvent thereof may be used. Preferable examples of the mixture solvent include chloroform/N,N-dimethylformamide, chloroform/dimethylsulfoxide and tetrahydrofuran/N,N-dimethylformamide. The reaction temperature is room temperature to 80° C. When the reaction rate is low, the temperature may be raised.

(12) Step 12 (Deprotection)

The compound (IIG) obtained above is subjected to deprotection with catalytic hydrogenation or a Lewis acid as described in Step 3 to obtain the compound (I) of the invention where Z is an ureido group.

Production Process 4

The compound (I) of the invention where Z is an ureido group can be synthesized after the hydroxyl group of the glucose moiety is protected with an acyl group such as an acetyl group.

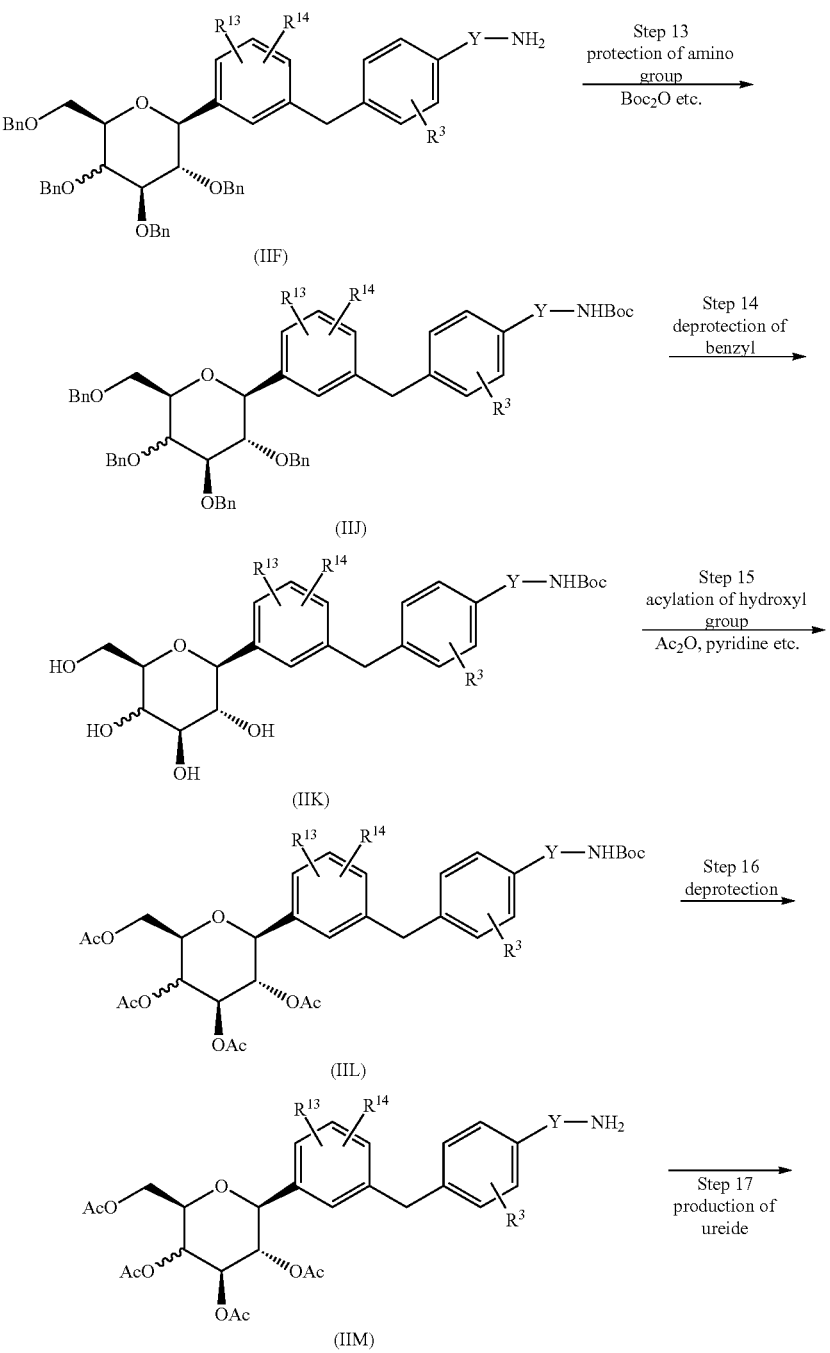

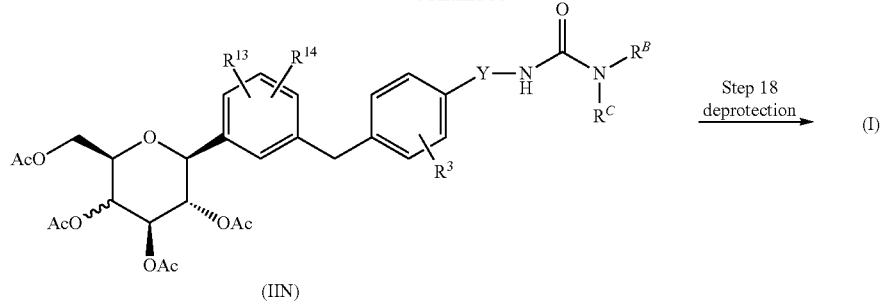

(IIN)

(13) Step 13 (Protection of Amino Group)

The amino group of a compound (IIF) is protected with a protecting group resistant to catalytic hydrogenation, for example, tert-butylcarbonate (Boc) or 9-fluolenylmethylcarbonate (Fmoc). The compound (IIF), (Boc)$_2$O and Fmoc-Cl are allowed to react in a solvent such as chloroform, dichloromethane, tetrahydrofuran or dioxane in the presence of an appropriate base to obtain a compound (IIJ). Preferable examples of the base include sodium carbonate, sodium hydrogen carbonate, potassium carbonate, potassium hydroxide, sodium hydride, pyridine and triethylamine.

(14) Step 14 (Deprotection of Benzyl)

Deprotection of the compound (IIJ) obtained above is performed by catalytic hydrogenation as described in Step 3 to obtain a compound (IIK).

(15) Step 15 (Acylation)

The hydroxyl group of the compound (IIK) is protected by an acyl group such as an acetyl group to obtain a compound (IIL). The compound (IIK), acetic anhydride, pivaloyl chloride, benzoyl chloride etc. are allowed to react in a solvent in the presence of an appropriate base to obtain a compound (IIL). Examples of the solvent to be used in the reaction include chloroform, dichloromethane, dioxane, ethyl acetate, tetrahydrofuran and N,N-dimethylformamide. Preferable examples of the base include triethylamine, collidine and pyridine. As the catalyst, 4-dimethylaminopyridine may be used. The reaction temperature is preferably 0° C. to room temperature.

(16) Step 16 (Deprotection)

From the compound (IIL), the protecting group of the amino group is removed to obtain a compound (IIM). In the case of a Boc group, the compound (IIL) is allowed to react with a hydrochloric acid or trifluoroacetic acid in a solvent such as dichloromethane, chloroform or dioxane or without using a solvent. In the case of an Fmoc group, the compound (IIL) is allowed to react preferably with piperidine or morpholine in N,N-dimethylformamide.

(17) Step 17 (Formation of Urea)

A compound (IIN) can be synthesized from the compound (IIM) in the same process as in Step 11 above.

(18) Step 18 (Deprotection)

The acyl group of the compound (IIN) is removed in basic conditions to obtain the compound (I) of the invention. Examples of the base may include sodium methoxide, sodium hydroxide, lithium hydroxide, potassium carbonate, cesium carbonate and triethylamine. Preferable examples of the solvent include methanol, ethanol, and hydrous methanol.

Production Process 5

The compound (I) of the invention where Y is —O—(CH$_2$)n- and Z is —NHCON(R$^B$)R$^C$ can be synthesized by the following method. Note that, in the scheme, Y$^2$ is a C$_{2-4}$ alkylene group, and other reference symbols are the same as defined above.

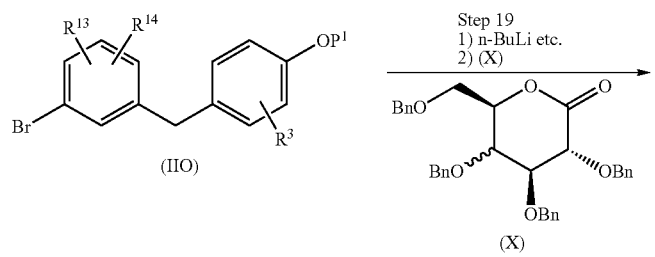

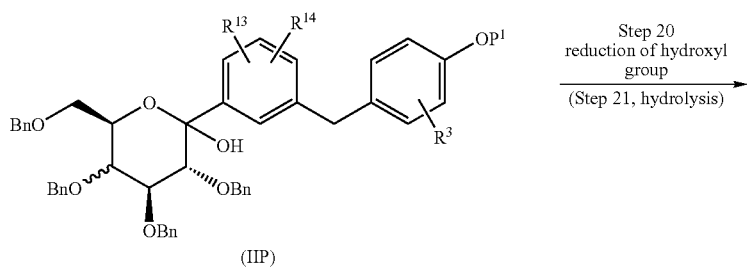

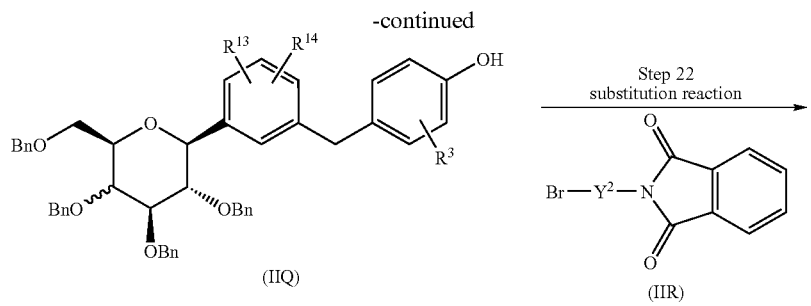
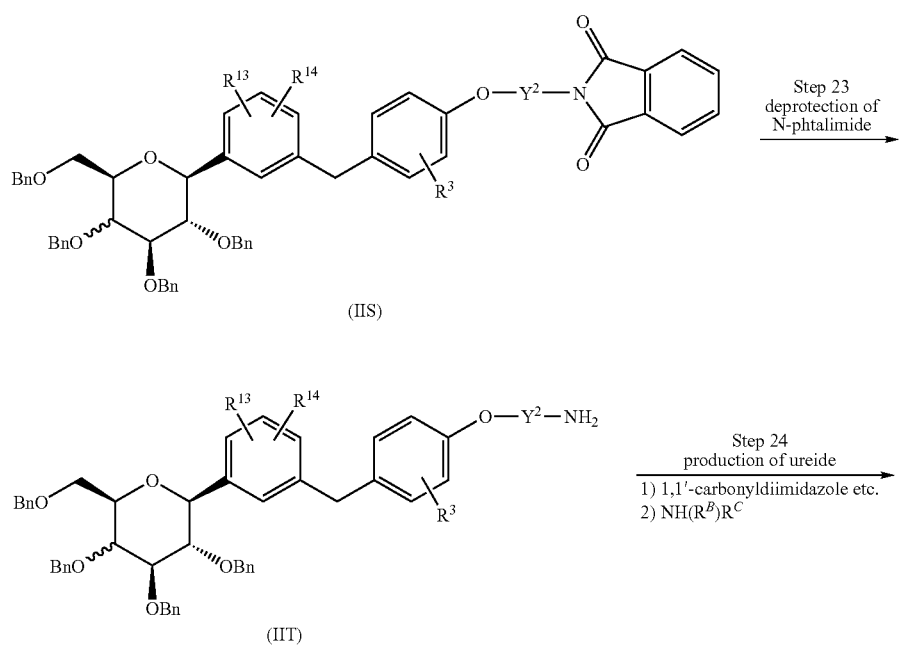
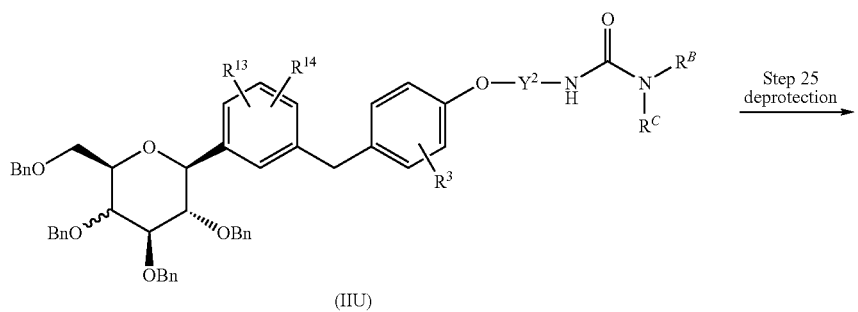
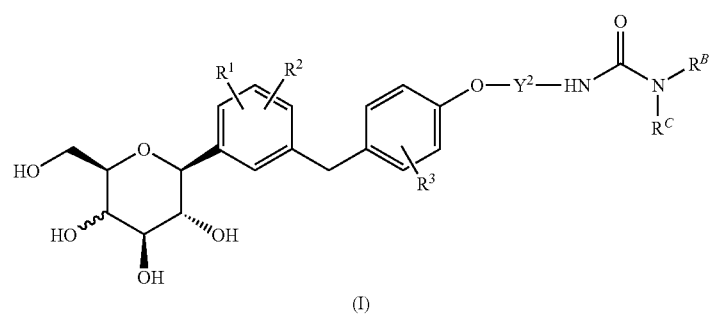

(19) Step 19

A compound (IIP) can be prepared in the same manner as in Production process 3, step 6 from a compound (IIO) (which can be synthesized in accordance with the disclosure of WO06/073197) and a compound (X).

(20-21) Step 20 and Step 21

The compound (IIP) is subjected to reduction of a hydroxyl group and removing a protecting group $P^1$ in the same manner as in Production process 3, steps 7 and 8 to obtain a compound (IIQ).

(22) Step 22

The compound (IIQ) and a reagent (IIR) are allowed to react in the presence of a base to obtain a compound (IIS). Preferable examples of the base used herein may include sodium carbonate, potassium carbonate, potassium hydroxide, sodium hydride, pyridine, triethylamine. Examples of the solvent to be used in this reaction may include dioxane, acetonitrile, toluene, dimethoxyethane, tetrahydrofuran, N,N-dimethylformamide. The reaction temperature herein is preferably 20° C. to 100° C.

(23) Step 23

The compound (IIS) is subjected to removing a phthalimide group in the same manner as in Production process 3, step 10 to obtain a compound (IIT).

(24) Step 24

A compound (IIU) can be prepared in the same manner as in Production process 3, step 11 from the compound (IIT).

(25) Step 25

The compound (IIU) is subjected to deprotection in the same manner as in Production process 3, step 12 to obtain the compound (I) of the invention where Y is —O—$(CH_2)$n-.

Production Process 6

The compound (I) of the invention where Y is —O—$(CH_2)$n- and Z is —$CONHR^4$ can be synthesized also by the following method. Note that, in the scheme, $Y^3$ is a $C_{1-4}$ alkylene group, $L_1$ is a leaving group such as a halogen atom, $MeSO_2O$—, etc. and other reference symbols are the same as defined above.

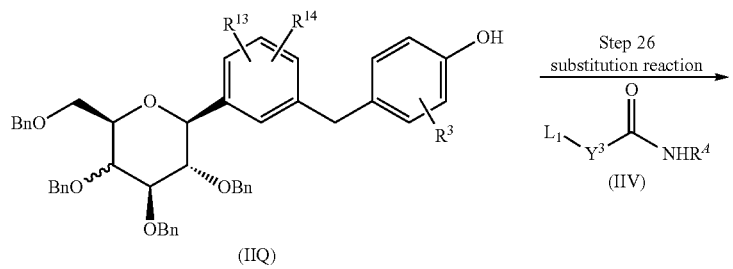

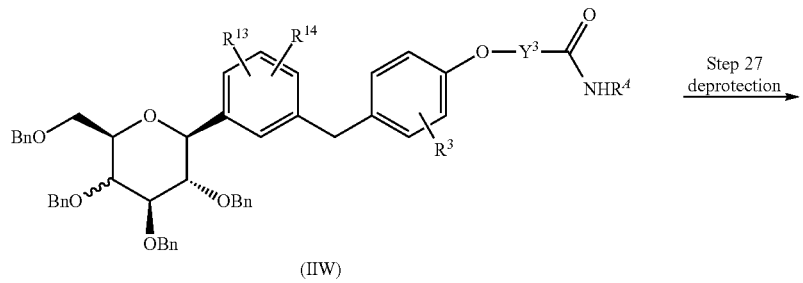

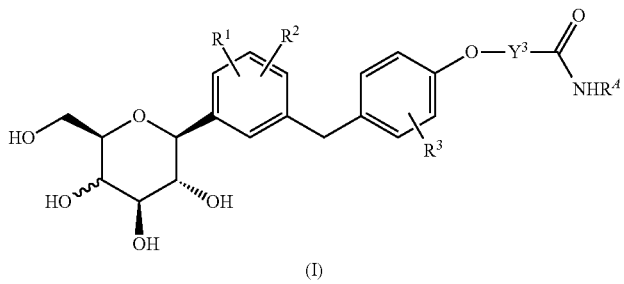

(26) Step 26

The compound (IIQ) and a compound (IIV) are allowed to react in the presence of a base to obtain a compound (IIW). Preferable examples of the base used herein may include sodium hydride, sodium carbonate, potassium carbonate, cesium carbonate, n-butyl lithium. Preferable examples of the solvent to be used in this reaction may include tetrahydrofuran, diethylether, N,N-dimethylformamide, acetone, DMSO. The reaction temperature herein is 0° C. to 60° C.

(27) Step 27

The compound (IIW) is subjected to deprotection in the same manner as in Production process 3, step 12 to obtain the compound (I) of the invention where Y is —O—(CH$_2$)n- and Z is —CONHR$^A$.

Production Process 7

The compound (I) of the invention where Z is a heterocycloalkyl group such as 2,4-dioxoimidazolindinyl can be synthesized by the following method. Note that, in the scheme, R$^N$ is a hydroxyl group, a C$_{1-4}$ alkoxy group or a phenyl group, and other reference symbols are the same as defined above.

(28) Step 28

The compound (IIM) is condensed with R$^A$R$^B$NH, for example, an amine having a carbonyl group at the α-position such as 2-aminoacetophenone or an amino acid in the same manner in Production process 4, step 17 to obtain a compound (IIX).

(29) Step 29 (Deprotection under a Base Condition)

The Compound (IIX) is subjected to deprotection of the acetyl group and at the same time, an intramolecular cyclization of the side chain of the compound (IIX) to obtain the compound (I) of the invention where Z is the above-defined heterocycloalkyl group. The base used herein is preferably sodium methoxide, and the solvent is preferably methanol or ethanol.

Production Process 8

The compound (I) of the invention where Y is a single bond, a methylene group or —O—(CH$_2$)n- and Z is —NHC(=NH)NH$_2$ can be synthesized by the following method.

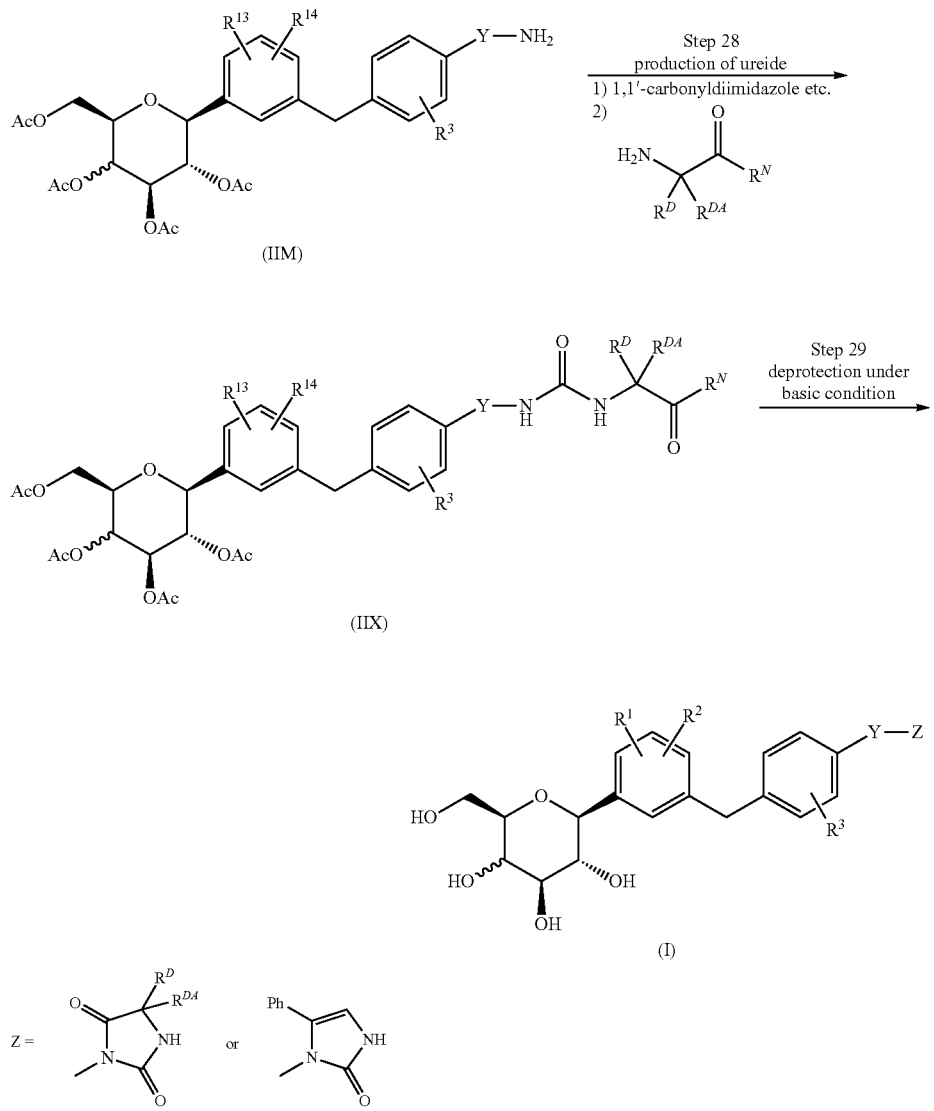

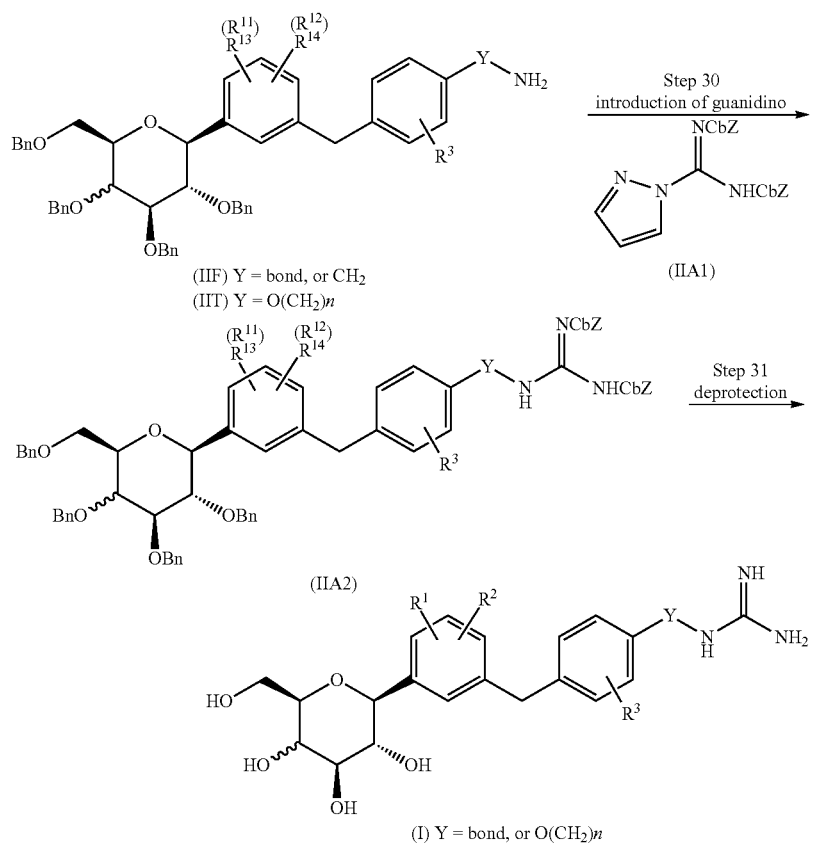

(30) Step 30 (Introduction of a Guanidino Group)

The compound (IIF) or the compound (IIT) obtained in step 38 or step 23 is reacted with a reagent (IIA1) to obtain a compound (IIA2). Preferable Examples of the solvent to be used in this reaction may include tetrahydrofuran, N,N-dimethylformamide, methanol, ethanol, isopropanol, ethyl acetate, toluene. The reaction temperature herein is from a room temperature to a reflux temperature.

(31) Step 31

The compound (IIA2) is subjected to deprotection in the same manner as in Production process 3, step 12 to obtain the compound (I) of the invention where Y is a single bond, a methylene group or —O—(CH$_2$)n- and Z is —NHC(=NH)NH$_2$.

Production processes of intermediates for producing the compound (I) will be described below.

Process for Producing Intermediate (IA)

A process for producing an intermediate (IA) required for production of the compound (I) of the invention will be described below. Note that D$^1$ represents Li or MgBr. Other reference symbols are the same as defined above.

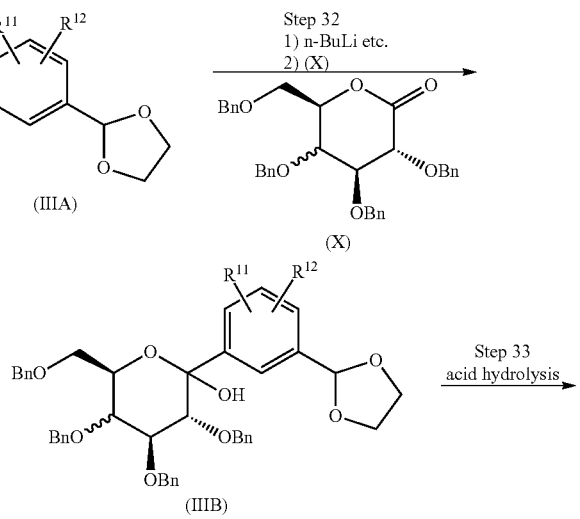

-continued

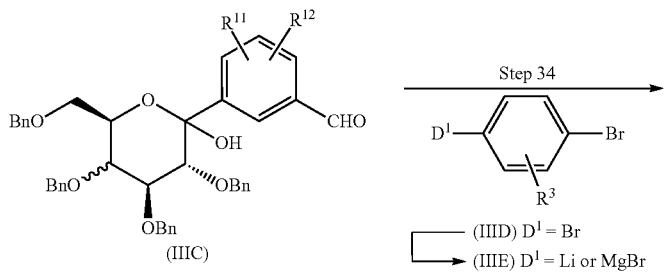

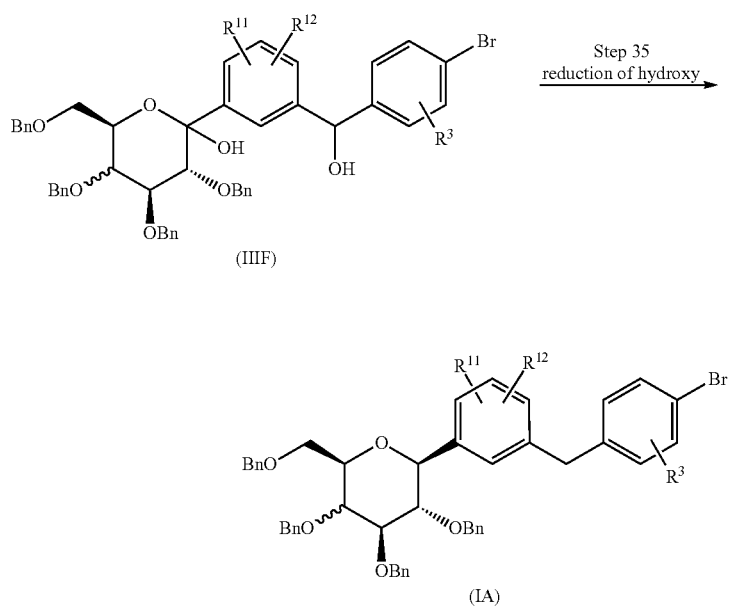

(32) Step 32

An aryllithium reagent can be prepared from an intermediate compound (IIIA) (which can be synthesized in accordance with the disclosure of WO06/073197) by use of an organic metal reagent such as n-butyllithium, sec-butyllithium or tert-butyllithium. The aryllithium reagent is condensed with δ-lactone (X) to obtain a compound (IIIB). Examples of the solvent to be used in this reaction may include tetrahydrofuran, diethyl ether and toluene. The reaction temperature is −80° C. to room temperature, and preferably, −78° C. to −25° C.

(33) Step 33 (Acid Hydrolysis)

The acetal group of the compound (IIIB) is hydrolyzed by using hydrochloric acid and p-toluenesulfonic acid monohydrate, etc. to produce a compound (IIIC). Preferable examples of the solvent to be used herein include tetrahydrofuran, ethanol, methanol, water and mixtures thereof. The reaction temperature is from 4° C. to room temperature, and preferably, room temperature. The reaction time varies depending upon the reaction temperature and it is from 1 hour to 24 hours.

(34) Step 34

A monolithium reagent compound (IIIE) can be produced from a compound (IIID) by use of one equivalent of n-butyllithium, sec-butyllithium or tert-butyllithium to the compound (IIID). Examples of the solvent to be used in this reaction may include tetrahydrofuran, diethyl ether and toluene. The reaction temperature is from −80° C. to room temperature, and preferably, −78° C. to −25° C. The reaction time is preferably from 5 minutes to 30 minutes. Furthermore, Grignard reagent (IIIE) can be also produced by using one equivalent of metal magnesium. Examples of the solvent to be used in this reaction may include tetrahydrofuran, diethyl ether and diglym. Subsequently, the reagent (IIIE) is added to the intermediate compound (IIIC) to form a compound (IIIF). The reaction temperature is from −80° C. to room temperature, and preferably, −78° C. to −25° C.

(35) Step 35 (Reduction of Hydroxyl Group)

The compound (IA) can be synthesized from the compound (IIIF) in the same manner as in Step 7 above.

Process for Producing Intermediate (IIB) or (IIF)

The intermediate (IIB) or (IIF) described above can be synthesized in another pathway as shown below

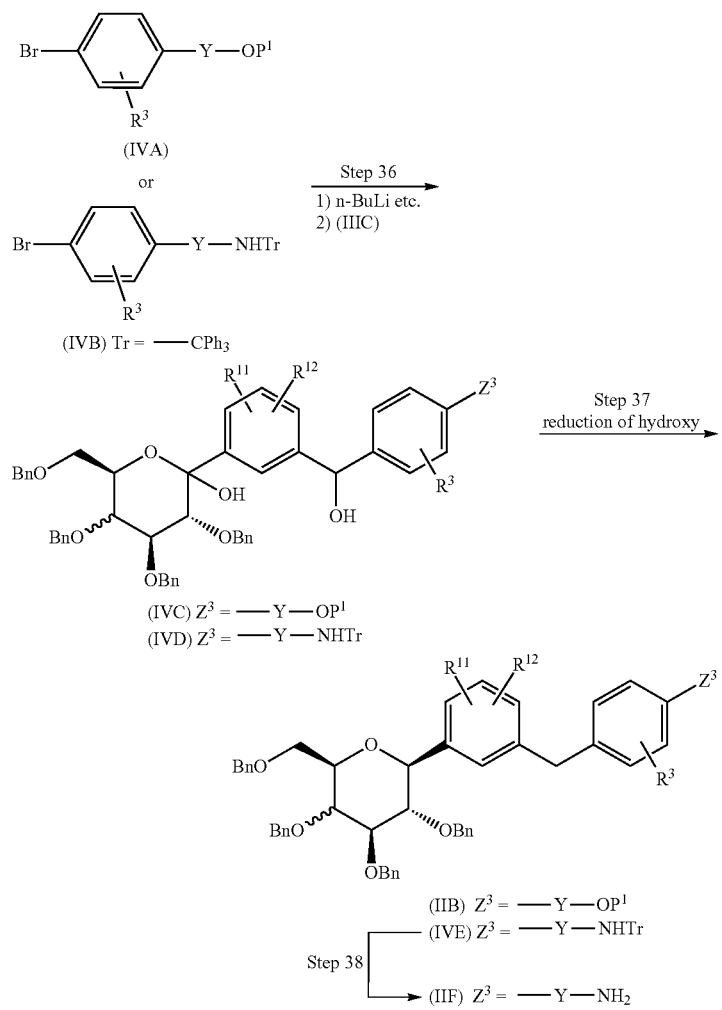

(36) Step 36

A compound (IVC) or (IVD) can be synthesized from a compound (IVA) or (IVB) in the same manner as in Step 34 above.

(37) Step 37 (Reduction of Hydroxyl Group)

The intermediate (IIB) can be synthesized from the compound (IVC) in the same manner as in Step 7 above. Furthermore, an intermediate (IVE) can be synthesized from the compound (IVD).

(38) Step 38

The compound (IVE) is treated with hydrochloric acid or trifluoroacetic acid in chloroform or dichloromethane to remove a protecting group, trityl (Tr) of the amino group, with the result that an intermediate (IIF) can be synthesized. The reaction temperature herein is preferably 0° C. to room temperature.

The compound of the invention inhibits both activities of SGLT1 and SGLT2 which are involved in a glucose absorption suppression action from the digestive tract and urine glucose excretion action, respectively. Through inhibition of SGLT1, the compound of the invention can treat diabetes and improve IGT to thereby prevent the progression of diabetes. Through inhibition of SGLT2, the compound of the invention can prevent sugar reabsorption and remove excess sugar from the body to thereby treat diabetes. Thus, the compound of the present invention can correct hyperglycemia without the exhaustion of the pancreatic β cells due to glucose toxicity, and improve insulin resistance.

Therefore, the compound of the present invention can be used as an SGLT1 inhibitor and an SGLT2 inhibitor. The present invention provides a pharmaceutical preparation for preventing or treating diseases or conditions which can be ameliorated by inhibition of SGLT1 and SGLT2 activities, e.g. diabetes, diabetes-related diseases, and diabetes complications.

The term "diabetes" used herein include Type 1 diabetes and Type 2 diabetes and other types of diabetes with specific etiology.

Examples of the term "diabetes-related diseases" used herein may include obesity, hyperinsulinemia, abonormal carbohydrate metabolism, hyperlipidemia, hypercholesterolemia, hypertriglyceridemia, abonormal lipid metabolism, hypertension, congestive heart failure, edema, hyperuricemia and gout.

The term "diabetes complications" used herein can be classified into acute complications and chronic complications.

Examples of the term "acute complications" may include hyperglycemia (e.g., ketoacidosis) and infectious diseases (e.g., skin, soft tissue, biliary tract system, respiratory system and urinary tract infections).

Examples of the term "chronic complications" may include microangiopathy (e.g., nephropathy, retinopathy), arteriosclerosis (e.g., atherosclerosis, myocardial infarction, cerebral infarction, lower limb arterial occlusive disease), neuropathy (e.g., sensory nerves, motor nerves, autonomic nerves), foot gangrene, etc.

Examples of major complications include diabetic retinopathy, diabetic nephropathy and diabetic neuropathy.

The compound of the invention may also be used in combination with any medicinal drug (hereinafter, simply referred to as "a concomitant drug") such as diabetes drugs, diabetic complication drugs, antilipidemic drugs, antihypertensive drugs, anti-obesity drugs, diuretic drugs and antithrombotic drugs, which depends on a different mechanism of action other than inhibition of SGLT1 and SGLT2 activities. When combined with other drugs, the compound of the present invention can be expected to produce as enhancement of the effect and a reduction of the dose of the compound. In this case, administration time of the compound of the invention and the concomitant drug are not limited. They may be administered to the subject at the same or different times. Furthermore, the compound of the invention and the concomitant drug may be administered as two independent preparations each containing an active ingredient or as a single preparation containing both of them as an active ingredient. The dose of the concomitant drug may be appropriately chosen based on the dosage clinically used. The blend ratio of the compound of the invention to the concomitant drug may be appropriately chosen in consideration of the subject to be administered, administration route, target disease, symptom and combination. For example, when the subject to be administered is a human, the concomitant drug may be used in an amount of 0.01 to 100 parts by mass relative to 1 part by mass of the compound of the invention.

Note that examples of the diabetes drugs may include insulin preparations (e.g., preparations of animal insulin extracted from bovine and swine pancreas; preparations of human insulin genetically synthesized by using *Escherichia coli* or yeast; insulin zinc; protamine insulin zinc, an insulin fragment or a derivative (e.g., INS-1), an oral insulin preparation), an insulin resistivity improver (e.g., pioglitazone or a salt thereof (preferably a hydrochloride), rosiglitazone or a salt thereof (preferably a maleate), rivoglitazone (CS-011)(R-119702), sipoglitazar (TAK-654), metaglidasen (MBX-102), naveglitazar (LY-519818), MX-6054, balaglitazone (NN-2344), T-131 (AMG131), a PPARγ agonist, a PPARγ antagonist, a PPARγ/α dual agonist, an α-glucocidase inhibitor (e.g., voglibose, acarbose, miglitol, emiglitate), a biguanide agent (e.g., phenformin, metformin, buformin or salts thereof (e.g., a hydrochloride, fumarate, succinate)), an insulin secretagogue (sulfonylurea (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or calcium salt hydrates thereof), a GPR40 agonist, a GPR40 antagonist, a GLP-1 receptor agonist (e.g., GLP-1, GLP-1MR agent, liraglutide (NN-2211), exenatide (AC-2993)(exendin-4), exenatide LAR, BIM-51077, Aib (8, 35) hGLP-1(7, 37)NH2, CJC-1131, AVE0010, GSK-716155), an amylin agonist (e.g., pramlintide), a phosphothyrosinphosphatase inhibitor (e.g., sodium vanadate), a dipeptidylpeptidase IV inhibitor (e.g., compounds described in WO02/038541, NVP-DPP-278, PT-100, P32/98, vildagliptin (LAF-237), P93/01, sitagliptin (MK-431), saxagliptin (BMS-477118), SYR-322, MP-513, T-6666, GRC-8200), a β3 agonist (e.g., AJ-9677, AZ40140), a glyconeogenesis inhibitor (e.g., a glycogen phosphorylase inhibitor, a glucose-6-phosphatase inhibitor, a glucagon antagonist, a fructose-1,6-bisphosphatase inhibitor), an SGLT (sodium-glucose cotransporter) inhibitor (e.g., compounds described in WO04/014931, WO04/089967, WO06/073197, T-1095, sergliflozin (GSK-869682), GSK-189075, KGT-1251, KGT-1681, KGA-2727, BMS-512148, AVE2268, SAR7226), a 11β-hydroxysteroid dehydrogenase inhibitor (e.g., compounds described in WO06051662, BVT-3498, INCB13739), a GPR119 agonist (e.g., PSN-632408, APD-668), adiponectin or an agonist thereof, an IKK inhibitor (e.g., AS-2868), an AMPK activator, a leptin resistivity improver, a somatostatin receptor agonist, a glucokinase activator (e.g., Ro-28-1675), a pancreatic lipase inhibitor (e.g., orlistat, ATL-962), and a DGAT-1 inhibitor.

Examples of the diabetic complication drugs may include an aldose reductase inhibitor (e.g., tolrestat, epalrestat, zenarestat, zopolrestat, minalrestat, fidarestat, CT-112), a neurotrophy factor and an augmentation drug thereof (e.g., NGF, NT-3, BDNF, a neurotrophin production/secretagogue), a nervous system reactivation promoter (e.g., Y-128), a PKC inhibitor (e.g., ruboxistaurin mesylate; LY-333531), an AGE inhibitor (e.g., ALT946, pimagedine, piratoxathin, N-phenacylthiazolium bromide (ALT766), ALT-711, EXO-226, pyridorin, pyridoxamine), an active oxygen erasing agent (e.g., thioctic acid), a cerebral vasodilating agent (e.g., tiapride, mexiletine), a somatostatin receptor agonist (e.g., BIM 23190) and an apoptosis signal regulating kinase-1(ASK-1) inhibitor.

Examples of the anti-hyperlipidemia drugs may include statin compounds (e.g., pravastatin, simvastatin, lovastatin, atorvastatin, fluvastatin, itavastatin, rosuvastatin, pitavastatin or salts thereof (e.g., sodium salt, calcium salt)), a squalene synthase inhibitor (e.g., TAK-475), a fibrate compound (e.g., bezafibrate, clofibrate, symfibrate, clinofibrate), an ACAT inhibitor (e.g., avasimibe, eflucimibe), an anion exchange resin (e.g., cholestyramine), probucol, a nicotinic drug (e.g., nicomol, niceritrol), ethyl icosapentate, a vegetable sterol (e.g., soysterol, γ-oryzanol), a CETP inhibitor (e.g., torcetrapib, JTT-705, JTT-302, FM-VP4) and a cholesterol absorption depressant (e.g., ezetimibe).

Examples of the antihypertensive agent may include an angiotensin-converting enzyme inhibitor (e.g., captopril, enalapril, delapril), an angiotensin II antagonist (e.g., candesartan, cilexetil, losartan, eprosartan, valsartan, telmisartan, irbesartan, tasosartan, azilsartan (TAK-536)), a calcium antagonist (e.g., manidipine, nifedipine, amlodipine, efonidipine, nicardipine), a potassium channel opening agent (e.g., levcromakalim, L-27152, AL0671, NIP-121), and clonidine.

Examples of the anti-obesity drugs may include a central anti-obesity drug (example, dexfenfluramine, fenfluramine, phentermine, sibutramine, amfepramone, dexamphetamine, mazindol, phenylpropanolamine, clobenzorex), an MCH receptor antagonist (e.g., compounds described in WO06/035967, SB-568849; SNAP-7941, T-226296); a neuropeptide Y antagonist (e.g., CP-422935), a cannabinoid receptor antagonist (e.g., rimonabant (SR-141716), SR-147778); a ghrelin antagonist, a 11β-hydroxysteroid dehydrogenase inhibitor (e.g., BVT-3498, INCB13739)), a pancreatic lipase inhibitor (e.g., orlistat, ATL-962), a DGAT-1 inhibitor, a β3 agonist (e.g., AJ-9677, AZ40140), a peptidergic anorexiant drug (e.g., leptin, CNTF (ciliary body neurotrophy factor)), a cholecystokinin agonist (e.g., lintitript, FPL-15849) and a feeding deterrent (e.g., P-57).

Examples of the diuretic drugs may include a xanthine derivative (e.g., sodium theobromine salicylate, calcium theobromine salicylate), a thiazide preparation (e.g., ethiazide, cyclopenthiazide, trichlormethiazide, hydrochlorothiazide, hydroflumethiazide, bentylhydrochlorothiazide, penflutiazide, polythiazide, methyclothiazide), an anti-aldosterone preparation (e.g., spironolactone, triamteren), a carbonic anhydrase inhibitor (e.g., acetazolamide), a chlorobenzene sulfoneamide preparation (e.g., chlorthalidone, mefruside, indapamide), azosemide, isosorbide, ethacrynic acid, piretanide, bumetanide and furosemide.

Examples of the antithrombotic drugs may include heparin (e.g., heparin sodium, heparin calcium, dalteparin sodium, AVE-5026), warfarin (e.g., warfarin potassium), an anti-thrombin agent (e.g., argatroban, ximelagatran, dabigatran, odiparcil, lepirudin, bivalirudin, desirudin, ART-123, idraparinux, SR-123781, AZD-0837, MCC-977, TGN-255, TGN-167, RWJ-58436, LB-30870, MPC-0920, pegmusirudin, Org-426751), a thrombolytic agent (e.g., urokinase, tisokinase, alteplase, nateplase, monteplase, pamiteplase), a platelet aggregation inhibitor (e.g., ticlepidine hydrochloride, cilostazol, ethyl icosapentate, beraprost sodium, sarpogrelate hydrochloride), a factor Xa inhibitor (e.g., fondaparinux, BAY-59-7939, DU-176b, YM-150, SR-126517, apixaban, razaxaban, LY-517717, MLN-102, octaparine, otamixaban, EMD-503982, TC-10, CS-3030, AVE-3247, GSK-813893, KFA-1982), a plasma carboxy peptidase B inhibitor (or known as an active-form thrombin-activatable fibrinolysis inhibitor [TAFIa]) such as AZD-9684, EF-6265, MN-462.

The pharmaceutical preparation of the present invention can be administered systemically or topically via oral route or parenteral (e.g., intrarectal, subcutaneous, intramuscular, intravenous, percutaneous) route.

For use as a pharmaceutical preparation, the compound of the present invention may be formulated into any desired dosage form selected from solid compositions, liquid compositions and other compositions, as appropriate for the intended purpose. The pharmaceutical preparation of the present invention can be prepared by blending the compound of the present invention with pharmaceutically acceptable carrier(s). More specifically, the compound of the present invention may be supplemented with commonly used excipients, extenders, binders, disintegrating agents, coating agents, sugar-coating agents, pH regulators, solubilizers, aqueous or non-aqueous solvents and so on, and then formulated using standard techniques into tablets, pills, capsules, granules, powders, solutions, emulsions, suspensions, injections, etc.

Also, the compound of the present invention may be modified to form an inclusion compound with, e.g., α-, β- or γ-cyclodextrin or methylated cyclodextrin before being formulated.

The dose of the compound of present invention will vary depending on the disease or symptom to be treated, body weight, age, gender, and administration route, but it falls 0.1 to 1000 mg/kg weight/day/adult, preferably 0.1 to 200 mg/kg weight/day/adult, and more preferably, 0.1 to 10 mg/kg weight/day/adult. This can be administered once to several times per day.

REFERENCE EXAMPLES

Preparation of intermediates required to prepare the compounds of the present invention will be illustrated below with reference to the following Reference Examples.

Reference Example 1

Preparation of 2-[4-(benzyloxy)-5-bromo-2-methylphenyl]-1,3-dioxolane

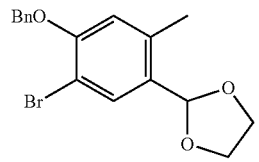

(1) Preparation of
1-[4-(benzyloxy)-2-methylphenyl]ethanone

To an N,N-dimethylformamide solution (20 mL) of 4'-hydroxy-2'-methylacetophenone (3.06 g, 20 mmol) were added potassium carbonate (3.66 g, 26.4 mmol), benzyl bromide (2.7 mL, 22.4 mmol), and n-Bu$_4$NI (0.75 g, 2.03 mmol), and the mixture was stirred for 14 hours at room temperature. To the reaction solution cooled in ice were added a saturated solution of ammonium chloride, subsequently water and ethyl acetate to separate an organic layer. The organic layer was washed with 20% aqueous solution of sodium thiosulfate and brine, and dried with anhydrous magnesium sulfate. The drying agent was filtered off, and the solvent was evaporated under reduced pressure. Thus obtained residue was purified with silica gel column chromatography (hexane:ethyl acetate=8:1 to 6:1) to obtain the title compound (5.05 g, quant.) as a colorless powder.

1H NMR (300 MHz, CHLOROFORM-D) δ ppm 2.55 (s, 3H) 2.57 (s, 3H) 5.11 (s, 2H) 6.78-6.86 (m, 2H) 7.30-7.47 (m, 5H) 7.75 (dd, J=7.93, 1.09 Hz, 1H).

(2) Preparation of
4-(benzyloxy)-5-bromo-2-methylbenzoic acid

To an acetone solution (300 mL) of 1-[4-(benzyloxy)-2-methylphenyl]ethanone (20.9 g, 87.1 mmol) were added an aqueous solution (100 mL) of NaBr (9.86 g, 95.9 mmol), water (200 mL), and Oxone (registered trade mark, oxonepersulfuric acid chloride, from Aldrich) (59.0 g, 95.9 mmol), and the mixture was stirred 2.5 hours at room temperature. To the reaction solution cooled in ice were added an aqueous solution (50 mL) of sodium sulfite (20 g), subsequently water and ethyl acetate to separate an organic layer. The organic layer was washed with 20% aqueous solution of sodium sulfite and brine, and dried with anhydrous magnesium sulfate. The drying agent was filtered off, and the solvent was evaporated under reduced pressure to obtain a mixture (27.2 g) of 1-[4-(benzyloxy)-5-bromo-2-methylphenyl]ethanone and 1-[4-(benzyloxy)-3-bromo-2-methylphenyl]ethanone. To the mixture were added a 5% aqueous solution (300 mL, 255 mol) of sodium hypochlorite and an aqueous solution (10 mL) of potassium hydroxide (4.80 g, 85.3 mmol), stirred at 120° C. for an hour, cooled to room temperature, and precipitated insoluble matter was filtered. To this insoluble matter was added 2 M hydrochloric acid, and the resulting mixture was extracted with ethyl acetate. The organic layer was washed with 2 M hydrochloric acid and brine, and dried with anhydrous magnesium sulfate. The drying agent was filtered off, and the solvent was evaporated under reduced pressure.

Thus obtained residue was washed with methanol to obtain the title compound (16.6 g, 59%, 2 steps) as a colorless powder.

1H NMR (300 MHz, DMSO-D6) δ ppm 2.45-2.57 (m, 3H) 5.28 (s, 2H) 7.18 (s, 1H) 7.31-7.54 (m, 5H) 8.03 (s, 1H) 12.83 (brs, 1H).

ESI m/z=319(M−H), 321(M+2−H).

(3) Preparation of 2-[4-(benzyloxy)-5-bromo-2-methylphenyl]-1,3-dioxolane

To a suspension of 4-(benzyloxy)-5-bromo-2-methylbenzoic acid (16.6 g, 51.7 mmol) in chloroform (80 mL) were added oxalyl chloride (5 mL, 56.9 mmol) and N,N-dimethylformamide (6 drops), and the mixture was stirred for an hour at room temperature. And then the reaction solution was concentrated to obtain 4-(benzyloxy)-5-bromo-2-methylbenzoyl chloride. Then to a chloroform suspension (60 mL) of N,O-dimethylhydroxylamine hydrochloride (5.55 g, 56.9 mmol) and triethylamine (15 mL, 103 mmol) cooled in ice was added dropwise a chloroform solution (60 mL) of 4-(benzyloxy)-5-bromo-2-methylbenzoyl chloride, and the mixture was stirred for an hour at room temperature. To the reaction solution cooled in ice were added water and chloroform to separate an organic layer. The organic layer was washed with a saturated sodium bicarbonate aqueous solution and brine, and dried with anhydrous magnesium sulfate. The drying agent was filtered off, and the solvent was evaporated under reduced pressure to obtain 4-(benzyloxy)-5-bromo-N-methoxy-N-methylbenzamide. To a tetrahydrofuran solution (150 mL) of the 4-(benzyloxy)-5-bromo-N-methoxy-N-methylbenzamide was added at −10° C. lithium aluminum hydride (1.96 g, 51.7 mmol), and the mixture was stirred for an hour at the same temperature. To the reaction solution were added 1 M hydrochloric acid, and then ethyl acetate to separate an organic layer. The organic layer was washed with 1 M hydrochloric acid, a saturated sodium bicarbonate aqueous solution and brine, and dried with anhydrous magnesium sulfate. The drying agent was filtered off, and the solvent was evaporated under reduced pressure to obtain 4-(benzyloxy)-5-bromo-2-methylbenzaldehyde. To a toluene solution (120 mL) of the 4-(benzyloxy)-5-bromo-2-methylbenzaldehyde were added ethylene glycol (30 mL, 517 mmol) and p-toluenesulfonic acid monohydrate (0.50 g, 2.58 mmol), and heated to reflux for 1.5 hours with a Dean-Stark apparatus. To the reaction solution was added ethyl acetate to separate an organic layer. The organic layer was washed with water, a saturated sodium bicarbonate aqueous solution and brine, and dried with anhydrous magnesium sulfate. The drying agent was filtered off, and the solvent was evaporated under reduced pressure. Thus obtained residue was purified with silica gel column chromatography (hexane:ethyl acetate=5:1). In addition, the residue was further purified with NH type silica gel column chromatography (chloroform) to obtain the title compound (12.8 g, 71%, 3 steps) as a colorless powder.

1H NMR (300 MHz, CHLOROFORM-D) δ ppm 2.34 (s, 3H) 3.92-4.19 (m, 4H) 5.15 (s, 2H) 5.87 (s, 1H) 6.74 (s, 1H) 7.27-7.51 (m, 5H) 7.72 (s, 1H).

Reference Example 1-2

Preparation of 2-[4-(benzyloxy)-5-bromo-2-methylphenyl]-1,3-dioxolane

To a methanol suspension (3.75 mL) of 4-(benzyloxy)-2-methylbenzaldehyde (0.50 g, 2.21 mmol) cooled in ice was added pyridinium hydrobromide perbromide (1.06 g, 3.32 mmol), and the mixture was stirred for 30 minutes. The reaction mixture was stirred for 2.5 hours at room temperature. To the reaction solution were added 20% solution of $Na_2SO_3$, water and ethyl acetate. The resulting mixture was extracted with ethyl acetate. To the organic layer was added 1 M hydrochloric acid (20 mL), and the mixture was stirred for 5 minutes. The organic layer was separated, washed with a saturated sodium bicarbonate aqueous solution and brine, and dried with anhydrous magnesium sulfate. The drying agent was filtered off, and the solvent was evaporated under reduced pressure to obtain 1.03 g of a residue. To a toluene solution (7.0 mL) of the residue were added ethylene glycol (1.89 mL, 33.9 mmol) and pyridinium p-toluenesulfonate (43 mg, 0.170 mmol), and heated to reflux for 14 hours with a Dean-Stark apparatus. After the reaction solution was cooled, its organic layer was washed with a saturated sodium bicarbonate aqueous solution and brine, and dried with anhydrous magnesium sulfate. The drying agent was filtered off, and the solvent was evaporated under reduced pressure. Thus obtained residue was recrystallized from hexane/ethyl acetate (10:1) to obtain the title compound (748 mg, 63%).

Reference Example 2

Preparation of (1S)-1,5-anhydro-2,3,4,6-tetra-O-benzyl-1-[2-(benzyloxy)-5-(4-bromobenzyl)-4-methylphenyl]-D-glucitol

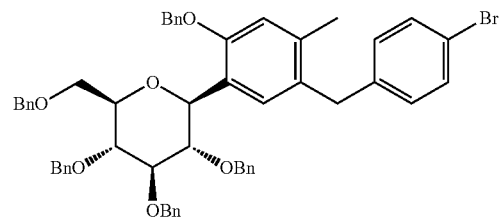

(1) Preparation of 2,3,4,6-tetra-O-benzyl-1-C-[2-(benzyloxy)-5-(1,3-dioxolan-2-yl)-4-methylphenyl]-D-glucopyranose To a tetrahydrofuran solution (36 mL) of 2-[4-(benzyloxy)-5-bromo-2-methylphenyl]-1,3-dioxolane (5.82 g, 16.6 mmol) was added dropwise under nitrogen atmosphere at −78° C. a 2.67 M n-butyllithium solution in hexane (6.40 mL, 16.6 mmol), and the mixture was stirred for 30 minutes at the same temperature. Then a tetrahydrofuran solution (18 mL) of 2,3,4,6-tetra-O-benzyl-D-glucono-1,5-lactone (8.16 g, 15.1 mmol) was added dropwise, and the mixture was stirred for 20 minutes at the same temperature. To the reaction solution was added a saturated aqueous solution of ammonium chloride, and the resulting mixture was extracted with ethyl acetate. The organic layer was washed with a saturated aqueous solution of ammonium chloride and brine, and dried with anhydrous magnesium sulfate. The drying agent was filtered off, and the solvent was evaporated under reduced pressure. Thus obtained residue was purified with silica gel column chromatography (hexane:ethyl acetate=3:1 to 2:1) to obtain the title compound (10.7 g, 87%) as a yellow oily compound.

1H NMR (300 MHz, CHLOROFORM-D) δ ppm 2.40 (s, 3H) 3.65-3.86 (m, 3H) 3.89-4.21 (m, 8H) 4.45-4.69 (m, 4H) 4.78-5.03 (m, 5H) 5.91 (s, 1H) 6.71 (s, 1H) 6.97 (dd, J=7.31, 2.18 Hz, 2H) 7.10-7.37 (m, 23H) 7.81 (s, 1H).

(2) Preparation of 2,3,4,6-tetra-O-benzyl-1-C-[2-(benzyloxy)-5-formyl-4-methylphenyl]-D-glucopyranose To a tetrahydrofuran solution (80 mL) of 2,3,4,6-tetra-O-benzyl-1-C-[2-(benzyloxy)-5-(1,3-dioxolan-2-yl)-4-methylphenyl]-D-glucopyranose (10.6 g, 13.0 mmol) cooled in ice was added 6 M hydrochloric acid (80 mL), and the mixture was stirred for 14 hours at room temperature. To the reaction solution was added ice water, and the resulting mixture was extracted with ethyl acetate. The organic layer was washed with a saturated sodium bicarbonate aqueous solution and brine, and dried with anhydrous magnesium sulfate. The drying agent was filtered off, and the solvent was evaporated under reduced pressure. Thus obtained residue was purified with silica gel column chromatography (hexane:ethyl acetate=2:1) to obtain the title compound (10.2 g, quant.) as a yellow oily compound.

1H NMR (300 MHz, CHLOROFORM-D) δ ppm 2.66 (s, 3H) 3.60-3.72 (m, 2H) 3.74-3.82 (m, 1H) 4.01 (t, J=9.09 Hz, 1H) 4.07-4.20 (m, 3H) 4.40-4.61 (m, 5H) 4.71-5.05 (m, 5H) 6.70 (s, 1H) 6.87 (d, J=6.68 Hz, 2H) 7.06-7.40 (m, 23H) 8.07 (s, 1H) 10.06 (s, 1H).

(3) Preparation of 2,3,4,6-tetra-O-benzyl-1-C-[2-(benzyloxy)-5-[(4-bromophenyl)(hydroxy)methyl]-4-methylphenyl]-D-glucopyranose To a tetrahydrofuran solution (80 mL) of 1,4-dibromobenzene (6.20 g, 26.1 mmol) was added dropwise under nitrogen atmosphere at −78° C. a 2.67 M n-butyllithium solution in hexane (10.5 mL, 26.1 mmol), and the mixture was stirred for 15 minutes at the same temperature. Then a tetrahydrofuran solution (20 mL) of 2,3,4,6-tetra-O-benzyl-1-C-[2-(benzyloxy)-5-formyl-4-methylphenyl]-D-glucopyranose (10.0 g, 13.0 mmol) was added dropwise, and the mixture was stirred for 30 minutes at the same temperature. To the reaction solution was added a saturated aqueous solution of ammonium chloride, and the resulting mixture was extracted with ethyl acetate. The organic layer was washed with brine, and dried with anhydrous magnesium sulfate. The drying agent was filtered off, and the solvent was evaporated under reduced pressure. Thus obtained residue was purified with silica gel column chromatography (hexane:ethyl acetate=2:1). In addition, the residue was further purified with NH type silica gel column chromatography (hexane:ethyl acetate=1:1) to obtain the yellow oily title compound (5.50 g, 46%) as a diastereomeric mixture.

1H NMR (300 MHz, CHLOROFORM-D) δ ppm 2.21 (s, 3H) 3.54-3.82 (m, 3H) 3.98-4.23 (m, 4H) 4.36-4.64 (m, 4H) 4.75-5.06 (m, 5H) 5.83-5.86 (m, 1H) 6.71 and 6.73 (each s, 1H) 6.89-7.44 (m, 29H) 7.67 and 7.71 (each s, 1H).

(4) Preparation of (1S)-1,5-anhydro-2,3,4,6-tetra-O-benzyl-1-[2-(benzyloxy)-5-(4-bromobenzyl)-4-methylphenyl]-D-glucitol To an acetonitrile solution (60 mL) of 2,3,4,6-tetra-O-benzyl-1-C-[2-(benzyloxy)-5-[(4-bromophenyl)(hydroxy)methyl]-4-methylphenyl]-D-glucopyranose (5.50 g, 5.96 mmol) were added under nitrogen atmosphere at −10° C. Et₃SiH (2.90 mL, 17.8 mmol) and BF₃.Et₂O (1.90 mL, 14.9 mmol), and the mixture was stirred for 15 minutes at the same temperature and the mixture was stirred for 2.5 hours at room temperature. To the reaction solution cooled in ice was added a saturated sodium bicarbonate aqueous solution and the resulting mixture was extracted with ethyl acetate. The organic layer was washed with brine, and dried with anhydrous magnesium sulfate. The drying agent was filtered off, and the solvent was evaporated under reduced pressure. Thus obtained residue was purified with silica gel column chromatography (hexane:ethyl acetate=15:1 to 10:1) to obtain the title compound (2.70 g, 51%) as a pale yellow oily compound.

1H NMR (300 MHz, CHLOROFORM-D) δ ppm 2.17 (s, 3H) 3.53-3.63 (m, 1H) 3.68-3.91 (m, 7H) 4.00 (d, J=11.04 Hz, 1H) 4.39-4.95 (m, 8H) 5.01 (s, 2H) 6.75 (s, 1H) 6.86-6.97 (m, 4H) 7.10-7.35 (m, 24H) 7.36-7.46 (m, 2H).

Reference Example 3

Preparation of (1S)-1,5-anhydro-2,3,4,6-tetra-O-benzyl-1-[2-(benzyloxy)-5-[4-[(1E)-3-carboxyprop-1-en-1-yl]benzyl]-4-methylphenyl]-D-glucitol

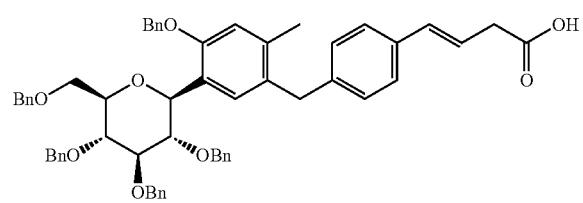

To an acetonitrile solution (8.8 mL) of (1S)-1,5-anhydro-2,3,4,6-tetra-O-benzyl-1-[2-(benzyloxy)-5-(4-bromobenzyl)-4-methylphenyl]-D-glucitol (780 mg, 0.876 mmol) were added vinyl acetate (184 mg, 2.14 mmol), palladium(II) acetate (20 mg, 0.0890 mmol), tri-O-tolylphosphine (54 mg, 0.177 mmol) and triethylamine (0.64 mL, 4.38 mmol), and reacted at 120° C. for 20 minutes with microwave manufactured by Biotage. The reaction solution was evaporated under reduced pressure. Thus obtained residue was purified with silica gel column chromatography (hexane:ethyl acetate=5:1, chloroform:methanol=40:1) to obtain the title compound (681 mg, 87%) as an orange-yellow amorphous compound.

1H NMR (600 MHz, CHLOROFORM-D) δ ppm 2.17 (s, 3H) 3.25 (d, J=5.50 Hz, 2H) 3.53-3.84 (m, 6H) 3.84-3.95 (m, 2H) 4.00 (d, J=10.55 Hz, 1H) 4.43 (d, J=10.55 Hz, 1H) 4.50 (d, J=11.92 Hz, 1H) 4.57-4.65 (m, 2H) 4.80-4.93 (m, 4H) 4.99 (s, 2H) 6.12-6.22 (m, 1H) 6.42 (d, J=15.59 Hz, 1H) 6.74 (s, 1H) 6.89-7.03 (m, 4H) 7.11-7.47 (m, 26H).

ESI m/z=893(M−H).

Reference Example 4

Preparation of (1S)-1-[5-[4-(2-aminoethyl)benzyl]-2-(benzyloxy)-4-methylphenyl]-1,5-anhydro-2,3,4,6-tetra-O-benzyl-D-glucitol

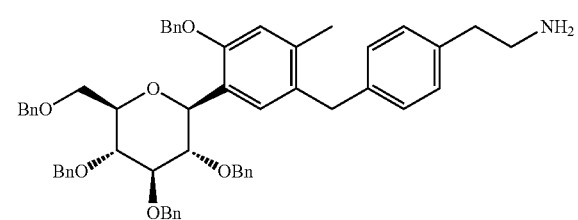

(1) Preparation of 2,3,4,6-tetra-O-benzyl-1-C-[2-(benzyloxy)-5-[hydroxy[4-[2-(tritylamino)ethyl]phenyl]methyl]-4-methylphenyl]-D-glucopyranose To a tetrahydrofuran solution (3 mL) of 2-(4-bromophenyl)-N-tritylethaneamine (0.814 g, 1.84 mmol) was added dropwise under nitrogen atmosphere at −78° C. a 2.66 M hexane solution of n-butyllithium (0.69 mL, 1.84 mmol), and the mixture was stirred for 30 minutes at the same temperature. Then a tetrahydrofuran solution (3 mL) of 2,3,4,6-tetra-O-benzyl-1-C-[2-(benzyloxy)-5-formyl-4-methylphenyl]-D-glucopyranose (0.670 g, 0.876 mmol) was added dropwise, and the mixture was stirred for 30 minutes at the same temperature. To the reaction solution was added water, and the resulting mixture was extracted with ethyl acetate. The organic layer was dried with anhydrous magnesium sulfate. The drying agent was filtered off, and the solvent was evaporated under reduced pressure. Thus obtained residue was purified with NH type silica gel column chromatography (chloroform) to obtain the title compound (0.634 g, 64%) as a yellow oily compound.

1H NMR (300 MHz, CHLOROFORM-D) δ ppm 2.12-2.22 (m, 3H) 2.30-2.43 (m, 2H) 2.65-2.76 (m, 2H) 3.64-3.84 (m, 3H) 3.99-4.22 (m, 4H) 4.42-4.65 (m, 5H) 4.75-5.04 (m, 5H) 5.83-5.91 (m, 1H) 6.67-6.72 (m, 1H) 6.88-7.43 (m, 44H).

(2) Preparation of (1S)-1,5-anhydro-2,3,4,6-tetra-O-benzyl-1-[2-(benzyloxy)-4-methyl-5-[4-[2-(tritylamino)ethyl]benzyl]phenyl]-D-glucitol To an acetonitrile solution (6 mL) of 2,3,4,6-tetra-O-benzyl-1-C-[2-(benzyloxy)-5-[hydroxy[4-[2-(tritylamino)ethyl]phenyl]methyl]-4-methylphenyl]-D-glucopyranose (0.638 g, 0.565 mmol) were added under nitrogen atmosphere at 0° C. Et₃SiH (0.27 mL, 1.695 mmol) and BF₃.Et₂O (1.58 mL, 1.24 mmol), and the mixture was stirred for 30 minutes at the same temperature. To the reaction solution cooled in ice was added a saturated sodium bicarbonate aqueous solution and the resulting mixture was extracted with ethyl acetate. The organic layer was dried with anhydrous magnesium sulfate. The drying agent was filtered off, and the solvent was evaporated under reduced pressure. Thus obtained residue was purified with silica gel column chromatography (hexane:ethyl acetate=9:1) to obtain the title compound (0.402 g, 59%) as a pale yellow oily compound.

1H NMR (300 MHz, CHLOROFORM-D) δ ppm 2.16 (s, 3H) 2.36 (t, J=6.84 Hz, 2H) 2.68 (t, J=6.84 Hz, 2H) 3.52-3.65 (m, 1H) 3.67-3.92 (m, 7H) 4.00 (d, J=10.88 Hz, 1H) 4.37-4.67 (m, 5H) 4.78-5.06 (m, 5H) 6.73 (s, 1H) 6.83-7.01 (m, 5H) 7.05-7.45 (m, 40H).

(3) Preparation of (1S)-1,5-anhydro-2,3,4,6-tetra-O-benzyl-1-[5-[4-(2-aminoethyl)benzyl]-2-(benzyloxy)-4-methylphenyl]-D-glucitol To a chloroform solution of (1S)-1,5-anhydro-2,3,4,6-tetra-O-benzyl-1-[2-(benzyloxy)-4-methyl-5-[4-[2-(tritylamino)ethyl]benzyl]phenyl]-D-glucitol (0.402 g, 0.336 mmol) was added at room temperature trifluoroacetate (0.5 mL), and the mixture was stirred for 3 hours at the same temperature. To the reaction solution was added ethanol and then the solvent was evaporated under reduced pressure. Thus obtained residue was purified with NH type silica gel column chromatography (hexane:ethyl acetate=4:6, chloroform:methanol=20:1) to obtain the title compound (0.296 g, quant.) as a colorless oily compound.

1H NMR (300 MHz, CHLOROFORM-D) δ ppm 2.20 (s, 3H) 2.65 (t, J=6.84 Hz, 2H) 2.89 (t, J=6.84 Hz, 2H) 3.52-3.95 (m, 8H) 4.00 (d, J=10.72 Hz, 1H) 4.38-4.67 (m, 5H) 4.81-5.04 (m, 5H) 6.74 (s, 1H) 6.88-7.45 (m, 30H).

Reference Example 5

Preparation of dibenzyl[(Z)-(allylamino)methylylidene]biscarbamate

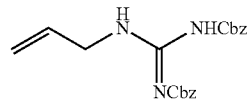

To a tetrahydrofuran solution (4.3 mL) of allylamine (250 mg, 4.38 mmol) was added N,N'-bis-benzyloxy carbonyl-1-guanyl pyrazole (1.98 g, 5.25 mmol), and the mixture was stirred overnight at room temperature. The reaction solution was evaporated under reduced pressure. Thus obtained residue was purified with silica gel column chromatography (hexane:ethyl acetate=4:1) to obtain the title compound (1.45 g, 90%) as a colorless powder.

1H NMR (300 MHz, CHLOROFORM-D) δ ppm 4.03-4.12 (m, 2H) 5.11-5.28 (m, 6H) 5.81-5.96 (m, 1H) 7.23-7.43 (m, 10H) 8.35-8.45 (m, 1H) 11.76 (s, 1H).

ESI m/z=368(M+H).

Reference Example 6

Preparation of N-allyl-4-methyl-piperazine-1-carboxyamide

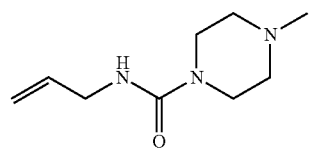

To a chloroform solution (70 mL) of allylamine (400 mg, 7.00 mmol) were added triethylamine (1.31 mL, 9.45 mmol) and 4-nitrophenyl chloroformate (1.62 g, 8.06 mmol), and the mixture was stirred overnight at room temperature. To this reaction solution was added 1-methylpiperazine (771 mg, 7.70 mmol), and the mixture was stirred overnight at room temperature. The reaction solution was evaporated under reduced pressure. To thus obtained residue was added ethyl acetate, and precipitated insoluble matter was filtered off. The filtrate was concentrated, and thus obtained residue was purified with NH type silica gel column chromatography (hexane:ethyl acetate=5:1, ethyl acetate), and silica gel column chromatography (ethyl acetate, chloroform:methanol=20:1 to 5:1) to obtain the title compound (1.38 g, quant.) as a colorless powder.

1H NMR (300 MHz, DMSO-D₆) δ ppm 2.16 (s, 3H) 2.18-2.26 (m, 4H) 3.23-3.31 (m, 4H) 3.59-3.68 (m, 2H) 4.95-5.12 (m, 2H) 5.72-5.87 (m, 1H) 6.63 (t, J=5.44 Hz, 1H).

ESI m/z=206(M+Na).

Reference Example 7

Preparation of
tert-butyl[3-(buta-3-enoylamino)propyl]carbamate

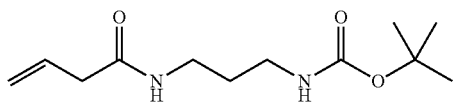

To a chloroform solution (58 mL) of vinyl acetate (500 mg, 5.81 mmol) were added tert-butyl N-(3-aminopropyl)carbamate (2.02 g, 11.6 mmol), 1-hydroxybenzotriazole (0.86 g, 6.39 mmol) and WSC (1.56 g, 8.13 mmol), and the mixture was stirred overnight at room temperature. To the reaction solution was added water and the resulting mixture was extracted with chloroform. The organic layer was washed with a saturated aqueous solution of ammonium chloride and brine, and dried with anhydrous magnesium sulfate. The drying agent was filtered off, and the solvent was evaporated under reduced pressure. Thus obtained residue was purified with silica gel column chromatography (hexane:ethyl acetate=1:1, ethyl acetate) to obtain the title compound (1.32 g, 94%) as a colorless powder.

1H NMR (300 MHz, CHLOROFORM-D) δ ppm 1.44 (s, 9H) 1.52-1.71 (m, 2H) 3.01 (d, J=6.99 Hz, 2H) 3.09-3.23 (m, 2H) 3.30 (q, J=6.37 Hz, 2H) 4.89 (s, 1H) 5.14-5.31 (m, 2H) 5.83-6.06 (m, 1H) 6.21 (s, 1H).

ESI m/z=265(M+Na).

Reference Example 8

Preparation of
N-allyl-N'-(2-hydroxy-1,1-dimethylethyl)urea

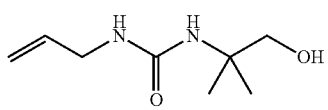

To a chloroform solution (60 mL) of allylamine (1.5 g, 26.3 mmol) were added triethylamine (4.9 mL, 35.5 mmol) and at 4° C. 4-nitrophenyl chloroformate (6.09 g, 30.2 mmol), and the mixture was stirred for an hour. To this reaction solution was added at the same temperature a chloroform solution (3 mL) of 2-amino-2-methylpropanol (2.58 g, 28.9 mmol), and the mixture was stirred overnight at room temperature. The reaction solvent was evaporated under reduced pressure. Thus obtained residue was purified with silica gel column chromatography (ethyl acetate) to obtain the title compound (4.0 g, 88%) as a yellow oily compound.

1H NMR (300 MHz, CHLOROFORM-D) δ ppm 1.26 (s, 6H) 3.55 (s, 2H) 3.71-3.80 (m, 2H) 4.85-5.08 (m, 2H) 5.08-5.24 (m, 2H) 5.77-5.91 (m, 1H).

ESI m/z=195 (M+Na).

Reference Example 9

Preparation of 1-benzyloxy-2-bromo-5-methyl-4-[4-[2-(methoxymethoxy)ethyl]benzyl]benzene

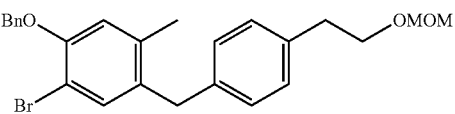

To a tetrahydrofuran solution (1 L) of 1-bromo-4-[2-(methoxymethoxy)ethyl]benzene (50.2 g, 0.205 mol) was added dropwise under nitrogen atmosphere at −78° C. a 2.6 M n-butyllithium solution in hexane (78.8 mL, 0.205 mol), and the mixture was stirred for 15 minutes at the same temperature. Then a tetrahydrofuran solution (150 mL) of 4-benzyloxy-5-bromo-2-methyl benzaldehyde (56.9 g, 0.195 mol) was added dropwise over an hour, and the mixture was stirred for 30 minutes at the same temperature. To the reaction solution was added a saturated aqueous solution of ammonium chloride, and the resulting mixture was extracted with ethyl acetate. The organic layer was washed with a saturated aqueous solution of ammonium chloride and brine, and dried with anhydrous magnesium sulfate. The drying agent was filtered off, and the solvent was evaporated under reduced pressure to obtain [4-(benzyloxy)-5-bromo-2-methylphenyl][4-[2-(methoxymethoxy)ethyl]phenyl]methanol.

Then to a chloroform solution (1 L) of [4-(benzyloxy)-5-bromo-2-methylphenyl][4-[2-(methoxymethoxy)ethyl]phenyl]methanol (102 g) cooled in ice were added Et₃SiH (46.7 mL, 0.293 mol) and BF₃.Et₂O (29.7 mL, 0.243 mol), and the mixture was stirred for 15 minutes at the same temperature. To the reaction solution cooled in ice was added a saturated sodium bicarbonate aqueous solution and warmed to room temperature. The resulting mixture was extracted with ethyl acetate, washed with brine, and then the organic layer was dried with anhydrous magnesium sulfate. The drying agent was filtered off, and the solvent was evaporated under reduced pressure. Thus obtained residue was purified with NH type silica gel column chromatography (hexane:ethyl acetate=19:1 to 9:1) to obtain the title compound (60 g, 68%) as a pale yellow oily compound.

1H NMR (300 MHz, CHLOROFORM-D) δ ppm 2.16 (s, 3H) 2.87 (t, J=6.99 Hz, 2H) 3.28 (s, 3H) 3.75 (t, J=6.99 Hz, 2H) 3.85 (s, 2H) 4.61 (s, 2H) 5.12 (s, 2H) 6.77 (s, 1H) 7.03 (d, J=8.08 Hz, 2H) 7.15 (d, 2H) 7.26 (d, J=3.57 Hz, 1H) 7.30-7.45 (m, 3H) 7.47 (d, 2H).

Reference Example 10

Preparation of (1S)-1,5-anhydro-2,3,4,6-tetra-O-benzyl-1-[2-(benzyloxy)-5-[4-(2-hydroxyethyl)benzyl]-4-methylphenyl]-D-glucitol

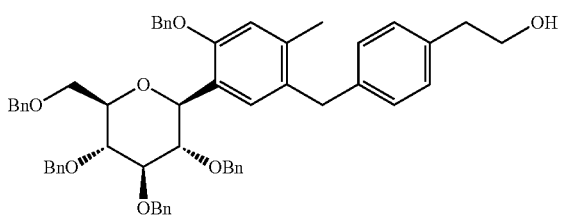

To a tetrahydrofuran solution (150 mL) of 1-benzyloxy-2-bromo-5-methyl-5-[4-[2-(methoxymethoxy)ethyl]benzyl]benzene (13.0 g, 28.5 mmol) was added dropwise under nitrogen atmosphere at −78° C. a 2.6 M n-butyllithium solution in hexane (11.0 mL, 28.5 mmol), and the mixture was stirred for 15 minutes at the same temperature. Then a tetrahydrofuran solution (30 mL) of 2,3,4,6-tetra-O-benzyl-D-glucono-1,5-lactone (14.0 g, 26.0 mmol) was added dropwise, and the mixture was stirred for 15 minutes at the same temperature. To the reaction solution was added a saturated aqueous solution of ammonium chloride, and the resulting mixture was extracted with toluene. The organic layer was washed with a saturated aqueous solution of ammonium chloride and brine, and dried with anhydrous magnesium sulfate. The drying agent was filtered off, and the solvent was evaporated under reduced pressure to obtain 26.0 g of a residue.

The residue was dissolved in acetonitrile (70 mL) and tetrahydrofuran (70 mL). To this solution cooled in ice were added $Et_3SiH$ (2.90 mL, 17.8 mmol) and $BF_3 \cdot Et_2O$ (1.90 mL, 14.9 mmol), and the mixture was stirred for an hour at the same temperature. To the reaction solution cooled in ice was added a saturated sodium bicarbonate aqueous solution, and warmed to room temperature. To this solution was added water (70 mL) and the resulting mixture was extracted with toluene. And then the organic layer was washed with brine, and dried with anhydrous magnesium sulfate. The drying agent was filtered off, and the solvent was evaporated under reduced pressure to obtain 27.0 g of a residue.

The residue was dissolved in isopropyl ether (140 mL). Then to this solution were added 2-propanol (140 mL) and 6 M hydrochloric acid (140 mL), and the reaction mixture was stirred at 80° C. for 2 hours. After the mixture was cooled to room temperature, to the mixture was added water (70 mL). The resulting mixture was extracted with toluene. And then the organic layer was washed with a saturated sodium bicarbonate aqueous solution and brine, and dried with anhydrous magnesium sulfate. The solvent was evaporated under reduced pressure. Thus obtained residue was purified with silica gel column chromatography (hexane:ethyl acetate=9:1 to 7:3) to obtain the title compound (12.0 g, 54%) as a pale yellow oily compound.

1H NMR (300 MHz, CHLOROFORM-D) δ ppm 2.20 (s, 3H) 2.78 (t, J=6.53 Hz, 2H) 3.54-3.64 (m, 1H) 3.68-3.88 (m, 8H) 3.93 (br. s., 2H) 4.00 (d, J=10.72 Hz, 1H) 4.42 (d, J=10.72 Hz, 1H) 4.50 (d, 1H) 4.56-4.66 (m, 2H) 4.81-4.95 (m, 3H) 5.00 (s, 2H) 6.75 (s, 1H) 6.92 (d, J=7.77 Hz, 2H) 7.02 (s, 4H) 7.10-7.35 (m, 22H) 7.36-7.44 (m, 2H).

ESI m/z=873 (M+NH$_4$).

Reference Example 11

Preparation of (1S)-1-[5-[4-(2-aminoethyl)benzyl]-2-(benzyloxy)-4-methylphenyl]-1,5-anhydro-2,3,4,6-tetra-O-benzyl-D-glucitol benzenesulfonic acid

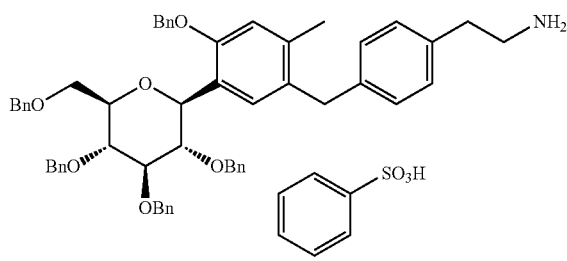

To a tetrahydrofuran solution (140 mL) of (1S)-1,5-anhydro-2,3,4,6-tetra-O-benzyl-1-[2-(benzyloxy)-5-[4-(2-hydroxyethyl)benzyl]-4-methylphenyl]-D-glucitol (12.0 g, 14.0 mmol), triphenyl phosphine (5.51 g, 21.0 mmol), and phthalimide (2.27 g, 15.4 mmol) was added a 40% diisopropyl azodicarboxylate solution (11.1 mL, 21.0 mmol) in toluene under nitrogen atmosphere at 0° C. over 3 minutes. This reaction solution was stirred at room temperature for 30 minutes, and then methanol (70 mL) was added thereto. Then hydrazine monohydrate (6.79 mL, 140 mmol) was added, and the reaction mixture was stirred at 60° C. for 3 hours. After the mixture was cooled to room temperature, a 2 M sodium hydroxide aqueous solution (100 mL) was added thereto, and the resulting mixture was extracted with toluene. The organic layer was washed with a 2 M sodium hydroxide aqueous solution (100 mL) and brine, and dried with anhydrous magnesium sulfate. The solvent was evaporated under reduced pressure to obtain 22.7 g of a residue.

The residue was dissolved in methanol (140 mL), a methanol solution (50 mL) of benzenesulfonic acid monohydrate (2.51 g, 14.0 mmol) was added thereto, and the mixture was stirred for 15 minutes at room temperature. This mixture was evaporated under reduced pressure to obtain an amorphous compound. To thus obtained amorphous compound were added 2-propanol (230 mL) and methanol (90 mL), and the mixture was heated to reflux to dissolve a residue. This mixture was cooled to room temperature and left for 15 hours. Thus obtained crystal was filtered to obtain the colorless title compound (9.89 g, 70%).

1H NMR (300 MHz, CHLOROFORM-D) δ ppm 2.12 (s, 3H) 2.72-2.85 (m, 2H) 2.89-3.05 (m, 2H) 3.54-3.63 (m, 1H) 3.68-3.89 (m, 8H) 3.99 (d, J=10.57 Hz, 1H) 4.39-4.53 (m, 2H) 4.56-4.65 (m, 2H) 4.82-4.94 (m, 3H) 4.98 (s, 2H) 6.72 (s, 1H) 6.79-6.85 (m, 2H) 6.87-6.96 (m, 4H) 7.06-7.44 (m, 25H) 7.75-7.90 (m, 4H).

Reference Example 12

Preparation of (1S)-1-[5-[4-(2-aminoethyl)benzyl]-2-acetoxy-4-methylphenyl]-1,5-anhydro-2,3,4,6-tetra-O-acetyl-D-glucitol

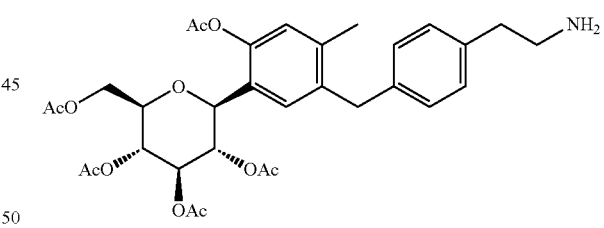

(1) Preparation of (1S)-1-[5-[4-(2-tert-butoxycarbonylaminoethyl)benzyl]-2-acetoxy-4-methylphenyl]-1,5-anhydro-2,3,4,6-tetra-O-acetyl-D-glucitol To a chloroform solution (100 mL) of (1S)-1-[5-[4-(2-aminoethyl)benzyl]-2-(benzyloxy)-4-methylphenyl]-1,5-anhydro-2,3,4,6-tetra-O-benzyl-D-glucitol benzenesulfonic acid (10.7 g, 10.6 mmol) cooled in ice were added under nitrogen atmosphere triethylamine (2.22 mL, 15.9 mmol) and di-tert-butyl-dicarbonate (2.78 g, 12.7 mmol), and the mixture was stirred for 30 minutes at the same temperature. To the reaction solution was added water, and the mixture was warmed to room temperature. Then the resulting mixture was extracted with ethyl acetate. The organic layer was washed with 1 M hydrochloric acid and brine, and dried with anhydrous magnesium sulfate. The drying agent was filtered off, and the solvent was evaporated under reduced pressure to obtain 11.8 g of a residue.

The residue was dissolved in ethyl acetate (50 mL) and methanol (100 mL). And 20% palladium hydroxide (2.50 g) was added thereto, and the mixture was stirred under hydrogen atmosphere at room temperature for 2.5 hours. The reaction solution was filtered through celite, and the solvent was evaporated under reduced pressure to obtain a residue.

This residue was dissolved in pyridine (100 mL). To this solution were added under nitrogen atmosphere acetic anhydride (6.01 mL, 63.6 mmol) and N,N-dimethylaminopyridine, and the mixture was stirred overnight at room temperature. After that, acetic anhydride (4.00 mL, 42.4 mmol) was further added thereto, and the mixture was stirred for 2 hours at the same temperature. To the reaction solution was added water, and the resulting mixture was extracted with ethyl acetate. The organic layer was washed with 3 M hydrochloric acid, a saturated sodium bicarbonate aqueous solution and brine, and dried with anhydrous magnesium sulfate. The drying agent was filtered off, and the solvent was evaporated under reduced pressure to obtain a residue. Thus obtained residue was dissolved by adding ethyl acetate thereto, and hexane was added thereto to obtain a crystal. Thus obtained crystal was filtered to obtain the title compound (5.58 g, 74%) as a colorless powder.

1H NMR (300 MHz, CHLOROFORM-D) δ ppm 1.43 (s, 9H) 1.77 (s, 3H) 2.00 (s, 3H) 2.04 (s, 3H) 2.07 (s, 3H) 2.19 (s, 3H) 2.35 (s, 3H) 2.75 (t, J=6.92 Hz, 2H) 3.28-3.42 (m, 2H) 3.75-3.83 (m, 1H) 3.92 (s, 2H) 4.08 (dd, J=12.43, 2.18 Hz, 1H) 4.30 (dd, J=12.36, 4.74 Hz, 1H) 4.54 (t, 1H) 5.14-5.23 (m, 1H) 5.25-5.37 (m, 2H) 6.87 (s, 1H) 7.02 (d, 2H) 7.10 (d, 2H) 7.16 (s, 1H).

ESI m/z=731 (M+NH$_4$).

(2) Preparation of (1S)-1-[5-[4-(2-aminoethyl)benzyl]-2-acetoxy-4-methylphenyl]-1,5-anhydro-2,3,4,6-tetra-O-acetyl-D-glucitol To a chloroform solution (80 mL) of (1S)-1-[5-[4-(2-tert-butoxycarbonylaminoethyl)benzyl]-2-acetoxy-4-methylphenyl]-1,5-anhydro-2,3,4,6-tetra-O-acetyl-D-glucitol was added trifluoroacetic acid (23 mL), and the mixture was stirred for 1.5 hours at room temperature. The solvent was evaporated under reduced pressure to obtain a residue. Thus obtained residue was diluted with chloroform, and washed with a saturated sodium bicarbonate aqueous solution and brine. This solution was dried with anhydrous magnesium sulfate. The drying agent was filtered off, and the solvent was evaporated under reduced pressure to obtain the title compound (4.67 g, quant.) as a colorless powder.

1H NMR (300 MHz, CHLOROFORM-D) δ ppm 1.77 (s, 3H) 2.00 (s, 3H) 2.04 (s, 3H) 2.07 (s, 3H) 2.19 (s, 3H) 2.35 (s, 3H) 2.67 (t, 2H) 2.85-3.07 (m, 2H) 3.75-3.84 (m, 1H) 3.92 (s, 2H) 4.08 (dd, J=12.36, 2.10 Hz, 1H) 4.30 (dd, J=12.36, 4.59 Hz, 1H) 4.53 (t, 1H) 5.13-5.23 (m, 1H) 5.24-5.36 (m, 2H) 6.86 (s, 1H) 7.02 (d, 2H) 7.11 (d, 2H) 7.17 (s, 1H).

ESI m/z=614 (M+H).

Reference Example 13

Preparation of (1S)-1,5-anhydro-2,3,4,6-tetra-O-benzyl-1-[2-(benzyloxy)-5-(4-hydroxy-2-methylbenzyl)-4-methylphenyl]-D-glucitol

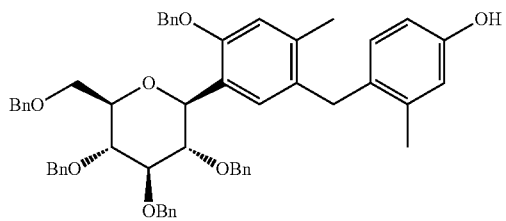

To a tetrahydrofuran solution (15 mL) of 1-bromo-4-methoxymethoxy-2-methyl benzene (0.80 g, 3.46 mmol) was added dropwise under nitrogen atmosphere at −60° C. a 2.6 M hexane solution of n-butyllithium (1.33 mL, 3.46 mmol), and the mixture was stirred for 15 minutes at the same temperature. Then a tetrahydrofuran solution (6 mL) of 2,3,4,6-tetra-O-benzyl-1-C-[2-(benzyloxy)-5-formyl-4-methylphenyl]-D-glucopyranose (1.10 g, 1.44 mmol) was added dropwise, and the mixture was stirred for 15 minutes at the same temperature. To the reaction solution was added a saturated aqueous solution of ammonium chloride, and warmed to room temperature. And then the resulting mixture was extracted with ethyl acetate. The organic layer was washed with brine, and dried with anhydrous magnesium sulfate. The drying agent was filtered off, and the solvent was evaporated under reduced pressure to obtain 1.7 g of an oily matter.

Then the oily matter was dissolved in acetonitrile (10 mL) and chloroform (10 mL). To this solution were added at 4° C. Et$_3$SiH (0.92 mL, 5.76 mmol) and BF$_3$.Et$_2$O (0.46 mL, 3.60 mmol). The reaction solution was stirred for 30 minutes at the same temperature, and the mixture was stirred for 30 minutes at room temperature. To the reaction solution was added a saturated sodium bicarbonate aqueous solution. And the volatiles were evaporated under reduced pressure, and the residue was extracted with ethyl acetate. The organic layer was washed with brine, and dried with anhydrous magnesium sulfate. The drying agent was filtered off, and the solvent was evaporated under reduced pressure. Thus obtained residue was purified with silica gel column chromatography (hexane:ethyl acetate=3:1) to obtain the title compound (420 mg, 35%) as a pale yellow oily compound.

1H NMR (300 MHz, CHLOROFORM-D) δ ppm 2.17 (s, 3H) 2.22 (s, 3H) 3.49-3.59 (m, 1H) 3.63-3.84 (m, 6H) 3.97 (d, J=11.04 Hz, 1H) 4.31-4.50 (m, 3H) 4.52-4.68 (m, 3H) 4.79-4.92 (m, 4H) 5.02 (s, 2H) 6.37 (dd, J=8.32, 2.41 Hz, 1H) 6.55 (d, J=2.49 Hz, 1H) 6.66 (d, J=8.24 Hz, 1H) 6.78 (s, 1H) 6.88-6.97 (m, J=5.21, 4.43 Hz, 2H) 7.01 (s, 1H) 7.10-7.50 (m, 23H).

ESI m/z=858 (M+NH$_4$), 839 (M−H).

Reference Example 14

Preparation of (1S)-1,5-anhydro-2,3,4,6-tetra-O-benzyl-1-[2-(benzyloxy)-5-[4-[2-(1,3-dioxo-1,3-dihydro-2H-isoindole-2-yl)ethoxy]-2-methylbenzyl]-4-methylphenyl]-D-glucitol

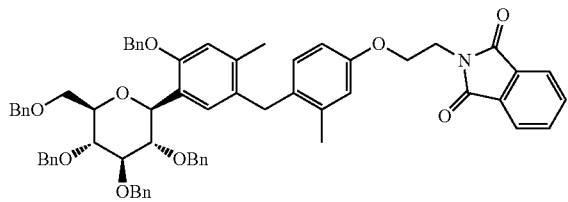

To a N,N-dimethylformamide solution (5.0 mL) of (1S)-1,5-anhydro-2,3,4,6-tetra-O-benzyl-1-[2-(benzyloxy)-5-(4-hydroxy-2-methylbenzyl)-4-methylphenyl]-D-glucitol (340 mg, 0.40 mmol) and N-(2-bromoethyl)phthalimide (1.02 g, 4.0 mmol) were added potassium carbonate (553 mg, 4.0 mmol) and n-Bu$_4$NI (14 mg, 0.038 mmol). The reaction mixture was stirred at 80° C. for 3.5 hours. After the mixture was cooled to room temperature, water was added thereto, and the resulting mixture was extracted with ethyl acetate. The organic layer was washed with brine, and dried with anhydrous magnesium sulfate. The drying agent was filtered off, and the solvent was evaporated under reduced pressure to obtain a residue. Thus obtained residue was purified with silica gel column chromatography (hexane:ethyl acetate=3:1) to obtain the title compound (60 mg, 15%) as a pale yellow oily compound.

1H NMR (300 MHz, CHLOROFORM-D) δ ppm 2.17 (s, 3H) 2.18 (s, 3H) 3.49-3.60 (m, 1H) 3.63-3.85 (m, 6H) 3.89-4.19 (m, 5H) 4.34-4.52 (m, 3H) 4.53-4.65 (m, 3H) 4.75-4.93 (m, 3H) 5.01 (s, 2H) 6.44 (dd, J=8.55, 2.64 Hz, 1H) 6.60-6.71 (m, 2H) 6.77 (s, 1H) 6.88-6.97 (m, 2H) 7.05 (s, 1H) 7.13-7.45 (m, 23H) 7.66-7.72 (m, 2H) 7.80-7.88 (m, 2H).

Reference Example 15

Preparation of (1S)-1-[5-[4-(2-aminoethoxy)-2-methylbenzyl]-2-(benzyloxy)-4-methylphenyl]-1,5-anhydro-2,3,4,6-tetra-O-benzyl-D-glucitol

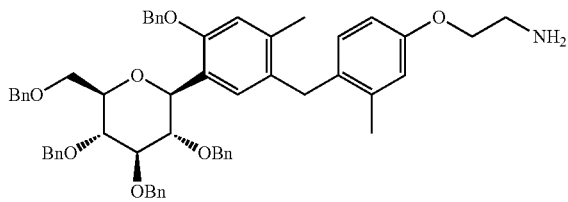

To a tetrahydrofuran (0.8 mL) and methanol (0.2 mL) solution of (1S)-1,5-anhydro-2,3,4,6-tetra-O-benzyl-1-[2-(benzyloxy)-5-[4-[2-(1,3-dioxo-1,3-dihydro-2H-isoindole-2-yl)ethoxy]-2-methylbenzyl]-4-methylphenyl]-D-glucitol (60 mg, 0.059 mmol) was added hydrazine monohydrate (30 mg, 0.59 mmol), and the reaction mixture was stirred at 65° C. for an hour. After the mixture was cooled to room temperature, a 2 M aqueous solution of sodium hydroxide was added thereto, and the resulting mixture was extracted with ethyl acetate. The organic layer was washed with brine, and dried with anhydrous magnesium sulfate. The solvent was evaporated under reduced pressure to obtain the title compound quantitatively.

1H NMR (300 MHz, CHLOROFORM-D) δ ppm 2.21 (s, 3H) 2.22 (s, 3H) 3.03 (t, J=4.74 Hz, 2H) 3.50-3.62 (m, 1H) 3.65-3.83 (m, 6H) 3.88 (t, J=4.74 Hz, 2H) 3.98 (d, J=10.88 Hz, 1H) 4.34-4.51 (m, 3H) 4.55-4.65 (m, 3H) 4.77-4.93 (m, 3H) 5.02 (s, 2H) 6.43-6.51 (m, 1H) 6.66-6.72 (m, 2H) 6.78 (s, 1H) 6.91-6.98 (m, 2H) 7.06 (s, 1H) 7.11-7.45 (m, 23H).

In addition, the compound (I) in which R$^3$ represents a methoxy group or a fluorine atom can be synthesized by using 1-bromo-2-methoxy-4-methoxymethoxy benzene or 1-bromo-2-fluoro-4-methoxymethoxy benzene as a starting material according to the method as with Reference Examples 13 to 15.

Reference Example 16

Preparation of 4-(benzyloxy)-5-bromo-2-chlorobenzaldehyde

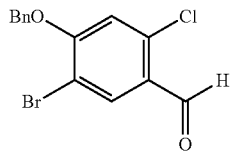

To a chloroform solution (300 mL) of 2-chloro-4-hydroxy benzonitrile (14.0 g, 91.2 mmol) was added dropwise under nitrogen atmosphere at −50° C. a 0.95 M diisobutyl aluminum hydride solution in hexane (307 mL, 291 mmol), and the mixture was stirred for 1.5 hours at the same temperature. The temperature of the solution is increased to room temperature, and the mixture was stirred further for 3 hours. Subsequently, the reaction solution was cooled in ice, and methanol was added dropwise thereto. To the reaction solution was added 3 M hydrochloric acid, and the resulting mixture was extracted with ethyl acetate. The organic layer was washed with a saturated sodium bicarbonate aqueous solution and brine, and dried with anhydrous magnesium sulfate. The drying agent was filtered off, and the solvent was evaporated under reduced pressure to obtain 7.25 g of a residue.

The residue was dissolved in methanol (140 mL). To this solution cooled in ice under nitrogen atmosphere was added pyridine hydrobromide perbromide (16.3 g, 50.9 mmol), and the mixture was stirred for 4 hours. To the reaction solution was added a 20% solution of Na$_2$SO$_3$, and the resulting mixture was extracted with ethyl acetate. The organic layer was washed with 3 M hydrochloric acid, a saturated sodium bicarbonate aqueous solution and brine, and dried with anhydrous magnesium sulfate. The drying agent was filtered off, and the solvent was evaporated under reduced pressure. Thus obtained residue was purified with silica gel column chromatography (hexane:ethyl acetate=3:1) to obtain 6.17 g of a colorless powder.

This powder was dissolved in acetone (260 mL). To this solution were added under nitrogen atmosphere benzyl bromide (3.45 mL, 28.8 mmol) and potassium carbonate (4.70 g, 34.1 mmol), and the mixture was stirred at 50° C. for 4.5 hours. The reaction solution was cooled to room temperature, and then filtered through celite. The solvent was evaporated under reduced pressure. Thus obtained residue was purified with silica gel column chromatography (hexane:ethyl acetate=10:1) to obtain the title compound (2.02 g, 6.9%) as a colorless powder.

1H NMR (300 MHz, CHLOROFORM-D) δ ppm 5.23 (s, 2H) 6.97 (s, 1H) 7.32-7.50 (m, 5H) 8.15 (s, 1H) 10.27 (s, 1H).

ESI m/z=325 (M+H).

Reference Example 17

Preparation of [4-(benzyloxy)-5-bromo-2-chlorophenyl][4-[2-(methoxymethoxy)ethyl]phenyl]methanol

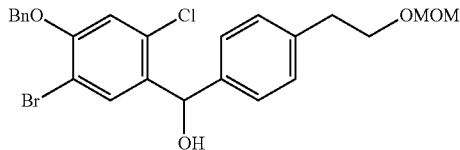

To a tetrahydrofuran solution (6 mL) of 1-bromo-4-[2-(methoxymethoxy)ethyl]benzene (1.52 g, 6.20 mmol) was added dropwise under nitrogen atmosphere at −78° C. a 2.6 M hexane solution of n-butyllithium (2.38 mL, 6.20 mmol), and the mixture was stirred for 10 minutes at the same temperature. Then a tetrahydrofuran solution (6 mL) of 4-(benzyloxy)-5-bromo-2-chlorobenzaldehyde (2.02 g, 6.20 mmol) was added dropwise over 10 minutes, and the mixture was stirred for 30 minutes at the same temperature. To the reaction solution was added a saturated aqueous solution of ammonium chloride, and the resulting mixture was extracted with ethyl acetate. The organic layer was washed with a saturated aqueous solution of ammonium chloride and brine, and dried with anhydrous magnesium sulfate. The drying agent was filtered off, and the solvent was evaporated under reduced pressure. Thus obtained residue was purified with silica gel column chromatography (hexane:ethyl acetate=10:1) to obtain the title compound (750 mg, 25%) as a colorless oily compound.

1H NMR (300 MHz, CHLOROFORM-D) δ ppm 2.24 (d, J=3.57 Hz, 1H) 2.89 (t, J=6.92 Hz, 2H) 3.27 (s, 3H) 3.75 (t, J=6.84 Hz, 2H) 4.60 (s, 2H) 5.12 (s, 2H) 6.09 (d, J=3.57 Hz, 1H) 6.91 (s, 1H) 7.15-7.51 (m, 9H) 7.80 (s, 1H).

ESI m/z=508 (M+NH$_4$).

Reference Example 18

Preparation of 1-(benzyloxy)-2-bromo-5-chloro-4-[4-[2-(methoxymethoxy)ethyl]benzyl]benzene

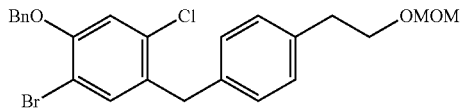

To a chloroform solution (8 mL) of [4-(benzyloxy)-5-bromo-2-chlorophenyl][4-[2-(methoxymethoxy)ethyl]phenyl]methanol (750 mg, 1.53 mmol) cooled in ice were added Et$_3$SiH (367 μL, 2.30 mmol) and BF$_3$.Et$_2$O (232 μL, 1.83 mmol), and the mixture was stirred for an hour at the same temperature. To this solution cooled in ice was added a saturated sodium bicarbonate aqueous solution, and warmed to room temperature. The resulting mixture was extracted with ethyl acetate, washed with brine, and dried with anhydrous magnesium sulfate. The drying agent was filtered off, and the solvent was evaporated under reduced pressure. Thus obtained residue was purified with silica gel column chromatography (hexane:ethyl acetate=4:1) to obtain the title compound (290 mg, 40%) as a colorless oily compound.

1H NMR (300 MHz, CHLOROFORM-D) δ ppm 2.88 (t, J=7.15 Hz, 2H) 3.28 (s, 3H) 3.75 (t, J=6.99 Hz, 2H) 3.97 (s, 2H) 4.61 (s, 2H) 5.12 (s, 2H) 6.96 (s, 1H) 7.10 (d, 2H) 7.17 (d, 2H) 7.28-7.50 (m, 6H).

ESI m/z=492 (M+NH$_4$).

Reference Example 19

Preparation of 2,3,4,6-tetra-O-benzyl-1-C-[2-(benzyloxy)-4-chloro-5-[4-[2-(methoxymethoxy)ethyl]benzyl]phenyl]-D-glucopyranose

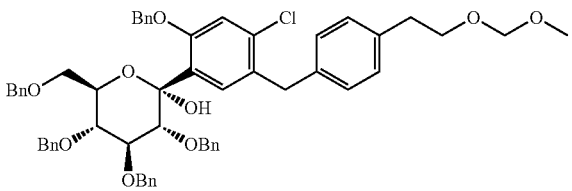

To a tetrahydrofuran solution (3 mL) of 1-(benzyloxy)-2-bromo-5-chloro-4-[4-[2-(methoxymethoxy)ethyl]benzyl]benzene (290 mg, 0.609 mmol) was added dropwise under nitrogen atmosphere at −78° C. a 2.6 M hexane solution of n-butyllithium (234 μL, 0.609 mmol), and the mixture was stirred for 5 minutes at the same temperature. Then a tetrahydrofuran solution (3 mL) of 2,3,4,6-tetra-O-benzyl-D-glucono-1,5-lactone (328 mg, 0.609 mmol) was added dropwise, and the mixture was stirred for an hour at the same temperature. To the reaction solution was added a saturated aqueous solution of ammonium chloride, and the resulting mixture was extracted with ethyl acetate. The organic layer was washed with a saturated aqueous solution of ammonium chloride and brine, and dried with anhydrous magnesium sulfate. The drying agent was filtered off, and the solvent was evaporated under reduced pressure. Thus obtained residue was purified with silica gel column chromatography (hexane: ethyl acetate=3:1) to obtain the title compound (124 mg, 22%) as a colorless oily compound.

1H NMR (300 MHz, CHLOROFORM-D) δ ppm 2.85 (t, J=6.99 Hz, 2H) 3.28 (s, 3H) 3.60 (s, 5H) 3.94-4.02 (m, 3H) 4.04-4.15 (m, 3H) 4.43-4.61 (m, 6H) 4.71-4.97 (m, 5H) 6.89 (s, 3H) 7.37 (s, 27H) 7.50 (s, 1H).

ESI m/z=952 (M+NH$_4$).

Reference Example 20

Preparation of (1S)-1,5-anhydro-2,3,4,6-tetra-O-benzyl-1-[2-(benzyloxy)-4-chloro-5-[4-(2-hydroxyethyl)benzyl]phenyl]-D-glucitol

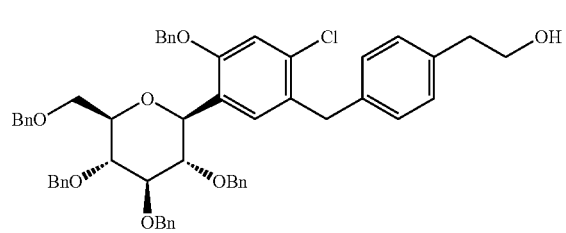

To an acetonitrile (0.5 mL) and tetrahydrofuran (0.5 mL) solution of 2,3,4,6-tetra-O-benzyl-1-C-[2-(benzyloxy)-4-chloro-5-[4-[2-(methoxymethoxy)ethyl]benzyl]phenyl]-D- glucopyranose (124 mg, 0.133 mmol) cooled in ice were added Et$_3$SiH (63.6 μL, 0.400 mmol) and BF$_3$.Et$_2$O (40.4 μL, 0.320 mmol), and the mixture was stirred for 1.5 hours at the same temperature and the mixture was stirred for 4.5 hours at room temperature. To the reaction solution cooled in ice was added a saturated sodium bicarbonate aqueous solution and the resulting mixture was extracted with ethyl acetate. The organic layer was washed with brine, and dried with anhydrous magnesium sulfate. The drying agent was filtered off, and the solvent was evaporated under reduced pressure to obtain 119 mg of a residue.

The residue was dissolved in isopropyl ether (0.7 mL). Then to this solution were added 2-propanol (0.7 mL) and 6 M hydrochloric acid (0.7 mL), and the reaction mixture was stirred at 80° C. for 3 hours. After the mixture was cooled to room temperature, to the mixture was added water, and the resulting mixture was extracted with ethyl acetate. And then the organic layer was washed with a saturated sodium bicarbonate aqueous solution and brine, and dried with anhydrous magnesium sulfate. The solvent was evaporated under reduced pressure. Thus obtained residue was purified with silica gel column chromatography (hexane:ethyl acetate=7:3) to obtain the title compound (79.1 mg, 68%) as a colorless oily compound.

1H NMR (600 MHz, CHLOROFORM-D) δ ppm 2.77 (t, J=6.42 Hz, 2H) 3.52-3.60 (m, 1H) 3.64-3.82 (m, 7H) 3.92-3.99 (m, 3H) 4.03 (d, 1H) 4.41-4.51 (m, 2H) 4.54-4.64 (m, 2H) 4.82-4.89 (m, 3H) 4.91-4.97 (m, 2H) 6.86 (d, J=7.34 Hz, 2H) 6.90 (s, 1H) 7.02-7.06 (m, 2H) 7.06-7.10 (m, 2H) 7.13 (t, J=7.34 Hz, 2H) 7.15-7.20 (m, 3H) 7.20-7.33 (m, 17H) 7.36 (d, J=7.79 Hz, 2H).

ESI m/z=892 (M+NH$_4$).

Reference Example 21

Preparation of (1S)-1-[5-[4-(2-aminoethyl)benzyl]-2-(benzyloxy)-4-chlorophenyl]-1,5-anhydro-2,3,4,6-tetra-O-benzyl-D-glucitol

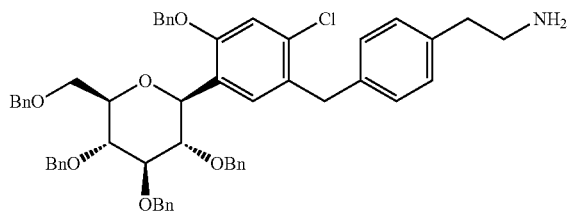

To a tetrahydrofuran solution (2.0 mL) of (1S)-1,5-anhydro-2,3,4,6-tetra-O-benzyl-1-[2-(benzyloxy)-4-chloro-5-[4-(2-hydroxyethyl)benzyl]phenyl]-D-glucitol (79.0 mg, 0.090 mmol), triphenyl phosphine (53.1 mg, 0.203 mmol), and phthalimide (23.9 mg, 0.162 mmol) cooled in ice was added a 40% diisopropyl azodicarboxylate solution in toluene (386 μL, 0.203 mmol) under nitrogen atmosphere. After the reaction solution was stirred at room temperature for 1.5 hours, methanol (1 mL) was added thereto. Then hydrazine monohydrate (43.7 μL, 0.90 mmol) was added, and the reaction mixture was stirred at 60° C. for 3 hours. After the mixture was cooled to room temperature, a 2 M sodium hydroxide aqueous solution was added thereto, and the resulting mixture was extracted with ethyl acetate. The organic layer was washed with brine, and dried with anhydrous magnesium sulfate. The solvent was evaporated under reduced pressure.

Thus obtained residue was purified with silica gel column chromatography (chloroform:methanol=9:1) to obtain the title compound (39.2 mg, 50%) as a colorless oily compound.

1H NMR (300 MHz, CHLOROFORM-D) δ ppm 2.68 (t, 2H) 2.83-2.96 (m, 2H) 3.52-3.61 (m, 1H) 3.62-3.86 (m, 5H) 3.99 (t, J=10.57 Hz, 3H) 4.41-4.67 (m, 5H) 4.81-4.92 (m, 3H) 4.95 (s, 2H) 6.88 (d, J=5.60 Hz, 3H) 6.97-7.43 (m, 28H).

ESI m/z=874 (M+H).

Reference Example 22

Preparation of 5-bromo-2-chlorobenzaldehyde

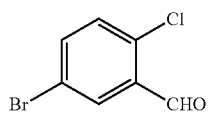

To a suspension of 5-bromo-2-chlorobenzoic acid (18.5 g, 78.5 mmol) in chloroform (157 mL) was added N,N-dimethylformamide (0.5 mL), and oxalylchloride (8.1 mL, 94.2 mmol) was added dropwise thereto at room temperature. This reaction solution was stirred for 30 minutes, and then concentrated under reduced pressure. Thus obtained residue was dissolved in chloroform (157 mL), and added dropwise at 0° C. to a suspension of N,O-dimethylhydroxylamine hydrochloride (9.19 g, 94.2 mmol) and triethylamine (26.3 mL, 188 mmol) in chloroform. This reaction solution was stirred for 30 minutes at the same temperature, and then washed with water, a saturated sodium bicarbonate aqueous solution and brine. And an organic layer was dried with anhydrous magnesium sulfate. The drying agent was filtered off, and the solvent was evaporated under reduced pressure to obtain 24.0 g of a residue.

Thus obtained residue was dissolved in tetrahydrofuran (157 mL), and lithium aluminum hydride (1.19 g, 29.0 mmol) was gradually added thereto at 0° C. After this reaction solution was cooled to 0° C., 2 M hydrochloric acid was gradually added thereto, and the mixture was stirred at room temperature for 30 minutes. The organic layer was washed with a saturated sodium bicarbonate aqueous solution and then brine, and dried with anhydrous magnesium sulfate. The drying agent was filtered off, and the solvent was evaporated under reduced pressure. Thus obtained residue was recrystallized from a mixed solution of ethyl acetate:hexane (1:9) to obtain the title compound (11.3 g, 65%) as colorless crystals.

1H NMR (300 MHz, CHLOROFORM-D) δ ppm 7.35 (d, J=8.47 Hz, 1H) 7.65 (dd, J=8.47, 2.56 Hz, 1H) 8.04 (d, J=2.56 Hz, 1H) 10.41 (s, 1H).

Reference Example 23

Preparation of (5-bromo-2-chlorophenyl)[4-[2-(methoxymethoxy)ethyl]phenyl]methanol

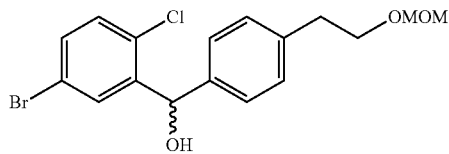

By conducting a method as with Reference Example 17 in which 5-bromo-2-chlorobenzaldehyde was used instead of 4-(benzyloxy)-5-bromo-2-chlorobenzaldehyde, the title compound (4.55 g, 63%) was obtained as a colorless oily compound.

1H NMR (300 MHz, CHLOROFORM-D) δ ppm 2.89 (t, J=6.99 Hz, 2H) 3.26 (s, 3H) 3.74 (t, J=6.99 Hz, 2H) 4.59 (s, 2H) 6.11 (s, 1H) 7.13-7.39 (m, 6H) 7.82-7.84 (m, 1H).

Reference Example 24

Preparation of 5-bromo-2-chloro-4-[4-[2-(methoxymethoxy)ethyl]benzyl]benzene

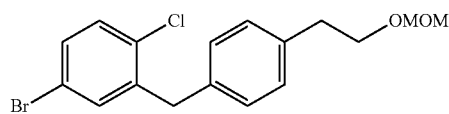

To a chloroform solution (1.4 mL) of (5-bromo-2-chlorophenyl)[4-[2-(methoxymethoxy)ethyl]phenyl]methanol (0.265 g, 0.687 mmol) was added triethylamine (105 µL, 0.756 mmol). And methanesulfonylchloride (58.5 µL, 0.756 mmol) was added dropwise thereto at 0° C. and the mixture was stirred for 2 hours at the same temperature. To the reaction solution was added water, and the resulting mixture was extracted twice with ethyl acetate. The organic layer was washed with brine, and the organic layer was dried with anhydrous magnesium sulfate. The drying agent was filtered off, and the solvent was evaporated under reduced pressure to obtain a residue.

To a chloroform solution (3.4 mL) of thus obtained residue and Et₃SiH (165 µL, 1.03 mmol) was added BF₃.Et₂O (104 µL, 0.824 mmol) at 0° C., and the mixture was stirred for an hour at the same temperature. This reaction solution was washed with a saturated sodium bicarbonate aqueous solution (twice) and then brine, and the organic layer was dried with anhydrous magnesium sulfate. The drying agent was filtered off, and the solvent was evaporated under reduced pressure. Thus obtained residue was purified with silica gel column chromatography (hexane:ethyl acetate=9:1) to obtain a pale yellow crude product (41 mg).

ESI m/z=386 (M+NH₄).

Reference Example 25

Preparation of 2,3,4,6-tetra-O-benzyl-1-C-[4-chloro-3-[4-[2-(methoxymethoxy)ethyl]benzyl]phenyl]-D-glucopyranose

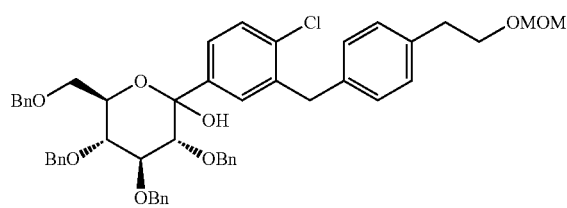

A crude product of the title compound (1.07 g) was obtained as a colorless oily matter according to the method as with Reference Example 19 in which 5-bromo-2-chloro-4-[4-[2-(methoxymethoxy)ethyl]benzyl]benzene was used instead of 1-(benzyloxy)-2-bromo-5-chloro-4-[4-[2-(methoxymethoxy)ethyl]benzyl]benzene.

ESI m/z=846 (M+NH₄).

Reference Example 26

Preparation of (1S)-1,5-anhydro-2,3,4,6-tetra-O-benzyl-1-[4-chloro-3-[4-(2-hydroxyethyl)benzyl]phenyl]-D-glucitol

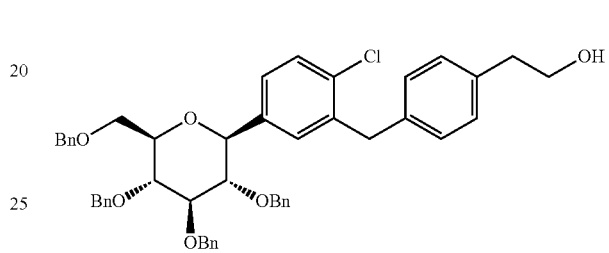

A crude product of the title compound (0.262 g) was obtained as a colorless oily matter according to the method as with Reference Example 20 in which 2,3,4,6-tetra-O-benzyl-1-C-[4-chloro-3-[4-[2-(methoxymethoxy)ethyl]benzyl]phenyl]-D-glucopyranose was used instead of 2,3,4,6-tetra-O-benzyl-1-C-[2-(benzyloxy)-4-chloro-5-[4-[2-(methoxymethoxy)ethyl]benzyl]phenyl]-D-glucopyranose ESI m/z=786 (M+NH₄).

Reference Example 27

Preparation of (1S)-1-[3-[4-(2-aminoethyl)benzyl]-4-chlorophenyl]-1,5-anhydro-2,3,4,6-tetra-O-benzyl-D-glucitol

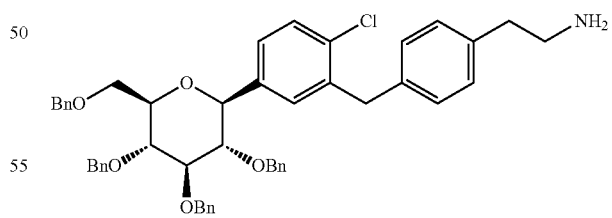

A crude product of the title compound (0.230 g) was obtained as a pale yellow oily matter according to the method as with Reference Example 21 in which (1S)-1,5-anhydro-2,3,4,6-tetra-O-benzyl-1-[4-chloro-3-[4-(2-hydroxyethyl)benzyl]phenyl]-D-glucitol was used instead of (1S)-1,5-anhydro-2,3,4,6-tetra-O-benzyl-1-[2-(benzyloxy)-4-chloro-5-[4-(2-hydroxyethyl)benzyl]phenyl]-D-glucitol.

Reference Example 28

Preparation of (1S)-1,5-anhydro-2,3,4,6-tetra-O-benzyl-1-[2-(benzyloxy)-5-(4-bromobenzyl)-4-methylphenyl]-D-galactitol

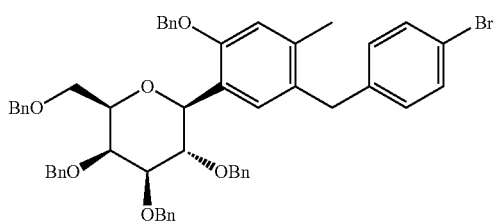

The title compound was synthesized according to the method as with Reference Example 2 in which 2,3,4,6-tetra-O-benzyl-D-galactono-1,5-lactone was used instead of 2,3,4,6-tetra-O-benzyl-D-glucono-1,5-lactone.

1H NMR (300 MHz, CHLOROFORM-D) δ ppm 2.12 (s, 3H) 3.32-3.81 (m, 4H) 3.86 (s, 2H) 4.07 (t, J=10.72 Hz, 3H) 4.32-4.47 (m, 2H) 4.49-4.80 (m, 5H) 4.93-5.07 (m, 3H) 6.72 (s, 1H) 6.80-7.01 (m, 4H) 7.06-7.46 (m, 26H). ESI m/z=911 (M+Na). 913(M+2+Na).

Reference Example 29

Preparation of (1S)-1,5-anhydro-2,3,4,6-tetra-O-benzyl-1-(2-(benzyloxy)-5-[4-[(1E)-3-carboxyprop-1-en-1-yl]benzyl]-4-methylphenyl)-D-galactitol

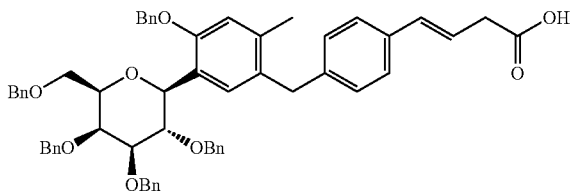

The title compound (377 mg, 41%) was obtained as a pale yellow amorphous compound from (1S)-1,5-anhydro-2,3,4,6-tetra-O-benzyl-1-[2-(benzyloxy)-5-(4-bromobenzyl)-4-methylphenyl]-D-galactitol (918 mg, 1.03 mmol) according to the method as with Reference Example 3.

EXAMPLES

The compounds of the present invention will be further described in more detail in the following examples and test examples, which are not intended to limit the scope of the invention.

Example 1

Preparation of (1S)-1,5-anhydro-1-[2-hydroxy-5-[4-[4-[(2-hydroxy-1,1-dimethylethyl)amino]-4-oxobutyl]benzyl]-4-methylphenyl]-D-glucitol

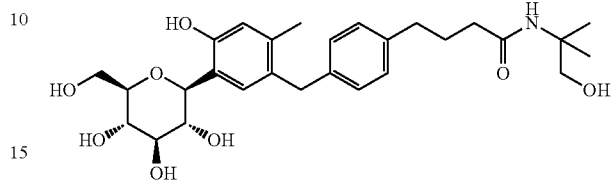

(1) Preparation of (1S)-1,5-anhydro-2,3,4,6-tetra-O-benzyl-1-[2-(benzyloxy)-5-[4-[(1E)-4-[(2-hydroxy-1,1-dimethylethyl)amino]-4-oxobut-1-en-1-yl]benzyl]-4-methylphenyl]-D-glucitol To a chloroform solution (2.2 mL) of (1S)-1,5-anhydro-2,3,4,6-tetra-O-benzyl-1-[2-(benzyloxy)-5-[4-[(1E)-3-carboxyprop-1-en-1-yl]benzyl]-4-methylphenyl]-D-glucitol (200 mg, 0.223 mmol) were added 2-amino-2-methyl-1-propanol (40 mg, 0.446 mmol), 1-hydroxy benzotriazole (33 mg, 0.245 mmol) and WSC (60 mg, 0.312 mmol), and the mixture was stirred overnight at room temperature. To the reaction solution was added water, and the resulting mixture was extracted with chloroform. The organic layer was washed with brine, and dried with anhydrous magnesium sulfate. The drying agent was filtered off, and the solvent was evaporated under reduced pressure. Thus obtained residue was purified with silica gel column chromatography (hexane:ethyl acetate=5:1 to 1:2) to obtain the title compound (120 mg, 56%) as an orange-yellow oily compound.

1H NMR (300 MHz, CHLOROFORM-D) δ ppm 1.26 (s, 6H) 2.19 (s, 3H) 3.11 (d, J=7.46 Hz, 2H) 3.54-3.63 (m, 3H) 3.67-3.85 (m, 5H) 3.89-4.05 (m, 3H) 4.40-4.68 (m, 4H) 4.81-4.95 (m, 3H) 5.00 (s, 2H) 5.60 (s, 1H) 6.08-6.21 (m, 1H) 6.45 (d, J=15.54 Hz, 1H) 6.75 (s, 1H) 6.89-6.97 (m, 2H) 7.03 (d, J=7.93 Hz, 2H) 7.11-7.45 (m, 26H).

ESI m/z=988.5 (M+Na).

(2) Preparation of (1S)-1,5-anhydro-1-[2-hydroxy-5-[4-[4-[(2-hydroxy-1,1-dimethylethyl)amino]-4-oxobutyl]benzyl]-4-methylphenyl]-D-glucitol To a methanol solution (1.2 mL) of (1S)-1,5-anhydro-2,3,4,6-tetra-O-benzyl-1-[2-(benzyloxy)-5-[4-[(1E)-4-[(2-hydroxy-1,1-dimethylethyl)amino]-4-oxobut-1-en-1-yl]benzyl]-4-methylphenyl]-D-glucitol (120 mg, 0.124 mmol) was added 10% palladium-activated carbon (22 mg), and the mixture was stirred overnight under a hydrogen atmosphere at room temperature. The reaction solution was filtered through celite, and evaporated under reduced pressure to obtain a residue. Thus obtained residue was purified with silica gel column chromatography (chloroform:methanol=20:1 to 5:1) to obtain the title compound (58 mg, 90%) as a colorless powder. NMR data and MS data of the compound are shown in Table 1.

Example 2

Preparation of (1S)-1,5-anhydro-1-[2-hydroxy-5-[4-[4-[[2-hydroxy-1-(hydroxymethyl)-1-methylethyl]amino]-4-oxobutyl]benzyl]-4-methylphenyl]-D-glucitol

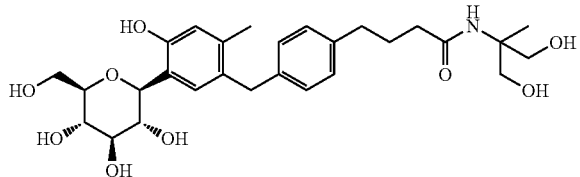

(1) Preparation of (1S)-1,5-anhydro-2,3,4,6-tetra-O-benzyl-1-[2-(benzyloxy)-5-[4-[(1E)-4-[[2-hydroxy-1-(hydroxymethyl)-1-methylethyl]amino]-4-oxobut-1-en-1-yl]benzyl]-4-methylphenyl]-D-glucitol The title compound (91 mg, 44%) was obtained as a colorless oily compound according to the method as with Example 1 (1) in which 2-amino-2-methyl-1,3-propanediol was used instead of 2-amino-2-methyl-1-propanol.

1H NMR (300 MHz, CHLOROFORM-D) δ ppm 1.19 (s, 3H) 2.20 (s, 3H) 3.15 (d, J=6.06 Hz, 2H) 3.49-3.83 (m, 10H) 3.87-4.04 (m, 3H) 4.37-4.67 (m, 4H) 4.80-4.94 (m, 3H) 5.00 (s, 2H) 6.00-6.23 (m, 2H) 6.40-6.52 (m, 1H) 6.75 (s, 1H) 6.93 (dd, J=7.38, 1.94 Hz, 2H) 7.03 (d, J=8.24 Hz, 2H) 7.11-7.35 (m, 24H) 7.35-7.46 (m, 2H).

ESI m/z=1004.5 (M+Na).

(2) Preparation of (1S)-1,5-anhydro-1-[2-hydroxy-5-[4-[4-[[2-hydroxy-1-(hydroxymethyl)-1-methylethyl]amino]-4-oxobutyl]benzyl]-4-methylphenyl]-D-glucitol To a methanol solution (1 mL) of (1S)-1,5-anhydro-2,3,4,6-tetra-O-benzyl-1-[2-(benzyloxy)-5-[4-[(1E)-4-[[2-hydroxy-1-(hydroxymethyl)-1-methylethyl]amino]-4-oxobut-1-en-1-yl]benzyl]-4-methylphenyl]-D-glucitol (91 mg, 0.0926 mmol) was added 10% palladium-activated carbon (16 mg), and the mixture was stirred overnight under a hydrogen atmosphere at room temperature. The reaction solution was filtered through celite, and evaporated under reduced pressure to obtain a residue. Thus obtained residue was dissolved in methanol (1 mL). And 20% palladium hydroxide (91 mg) was added thereto, and the mixture was stirred under hydrogen atmosphere at room temperature for 2 days. The reaction solution was filtered through celite, and evaporated under reduced pressure to obtain a residue. Thus obtained residue was purified with silica gel column chromatography (chloroform:methanol=5:1) to obtain the title compound (32 mg, 65%) as a colorless powder. NMR data and MS data of the compound are shown in Table 1.

Example 3

Preparation of (1S)-1,5-anhydro-1-[2-hydroxy-5-[4-[4-[[2-hydroxy-1,1-bis(hydroxymethyl)ethyl]amino]-4-oxobutyl]benzyl]-4-methylphenyl]-D-glucitol

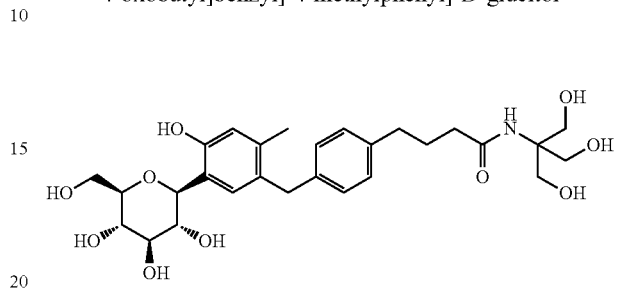

(1) Preparation of (1S)-1,5-anhydro-2,3,4,6-tetra-O-benzyl-1-[2-(benzyloxy)-5-[4-[(1E)-4-[[2-hydroxy-1,1-bis(hydroxymethyl)ethyl]amino]-4-oxobut-1-en-1-yl]benzyl]-4-methylphenyl]-D-glucitol The title compound (151 mg, 55%) was obtained as a pale yellow powder according to the method as with Example 1 (1) in which tris(hydroxymethyl)aminomethane was used instead of 2-amino-2-methyl-1-propanol.

1H NMR (300 MHz, CHLOROFORM-D) δ ppm 2.22 (s, 3H) 3.18 (dd, J=7.15, 1.09 Hz, 2H) 3.43-3.81 (m, 12H) 3.87-4.02 (m, 3H) 4.36-4.67 (m, 4H) 4.80-4.93 (m, 3H) 5.00 (s, 2H) 6.10-6.22 (m, 1H) 6.47 (d, J=15.85 Hz, 1H) 6.68 (s, 1H) 6.75 (s, 1H) 6.93 (d, J=5.91 Hz, 2H) 7.03 (d, J=8.08 Hz, 2H) 7.10-7.35 (m, 24H) 7.36-7.44 (m, 2H).

ESI m/z=998.5 (M+H).

(2) Preparation of (1S)-1,5-anhydro-1-[2-hydroxy-5-[4-[4-[[2-hydroxy-1,1-bis(hydroxymethyl)ethyl]amino]-4-oxobutyl]benzyl]-4-methylphenyl]-D-glucitol The title compound (60 mg, 76%) was obtained as a colorless powder according to the method as with Example 2 (2). NMR data and MS data of the compound are shown in Table 1.

Example 4

Preparation of (1S)-1-[5-[4-[4-[(2-amino-1,1-dimethyl-2-oxoethyl)amino]-4-oxobutyl]benzyl]-2-hydroxy-4-methylphenyl]-1,5-anhydro-D-glucitol

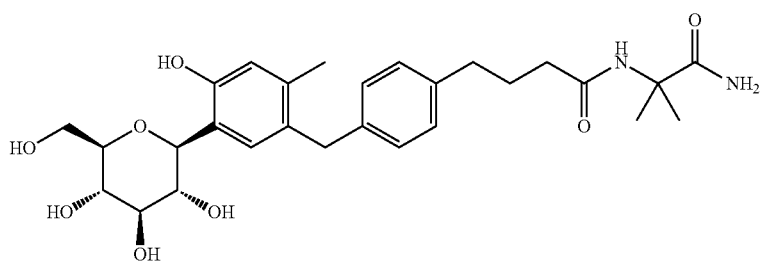

(1) Preparation of (1S)-1-[5-[4-[(1E)-4-[(2-amino-1, 1-dimethyl-2-oxoethyl)amino]-4-oxobut-1-en-1-yl]benzyl]-2-(benzyloxy)-4-methylphenyl]-1,5-anhydro-2,3,4,6-tetra-O-benzyl-D-glucitol The title compound (75 mg, 42%) was obtained as a pale yellow powder according to the method as with Example 1 (1) in which 2-amino-2-methylpropionamide was used instead of 2-amino-2-methyl-1-propanol.

1H NMR (300 MHz, CHLOROFORM-D) δ ppm 1.55 (s, 3H) 1.57 (s, 3H) 2.19 (s, 3H) 3.12 (dd, J=7.38, 1.17 Hz, 2H) 3.53-3.87 (m, 6H) 3.89-4.05 (m, 3H) 4.39-4.54 (m, 2H) 4.57-4.66 (m, 2H) 4.81-4.94 (m, 3H) 5.00 (s, 2H) 6.08-6.23 (m, 2H) 6.46 (d, J=16.01 Hz, 1H) 6.75 (s, 1H) 6.93 (dd, J=7.07, 1.79 Hz, 2H) 7.03 (d, J=8.24 Hz, 2H) 7.10-7.35 (m, 24H) 7.36-7.45 (m, 2H).

ESI m/z=1001.5 (M+Na).

(2) Preparation of (1S)-1-[5-[4-[4-[(2-amino-1,1-dimethyl-2-oxoethyl)amino]-4-oxobutyl]benzyl]-2-hydroxy-4-methylphenyl]-1,5-anhydro-D-glucitol To a methanol solution (1 mL) of (1S)-1-[5-(4-[(1E)-4-[(2-amino-1,1-dimethyl-2-oxoethyl)amino]-4-oxobut-1-en-1-yl]benzyl)-2-(benzyloxy)-4-methylphenyl]-1,5-anhydro-2,3,4,6-tetra-O-benzyl-D-glucitol (75 mg, 0.0765 mmol) was added 20% palladium hydroxide (15 mg), and the mixture was stirred overnight under a hydrogen atmosphere at room temperature. The reaction solution was filtered through celite, and evaporated under reduced pressure to obtain a residue. Thus obtained residue was purified with silica gel column chromatography (chloroform:methanol=5:1, ethyl acetate:ethanol:water=20:2:1) to obtain the title compound (32 mg, 79%) as a colorless powder. NMR data and MS data of the compound are shown in Table 1.

Example 5

Preparation of (1S)-1-[5-[4-[3-[[amino(imino)methyl]amino]propyl]benzyl]-2-hydroxy-4-methylphenyl]-1,5-anhydro-D-glucitol

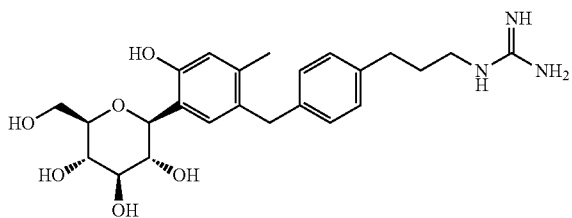

(1) Preparation of (1S)-1-[5-[4-[(1E)-3-[[benzyloxycarbonyl amino(benzyloxycarbonylimino)methyl]amino]prop-1-en-1-yl]benzyl]-2-(benzyloxy)-4-methylphenyl]-1,5-anhydro-2,3,4,6-tetra-O-benzyl-D-glucitol To an acetonitrile solution (3 mL) of (1S)-1,5-anhydro-2,3,4,6-tetra-O-benzyl-1-[2-(benzyloxy)-5-(4-bromobenzyl)-4-methylphenyl]-D-glucitol (271 mg, 0.305 mmol) were added dibenzyl[(Z)-(allylamino)methylylidene]biscarbamate (335 mg, 0.914 mmol), palladium(II) acetate (18 mg, 0.0791 mmol), tri-O-tolylphosphine (61 mg, 0.201 mmol) and triethylamine (154 mg, 1.52 mmol), and reacted at 120° C. for 20 minutes with microwave manufactured by Biotage. The reaction solution was evaporated under reduced pressure. Thus obtained residue was purified with silica gel column chromatography (hexane:ethyl acetate=5:1) to obtain the title compound (163 mg, 46%) as a pale yellow amorphous compound.

1H NMR (300 MHz, CHLOROFORM-D) δ ppm 2.18 (s, 3H) 3.53-3.86 (m, 6H) 3.91 (s, 1H) 4.00 (d, J=11.04 Hz, 1H) 4.19 (t, J=5.75 Hz, 2H) 4.38-4.55 (m, 2H) 4.57-4.67 (m, 2H) 4.80-4.95 (m, 3H) 5.00 (s, 2H) 5.10-5.20 (m, 4H) 6.03-6.16 (m, 1H) 6.41-6.52 (m, 1H) 6.75 (s, 1H) 6.92 (dd, J=7.31, 1.71 Hz, 2H) 7.01 (d, J=8.08 Hz, 2H) 7.07-7.44 (m, 37H) 8.38-8.45 (m, 1H) 11.77 (s, 1H)

ESI m/z=1176(M+H).

(2) Preparation of (1S)-1-[5-[4-[3-[[amino(imino)methyl]amino]propyl]benzyl]-2-hydroxy-4-methylphenyl]-1,5-anhydro-D-glucitol To a methanol (2.6 mL)-ethyl acetate (1.3 mL) mixture solution of (1S)-1-[5-[4-[(1E)-3-[[benzyloxycarbonyl amino (benzyloxycarbonylimino)methyl]amino]prop-1-en-1-yl]benzyl]-2-(benzyloxy)-4-methylphenyl]-1,5-anhydro-2,3,4,6-tetra-O-benzyl-D-glucitol (154 mg, 0.131 mmol) was added 20% palladium hydroxide (160 mg), and the mixture was stirred under a hydrogen atmosphere at room temperature overnight. The reaction solution was filtered through celite, and evaporated under reduced pressure to obtain a residue. Thus obtained residue was dissolved in methanol (1.5 mL). And 20% palladium hydroxide (63 mg) was added thereto, and the mixture was stirred under a hydrogen atmosphere at room temperature for 2 days. The reaction solution was filtered through celite, and evaporated under reduced pressure to obtain a residue. Thus obtained residue was purified with silica gel column chromatography (ethyl acetate:ethanol:water=10:2:1 then 5:2:1, and then ethanol:water=10:1) to obtain the title compound (38 mg, 63%) as a colorless powder. NMR data and MS data of the compound are shown in Table 1.

Example 6

Preparation of (1S)-1,5-anhydro-1-[2-hydroxy-4-methyl-5-[4-[3-[[(4-methylpiperazin-1-yl)carbonyl]amino]propyl]benzyl]phenyl]-D-glucitol

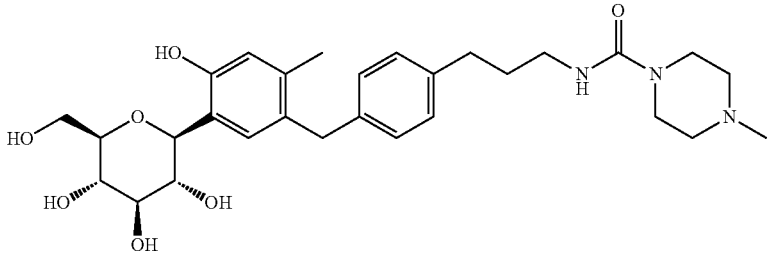

(1) Preparation of (1S)-1,5-anhydro-2,3,4,6-tetra-O-benzyl-1-[2-(benzyloxy)-4-methyl-5-[4-[(1E)-3-[[(4-methylpiperazin-1-yl)carbonyl]amino]prop-1-en-1-yl]benzyl]phenyl]-D-glucitol The title compound (180 mg, 54%) was obtained as a pale yellow oily compound according to the method as with Example 5 (1) in which N-allyl-4-methylpiperazine-1-carboxyamide was used instead of dibenzyl[(Z)-(allylamino)methylylidene]biscarbamate.

1H NMR (300 MHz, CHLOROFORM-D) δ ppm 2.18 (s, 3H) 2.23-2.64 (m, 5H) 3.31-3.86 (m, 11H) 3.91 (s, 2H) 3.95-4.07 (m, 2H) 4.36-4.55 (m, 3H) 4.55-4.66 (m, 2H) 4.77-4.95 (m, 4H) 5.00 (s, 2H) 6.05-6.23 (m, 1H) 6.38-6.50 (m, 1H) 6.74 (s, 1H) 6.92 (dd, J=8.24, 1.24 Hz, 2H) 7.03 (t, J=6.99 Hz, 2H) 7.08-7.36 (m, 25H) 7.37-7.46 (m, 2H).

ESI m/z=992(M+H).

(2) Preparation of (1S)-1,5-anhydro-1-[2-hydroxy-4-methyl-5-[4-[3-[[(4-methylpiperazin-1-yl)carbonyl]amino]propyl]benzyl]phenyl]-D-glucitol The title compound (51 mg, 53%) was obtained as a colorless powder according to the method as with Example 5 (2). NMR data and MS data of the compound are shown in Table 1.

Example 7

Preparation of (1S)-1-[5-[4-[4-[(3-aminopropyl)amino]-4-oxobutyl benzyl]-2-hydroxy-4-methylphenyl]-1,5-anhydro-D-glucitol (1) Preparation of (1S)-1,5-anhydro-2,3,4,6-tetra-O-benzyl-1-[2-(benzyloxy)-5-[4-[(1E)-4-[[3-[(tert-butoxycarbonyl)amino]propyl]amino]-4-oxobut-1-en-1-yl]benzyl]-4-methylphenyl)-D-glucitol The title compound (200 mg, 56%) was obtained as a colorless oily compound according to the method as with Example 5 (1) in which tert-butyl[3-(but-3-enoylamino)propyl]carbamate was used instead of dibenzyl[(Z)-(allylamino)methylylidene]biscarbamate.

1H NMR (300 MHz, CHLOROFORM-D) δ ppm 1.40 (s, 9H) 1.49-1.67 (m, 2H) 2.18 (s, 3H) 3.05-3.20 (m, 4H) 3.29 (q, J=6.32 Hz, 2H) 3.50-3.85 (m, 6H) 3.91 (s, 2H) 4.00 (d, J=10.72 Hz, 1H) 4.37-4.56 (m, 2H) 4.56-4.67 (m, 2H) 4.78-4.95 (m, 4H) 5.00 (s, 2H) 6.10-6.37 (m, 2H) 6.46 (d, J=15.70 Hz, 1H) 6.74 (s, 1H) 6.88-6.96 (m, 2H) 7.02 (d, J=8.24 Hz, 2H) 7.10-7.33 (m, 25H) 7.37-7.44 (m, 2H).

ESI m/z=1073(M+Na).

(2) Preparation of (1S)-1-[5-[4-[(1E)-4-[(3-aminopropyl)amino]-4-oxobutyl-1-ene-1-yl]benzyl]-2-(benzyloxy)-4-methylphenyl]-1,5-anhydro-2,3,4,6-tetra-O-benzyl-D-glucitol To an ethyl acetate solution (2 mL) of (1S)-1,5-anhydro-2,3,4,6-tetra-O-benzyl-1-[2-(benzyloxy)-5-[4-[(1E)-4-[[3-[(tert-butoxycarbonyl)amino]propyl]amino]-4-oxobut-1-en-1-yl]benzyl]-4-methylphenyl]-D-glucitol (200 mg, 0.190 mmol), which was cooled in ice, was added a 4 M hydrochloric acid/ethyl acetate solution, and the mixture was stirred at room temperature for 2 days. To the reaction solution were added ethyl acetate and a saturated sodium bicarbonate aqueous solution to separate an organic layer. The organic layer was washed with water and brine, and dried with anhydrous magnesium sulfate. The drying agent was filtered off, and the solvent was evaporated under reduced pressure. Thus obtained residue was purified with silica gel column chromatography (chloroform:methanol=5:1, and then ethyl acetate:ethanol:water=5:2:1) to obtain the title compound (54 mg, 30%) as a pale yellow oily compound.

1H NMR (300 MHz, CHLOROFORM-D) δ ppm 1.83-1.98 (m, 2H) 2.17 (s, 3H) 2.87-3.03 (m, 2H) 3.03-3.20 (m, 2H) 3.26-3.40 (m, 2H) 3.51-3.83 (m, 6H) 3.89 (s, 2H) 4.00 (d, J=10.57 Hz, 1H) 4.38-4.54 (m, 2H) 4.54-4.66 (m, 2H) 4.80-4.94 (m, 3H) 4.99 (s, 2H) 6.06-6.22 (m, 1H) 6.37-6.62 (m,

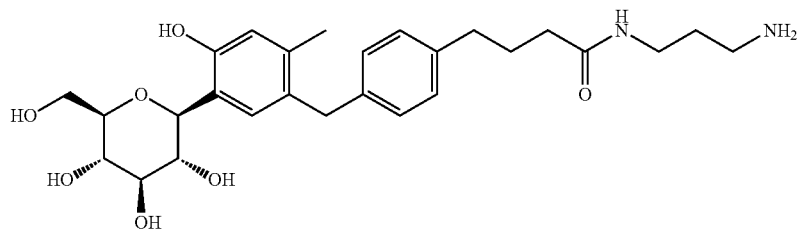

2H) 6.74 (s, 1H) 6.91 (dd, J=6.92, 1.63 Hz, 2H) 7.01 (d, J=8.08 Hz, 2H) 7.07-7.35 (m, 25H) 7.35-7.47 (m, 4H).

ESI m/z=951(M+H).

(3) Preparation of (1S)-1-[5-[4-[4-[(3-aminopropyl)amino]-4-oxobutyl]benzyl]-2-hydroxy-4-methylphenyl]-1,5-anhydro-D-glucitol The title compound (1 mg, 3.5%) was obtained as a colorless amorphous compound according to the method as with Example 5 (2). NMR data and MS data of the compound are shown in Table 1.

Example 8

Preparation of (1S)-1,5-anhydro-1-[5-[4-[3-[[(2-hydroxy-1,1-dimethylethyl)aminocarbonyl]amino]propyl]benzyl]-2-hydroxy-4-methylphenyl)-D-glucitol

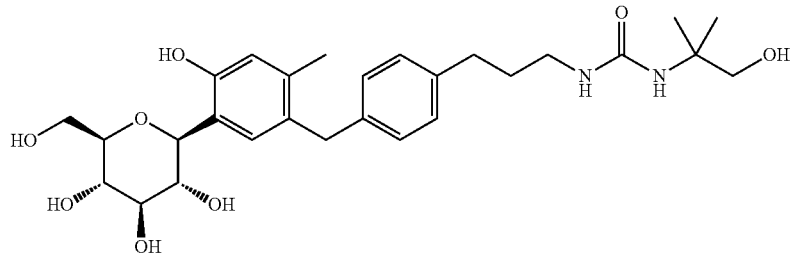

(1) Preparation of (1S)-1,5-anhydro-2,3,4,6-tetra-O-benzyl-1-[5-[4-[(1E)-3-[[(2-hydroxy-1,1-dimethylethyl)aminocarbonyl]amino]prop-1-en-1-yl]benzyl]-2-(benzyloxy)-4-methylphenyl)-D-glucitol To an acetonitrile solution (5.4 mL) of (1S)-1,5-anhydro-2,3,4,6-tetra-O-benzyl-1-[2-(benzyloxy)-5-(4-bromobenzyl)-4-methylphenyl]-D-glucitol (0.48 g, 0.539 mmol) were added N-allyl-N'-(2-hydroxy-1,1-dimethylethyl)urea (223 mg, 1.29 mmol), palladium(II) acetate (24 mg, 0.108 mmol), tri-O-tolylphosphine (66 mg, 0.216 mmol) and triethylamine (273 mg, 2.69 mmol), and the mixture was stirred at 120° C. for 20 minutes with microwave manufactured by Biotage. The reaction solvent was evaporated under reduced pressure. Thus obtained residue was purified with silica gel column chromatography (chloroform and then chloroform:methanol=50:1) to obtain the title compound (210 mg, 40%) as a pale yellow amorphous compound.

1H NMR (300 MHz, CHLOROFORM-D) δ ppm 1.26 (s, 6H) 2.19 (s, 3H) 3.45-4.13 (m, 13H) 4.31-4.69 (m, 6H) 4.77-5.06 (m, 5H) 5.98-6.18 (m, 1H) 6.44 (d, J=15.85 Hz, 1H) 6.74 (s, 1H) 6.86-7.48 (m, 31H)

ESI m/z=982 (M+H).

(2) Preparation of (1S)-1-[2-(acetoxy)-5-[4-[3-[[[2-(acetoxy)-1,1-dimethylethyl]amino]carbonyl]amino]propyl]benzyl]-4-methylphenyl]-1,5-anhydro-2,3,4,6-tetra-O-acetyl-D-glucitol To an ethanol solution (3 mL) of (1S)-1,5-anhydro-2,3,4,6-tetra-O-benzyl-1-[5-[4-[(1E)-3-[[(2-hydroxy-1,1-dimethylethyl)aminocarbonyl]amino]prop-1-en-1-yl]benzyl]-2-(benzyloxy)-4-methylphenyl]-D-glucitol (210 mg, 0.214 mmol) was added 20% palladium hydroxide (210 mg), and the mixture was stirred overnight under a hydrogen atmosphere at room temperature. The reaction solution was filtered through celite, and the solvent was evaporated under reduced pressure to obtain a residue. Thus obtained residue was purified with silica gel column chromatography (chloroform:methanol=5:1) to obtain a colorless powder substance (83 mg). To a pyridine solution (1 mL) of this substance was added acetic anhydride (0.25 mL), and the mixture was stirred overnight at room temperature. To this reaction solution was added a saturated sodium bicarbonate aqueous solution and the resulting mixture was extracted with ethyl acetate. The organic layer was washed with brine, and dried with anhydrous magnesium sulfate. The drying agent was filtered off, and the solvent was evaporated under reduced pressure. Thus obtained residue was purified with silica gel column chromatography (hexane:ethyl acetate=2:3 to 1:2) to obtain the title compound (70 mg) as a colorless amorphous compound.

(3) Preparation of (1S)-1,5-anhydro-1-[5-[4-[3-[[(2-hydroxy-1,1-dimethylethyl)aminocarbonyl]amino]propyl]benzyl]-2-hydroxy-4-methylphenyl]-D-glucitol To a methanol solution (1 mL) of (1S)-1-[2-(acetoxy)-5-[4-[3-[[[2-(acetoxy)-1,1-dimethylethyl]amino]carbonyl]amino]propyl]benzyl]-4-methylphenyl]-1,5-anhydro-2,3,4,6-tetra-O-acetyl-D-glucitol (70 mg) was added sodium methoxide (a 1 M methanol solution, 0.5 mL, 0.5 mmol), and the mixture was stirred for an hour at room temperature. To this reaction solution was added dry ice, and the solvent was evaporated under reduced pressure. Thus obtained residue was purified with silica gel column chromatography (chloroform:methanol=5:1) to obtain the title compound (35 mg, 31%, 3 steps) as a colorless oily compound. NMR data and MS data of the compound are shown in Table 1.

Example 9

Preparation of (1S)-1,5-anhydro-1-[5-[4-[3-[[[2-hydroxy-1,1-bis(hydroxymethyl)ethyl]aminocarbonyl]amino]propyl]benzyl]-2-hydroxy-4-methylphenyl]-D-glucitol

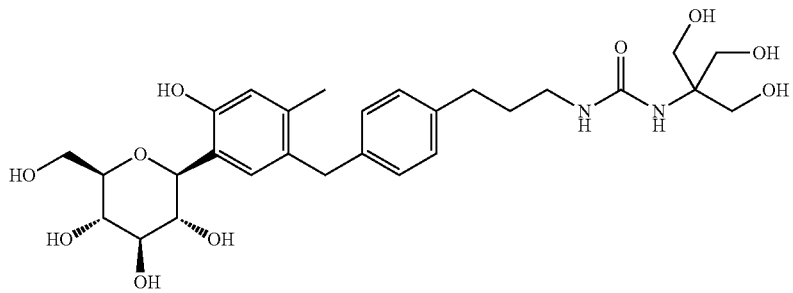

(1) Preparation of (1S)-1,5-anhydro-2,3,4,6-tetra-O-benzyl-1-[5-[4-[(1E)-3-[[[2-hydroxy-1,1-bis(hydroxymethyl)ethyl]aminocarbonyl]amino]prop-1-en-1-yl]benzyl]-2-(benzyloxy)-4-methylphenyl]-D-glucitol The title compound (322 mg) was obtained as a pale yellow amorphous compound according to the method as with Example 8 (1) in which N-allyl-N'-[2-hydroxy-1,1-bis(hydroxymethyl)ethyl]urea was used instead of N-allyl-N'-(2-hydroxy-1,1-dimethylethyl) urea.

1H NMR (300 MHz, CHLOROFORM-D) δ ppm 2.19 (s, 3H) 3.48-4.06 (m, 17H) 4.34-5.08 (m, 11H) 5.98-6.11 (m, 1H) 6.44 (d, J=16.32 Hz, 1H) 6.74 (s, 1H) 6.84-7.46 (m, 31H). ESI/APCl m/z=1014(M+H).

(2) Preparation of (1S)-1,5-anhydro-1-[5-[4-[2-[[[2-hydroxy-1,1-bis(hydroxymethyl)ethyl]aminocarbonyl]amino]propyl]benzyl]-2-hydroxy-4-methylphenyl]-D-glucitol The title compound (60 mg) was obtained as a colorless powder according to the method as with Example 8 (2) in which (1S)-1,5-anhydro-2,3,4,6-tetra-O-benzyl-1-[5-[4-[(1E)-3-[[[2-hydroxy-1,1-bis(hydroxymethyl)ethyl]aminocarbonyl]amino]prop-1-en-1-yl]benzyl]-2-(benzyloxy)-4-methylphenyl]-D-glucitol was used instead of (1S)-1,5-anhydro-2,3,4,6-tetra-O-benzyl-1-[5-[4-[(1E)-3-[[(2-hydroxy-1,1-dimethylethyl)aminocarbonyl]amino]prop-1-en-1-yl]benzyl]-2-(benzyloxy)-4-methylphenyl)-D-glucitol. NMR data and MS data of the compound are shown in Table 1.

Example 10

Preparation of (1S)-1,5-anhydro-1-[5-[4-[2-[[(2-hydroxy-1,1-dimethylethyl)aminocarbonyl]amino]ethyl]benzyl]-2-hydroxy-4-methylphenyl]-D-glucitol

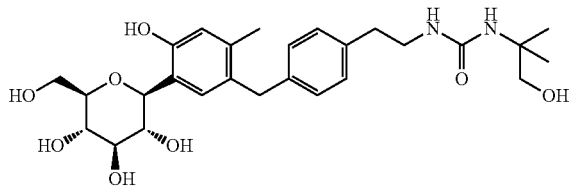

(1) Preparation of (1S)-1,5-anhydro-2,3,4,6-tetra-O-benzyl-1-[2-(benzyloxy)-5-[4-[2-[[[(2-hydroxy-1,1-dimethylethyl)amino]carbonyl]amino]ethyl]benzyl]-4-methylphenyl]-D-glucitol To a chloroform solution (3 mL) of 4-nitrophenyl chloroformate (0.177 g, 0.879 mmol) and pyridine (0.071 mL, 0.88 mmol), which was cooled in ice, was added dropwise a chloroform solution (3 mL) of (1S)-1-[5-[4-(2-aminoethyl)benzyl]-2-(benzyloxy)-4-methylphenyl]-1,5-anhydro-2,3,4,6-tetra-O-benzyl-D-glucitol (0.250 g, 0.293 mmol), and the mixture was stirred for 20 minutes at room temperature. After that, a chloroform solution (3 mL) of 2-amino-2-methyl-1-propanol (0.209 g, 2.344 mmol) and dimethyl sulfoxide (3 mL) were added thereto, and the mixture was stirred overnight at the same temperature. To the reaction solution was added water, and the resulting mixture was extracted with ethyl acetate. The organic layer was washed with water and brine (3 times), and dried with anhydrous magnesium sulfate. The drying agent was filtered off, and the solvent was evaporated under reduced pressure to obtain a residue. Thus obtained residue was purified with NH type silica gel column chromatography (chloroform) to obtain the title compound (0.184 g, 65%) as a pale yellow oily compound.

1H NMR (300 MHz, CHLOROFORM-D) δ ppm 1.18 (s, 6H) 2.21 (s, 3H) 2.68 (t, J=6.68 Hz, 2H) 3.21-3.37 (m, 2H) 3.45-3.94 (m, 10H) 4.00 (d, J=10.88 Hz, 1H) 4.37-4.65 (m, 5H) 4.81-5.03 (m, 5H) 6.75 (s, 1H) 6.87-7.05 (m, 7H) 7.07-7.44 (m, 23H)

(2) Preparation of (1S)-1,5-anhydro-1-[5-[4-[2-[[(2-hydroxy-1,1-dimethylethyl)aminocarbonyl]amino]ethyl]benzyl]-2-hydroxy-4-methylphenyl]-D-glucitol To a methanol solution (4 mL) of (1S)-1,5-anhydro-2,3,4,6-tetra-O-benzyl-1-[2-(benzyloxy)-5-[4-[2-[[[(2-hydroxy-1,1-dimethylethyl)amino]carbonyl]amino]ethyl]benzyl]-4-methylphenyl]-D-glucitol (0.184 mg, 0.190 mmol) was added 20% palladium hydroxide (0.180 g), and the mixture was stirred under a hydrogen atmosphere at room temperature overnight. The reaction solution was filtered through celite and evaporated under reduced pressure. Thus obtained residue was purified with silica gel column chromatography (chloroform:methanol=17:3) to obtain the title compound (57 mg, 58%) as a colorless powder. NMR data and MS data of the compound are shown in Table 1.

Example 11

Preparation of (1S)-1,5-anhydro-1-[5-[4-[2-[[[2-hydroxy-1,1-bis(hydroxymethyl)ethyl]aminocarbonyl]amino]ethyl]benzyl]-2-hydroxy-4-methylphenyl]-D-glucitol

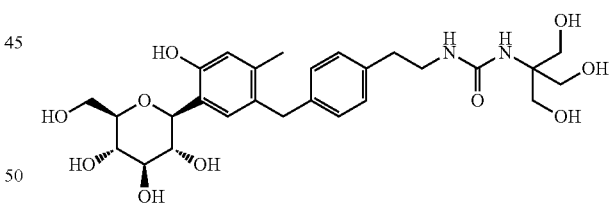

(1) Preparation of (1S)-1,5-anhydro-2,3,4,6-tetra-O-benzyl-1-[2-(benzyloxy)-5-[4-[2-[[[[2-hydroxy-1,1-bis(hydroxymethyl)ethyl]amino]carbonyl]amino]ethyl]benzyl]-4-methylphenyl]-D-glucitol The title compound (251 mg) was obtained as a pale yellow amorphous compound according to the method as with Example 10 (1) in which tris(hydroxymethyl)aminomethane was used instead of 2-amino-2-methyl-1-propanol. 1H NMR (300 MHz, CHLOROFORM-D) δ ppm 2.22 (s, 3H) 2.68 (t, J=6.61 Hz, 2H) 3.24-3.35 (m, 2H) 3.41-3.99 (m, 14H) 4.00 (d, J=10.88 Hz, 1H) 4.38-4.70 (m, 5H) 4.79-5.03 (m, 5H) 5.27 (s, 1H) 6.76 (s, 1H) 6.87-7.44 (m, 30H).

(2) Preparation of (1S)-1,5-anhydro-1-[5-[4-[2-[[[2-hydroxy-1,1-bis(hydroxymethyl)ethyl]aminocarbonyl]amino]ethyl]benzyl]-2-hydroxy-4-methylphenyl]-D-glucitol The title compound (85 mg) was obtained as a colorless powder according to the method as with Example 10 (2) in which (1S)-1,5-anhydro-2,3,4,6-tetra-O-benzyl-1-[2-(benzyloxy)-5-[4-[2-[[[[2-hydroxy-1,1-bis(hydroxymethyl)ethyl]amino]carbonyl]amino]ethyl]benzyl]-4-methylphenyl]-D-glucitol was used instead of (1S)-1,5-anhydro-2,3,4,6-tetra-O-benzyl-1-[2-(benzyloxy)-5-[4-[2-[[[(2-hydroxy-1,1-dimethylethyl)amino]carbonyl]amino]ethyl]benzyl]-4-methylphenyl]-D-glucitol. NMR data and MS data of the compound are shown in Table 1.

Example 12

Preparation of (1S)-1,5-anhydro-1-[5-[4-[2-[[[1-[1-(4-methylpiperazin-1-yl)carbonyl]-1-(methyl)ethyl]aminocarbonyl]amino]ethyl]benzyl]-2-hydroxy-4-methylphenyl]-D-glucitol

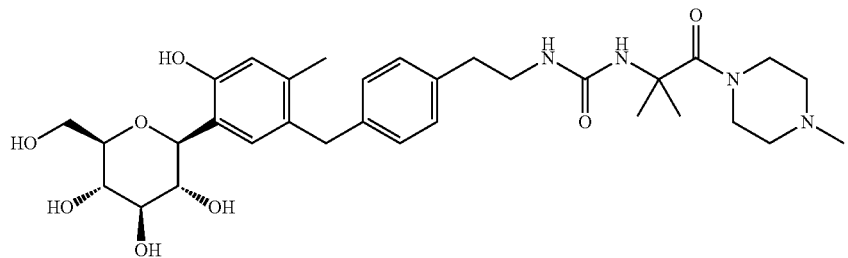

(1) Preparation of (1S)-1,5-anhydro-2,3,4,6-tetra-O-benzyl-1-[2-(benzyloxy)-5-[4-[2-[[[[1-[1-(4-methylpiperazin-1-yl)carbonyl]-1-(methyl)ethyl]amino]carbonyl]amino]ethyl]benzyl]-4-methylphenyl]-D-glucitol The title compound (326 mg) was obtained as a pale yellow amorphous compound according to the method as with Example 10 (1) in which 2-methyl-1-(4-methylpiperazin-1-yl)-1-oxopropane-2-amine was used instead of 2-amino-2-methyl-1-propanol.

1H NMR (300 MHz, CHLOROFORM-D) δ ppm 1.41 (s, 6H) 2.20 (s, 3H) 2.26 (s, 3H) 2.31-2.37 (m, 4H) 2.70 (t, J=6.84 Hz, 2H) 3.29-3.41 (m, 2H) 3.50-3.94 (m, 12H) 4.00 (d, J=10.88 Hz, 1H) 4.37-4.67 (m, 5H) 4.81-5.02 (m, 5H) 6.75 (s, 1H) 6.88-7.44 (m, 30H).

(2) Preparation of (1S)-1,5-anhydro-1-[5-[4-[2-[[[1-[1-(4-methylpiperazin-1-yl)carbonyl]-1-(methyl)ethyl]aminocarbonyl]amino]ethyl]benzyl]-2-hydroxy-4-methylphenyl]-D-glucitol The title compound (35 mg) was obtained as a colorless powder according to the method as with Example 10 (2) in which (1S)-1,5-anhydro-2,3,4,6-tetra-O-benzyl-1-[2-(benzyloxy)-5-[4-[2-[[[[1-[1-(4-methylpiperazin-1-yl)carbonyl]-1-(methyl)ethyl]amino]carbonyl]amino]ethyl)benzyl]-4-methylphenyl]-D-glucitol was used instead of (1S)-1,5-anhydro-2,3,4,6-tetra-O-benzyl-1-[2-(benzyloxy)-5-[4-[2-[[[(2-hydroxy-1,1-dimethylethyl)amino]carbonyl]amino]ethyl]benzyl]-4-methylphenyl]-D-glucitol. NMR data and MS data of the compound are shown in Table 1.

Example 13

Preparation of (1S)-1,5-anhydro-1-[5-[4-[2-[[[2-hydroxy-1,1-bis(hydroxymethyl)ethyl]aminocarbonyl]amino]ethoxy]-2-methylbenzyl]-2-hydroxy-4-methylphenyl]-D-glucitol

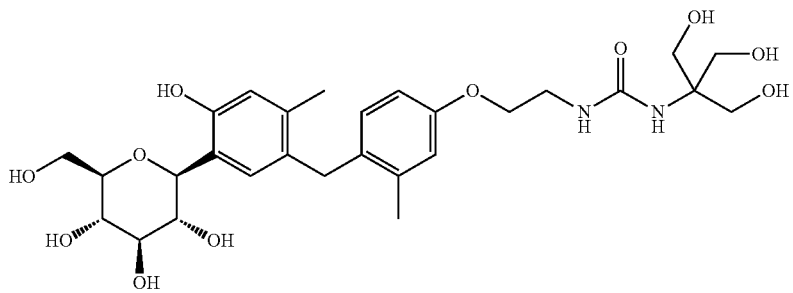

To a chloroform solution (0.5 mL) of 1,1-carbonyldiimidazole (14 mg, 0.089 mmol) were added a chloroform solution (1.5 mL) of (1S)-1-[5-[4-(2-aminoethoxy)-2-methylbenzyl]-2-(benzyloxy)-4-methylphenyl]-1,5-anhydro-2,3,4,6-tetra-O-benzyl-D-glucitol (52 mg, 0.059 mmol) and N-methyl morpholine (9 mg), and the mixture was stirred for 15 minutes at room temperature. After that, to this reaction solution were added tris(hydroxymethyl)aminomethane (21 mg, 0.177 mmol) and N,N-dimethylformamide (2 mL), and this reaction mixture was stirred at 60° C. for 1.5 hours. After the reaction mixture was cooled to room temperature, ethyl acetate was added thereto. And the mixture was washed with water, 1 M hydrochloric acid, and brine, and dried with anhydrous magnesium sulfate. The drying agent was filtered off, and the solvent was evaporated under reduced pressure to obtain 60 mg of a residue.

Thus obtained residue was dissolved in methanol (1 mL). And 20% palladium hydroxide (15 mg) was added thereto, and the mixture was stirred under a hydrogen atmosphere at room temperature for 2 hours. The reaction solution was filtered through celite, and evaporated under reduced pressure to obtain a residue. Thus obtained residue was purified with silica gel column chromatography (ethyl acetate:ethanol:water=10:2:1) to obtain the title compound (30 mg, 86%) as a colorless powder. NMR data and MS data of the compound are shown in Table 1.

Example 14

Preparation of (1S)-1,5-anhydro-1-[4-chloro-5-[4-[2-[[[2-hydroxy-1,1-bis(hydroxymethyl)ethyl]aminocarbonyl]amino]ethyl]benzyl]-2-hydroxyphenyl]-D-glucitol

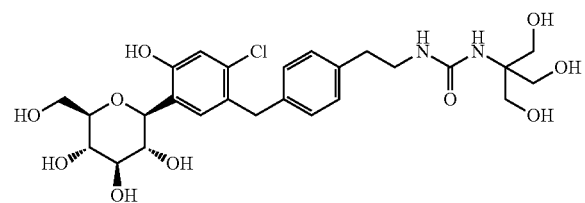

To a chloroform solution (1 mL) of 1,1'-carbonyldiimidazole (10.8 mg, 0.0669 mmol) were added a chloroform solution (1 mL) of (1S)-1-[5-[4-(2-aminoethyl)benzyl]-2-(benzyloxy)-4-chlorophenyl]-1,5-anhydro-2,3,4,6-tetra-O-benzyl-D-glucitol (39.0 mg, 0.0446 mmol) and N-methyl morpholine (7.36 μL), and the mixture was stirred for 10 minutes at room temperature. After that, to this reaction solution were added tris(hydroxymethyl)aminomethane (16.2 mg, 0.134 mmol) and N,N-dimethylformamide (1 mL), and this reaction mixture was stirred at 60° C. for 2 hours. After the reaction mixture was cooled to room temperature, ethyl acetate was added thereto. And the mixture was washed with water, 1 M hydrochloric acid, and brine, and dried with anhydrous magnesium sulfate. The drying agent was filtered off, and the solvent was evaporated under reduced pressure to obtain 41.2 mg of a residue.

Thus obtained residue (22.3 mg, 0.022 mmol) was dissolved in chloroform (250 μL) and ethanethiol (250 μL). And to this solution cooled in ice was added BF$_3$·Et$_2$O (50 μL), and the mixture was stirred at the same temperature for 2 hours. The solvent was evaporated and thus obtained residue was purified with silica gel column chromatography (ethyl acetate:ethanol:water=10:2:1 and then methanol) to obtain the title compound (10.8 mg, 86%) as a colorless amorphous compound. NMR data and MS data of the compound are shown in Table 1.

Example 15

Preparation of (1S)-1,5-anhydro-1-[5-[4-[2-[[[2-hydroxy-1,1-bis(hydroxymethyl)ethyl]aminocarbonyl]amino)ethyl]benzyl]-2-hydroxyphenyl]-D-glucitol

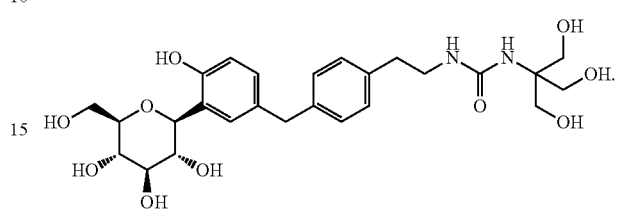

The title compound (8.5 mg, 93%) was obtained as a colorless oily compound according to the method as with Example 13 in which (1S)-1-[5-[4-(2-aminoethyl)benzyl]-2-(benzyloxy)-4-chlorophenyl]-1,5-anhydro-2,3,4,6-tetra-O-benzyl-D-glucitol was used instead of (1S)-1-[5-[4-(2-aminoethoxy)-2-methyl benzyl]-2-(benzyloxy)-4-methylphenyl]-1,5-anhydro-2,3,4,6-tetra-O-benzyl-D-glucitol.

NMR data and MS data of the compound are shown in Table 1.

Example 16

Preparation of (1S)-1,5-anhydro-1-[3-[4-[2-[[[2-hydroxy-1,1-bis(hydroxymethyl)ethyl]aminocarbonyl]amino]ethyl]benzyl]phenyl]-D-glucitol

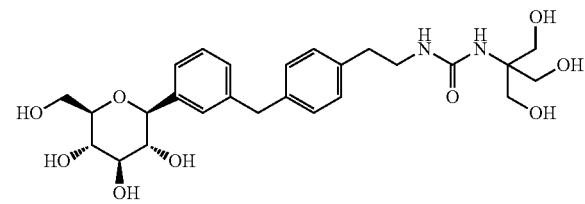

A crude product of the title compound was obtained according to the method as with Example 13 in which (1S)-1-[3-[4-(2-aminoethyl)benzyl]-4-chlorophenyl]-1,5-anhydro-2,3,4,6-tetra-O-benzyl-D-glucitol was used instead of (1S)-1-[5-[4-(2-aminoethoxy)-2-methyl benzyl]-2-(benzyloxy)-4-methylphenyl]-1,5-anhydro-2,3,4,6-tetra-O-benzyl-D-glucitol. After that, the crude product was purified with HPLC (0.025% acetic acid aqueous solution:acetonitrile=3:1, YMC-Pack ODS-AM 150×10 mm I.D., 5.0 mL/min., λ=210 nM) to obtain the title compound (13 mg, 15%) as a colorless amorphous compound. NMR data and MS data of the compound are shown in Table 1.

Example 17

Preparation of (1S)-1,5-anhydro-1-[4-chloro-3-[4-[2-[[[2-hydroxy-1,1-bis(hydroxymethyl)ethyl]aminocarbonyl]amino]ethyl]benzyl]phenyl]-D-glucitol

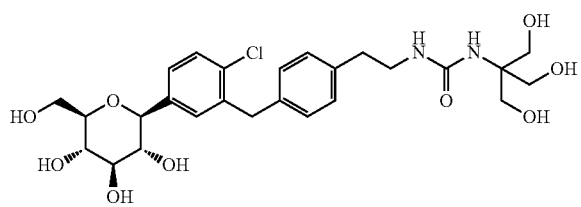

A crude product of the title compound was obtained according to the method as with Example 14 in which (1S)-1-[3-[4-(2-aminoethyl)benzyl]-4-chlorophenyl]-1,5-anhydro-2,3,4,6-tetra-O-benzyl-D-glucitol was used instead of (1S)-1-[5-[4-(2-aminoethyl)benzyl]-2-(benzyloxy)-4-chlorophenyl]-1,5-anhydro-2,3,4,6-tetra-O-benzyl-D-glucitol. After that, the crude product was purified with HPLC (0.025% acetic acid aqueous solution:acetonitrile=7:3, Waters Sunfire Prep C, 150×19 mm I.D., 8.0 mL/min., λ=210 nM) to obtain the title compound (12 mg, 17%) as a colorless amorphous compound.

NMR data and MS data of the compound are shown in Table 1.

Example 18

Preparation of (1S)-1,5-anhydro-1-[2-hydroxy-5-[4-[4-[[2-hydroxy-1,1-bis(hydroxymethyl)ethyl]amino]-4-oxobutyl]benzyl]-4-methylphenyl]-D-galactitol

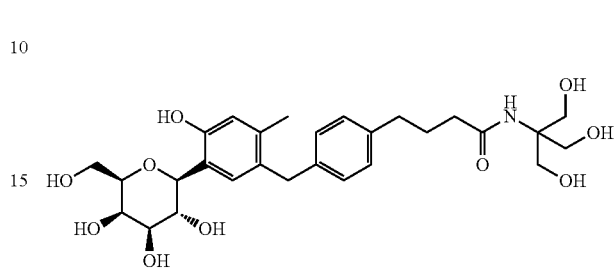

The title compound (37 mg, 47%) was obtained as a colorless powder from (1S)-1,5-anhydro-2,3,4,6-tetra-O-benzyl-1-[2-(benzyloxy)-5-[4-[(1E)-3-carboxyprop-1-en-1-yl]benzyl]-4-methylphenyl]-D-galactitol (199 mg, 0.222 mmol) according to the method as with Example 3. NMR data and MS data of the compound are shown in Table 1.

Furthermore, compounds 19 to 36 were also synthesized from corresponding materials in accordance with Reference Examples and Examples.

TABLE 1

| Compound No | structure | NMR (solvent, methanol-$d_4$), MS |
|---|---|---|
| 1 | 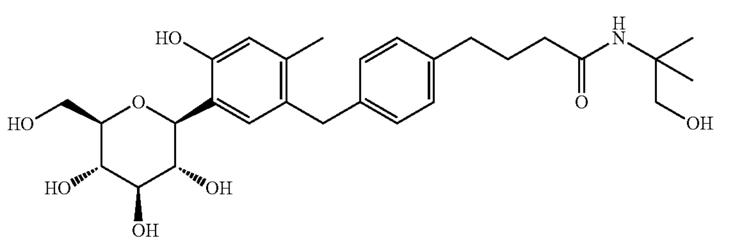 | 1H NMR (600 MHz) δ ppm 1.25 (s, 6 H) 1.81-1.89 (m, 2 H) 2.09 (s, 3 H) 2.12-2.18 (m, 2 H) 2.54-2.59 (m, 2 H) 3.38-3.50 (m, 3 H) 3.53-3.57 (m, 3 H) 3.70 (dd, J = 12.15, 5.27 Hz, 1 H) 3.84-3.89 (m, 3 H) 4.51 (d, J = 9.63 Hz, 1 H) 6.63 (s, 1 H) 6.99-7.08 (m, 4 H) 7.12 (s, 1 H). ESI m/z = 518 (M + H). |
| 2 | 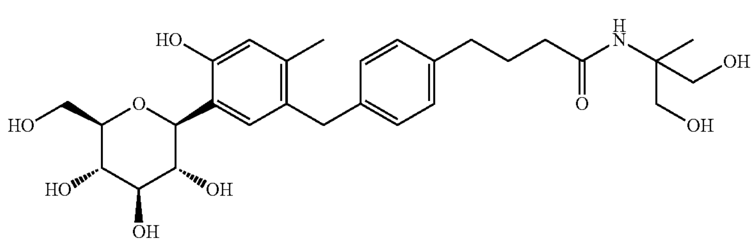 | 1H NMR (600 MHz) δ ppm 1.22 (s, 3 H) 1.80-1.91 (m, 2 H) 2.09 (s, 3 H) 2.15-2.23 (m, 2 H) 2.58 (t, J = 7.57 Hz, 2 H) 3.37-3.50 (m, 3 H) 3.51-3.73 (m, 6 H) 3.83-3.90 (m, 3 H) 4.51 (d, J = 9.63 Hz, 1 H) 6.63 (s, 1 H) 6.99-7.09 (m, 4 H) 7.12 (s, 1 H). ESI m/z = 556 (M + Na). |
| 3 | 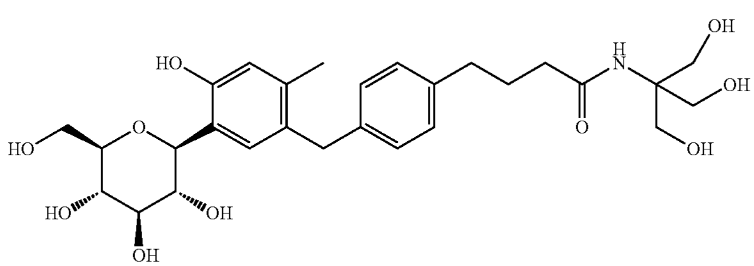 | 1H NMR (600 MHz) δ ppm 1.84-1.93 (m, 2 H) 2.10 (s, 3 H) 2.21-2.27 (m, 2 H) 2.59 (t, J = 7.57 Hz, 2 H) 3.37-3.44 (m, 2 H) 3.48 (t, J = 8.48 Hz, 1 H) 3.53-3.59 (m, 1 H) 3.70 (s, 7 H) 3.83-3.90 (m, 3 H) 4.51 (d, J = 9.63 Hz, 1 H) 6.63 (s, 1 H) 6.99-7.10 (m, 4 H) 7.11 (s, 1 H). ESI m/z = 572 (M + Na). |

TABLE 1-continued

| Compound No | structure | NMR (solvent, methanol-d$_4$), MS |
|---|---|---|
| 4 | 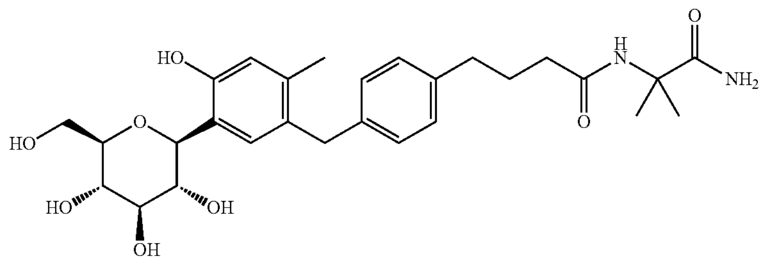 | 1H NMR (600 MHz) δ ppm 1.44 (s, 6 H) 1.82-1.90 (m, 2 H) 2.09 (s, 3 H) 2.19 (t, J = 7.57 Hz, 2 H), 2.57 (t, J = 7.57 Hz, 2 H) 3.37-3.52 (m, 2 H) 3.56 (t, J = 9.17 Hz, 2 H) 3.70 (dd, J = 11.92, 5.04 Hz, 1 H) 3.82-3.90 (m, 3 H) 4.51 (d, J = 9.63 Hz, 1 H) 6.63 (s, 1 H) 6.98-7.08 (m, 4 H) 7.11 (s, 1 H). ESI m/z = 553 (M + Na). |
| 5 | 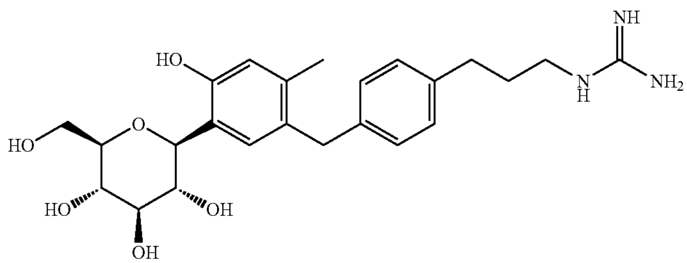 | 1H NMR (600 MHz) δ ppm 1.82-1.91 (m, 2 H) 2.10 (s, 3 H) 2.61-2.67 (m, 2 H) 3.15 (t, J = 7.11 Hz, 2 H) 3.37-3.44 (m, 2 H) 3.48 (t, J = 8.71 Hz, 1 H) 3.55 (t, J = 9.17 Hz, 1 H) 3.70 (dd, J = 11.92, 5.04 Hz, 1 H) 3.83-3.91 (m, 3 H) 4.51 (d, J = 9.63 Hz, 1 H) 6.63 (s, 1 H) 7.01-7.13 (m, 5 H). ESI m/z = 460 (M + H). |
| 6 | 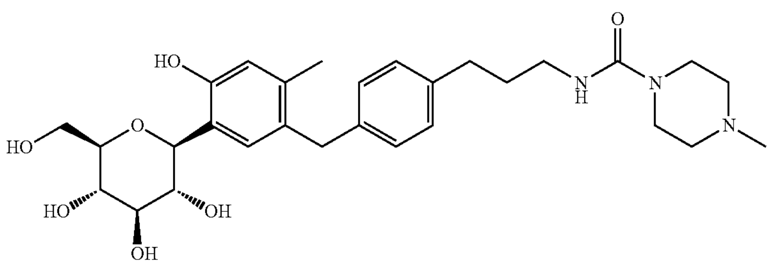 | 1H NMR (600 MHz) δ ppm 1.74-1.82 (m, 2 H) 2.10 (s, 3 H) 2.29 (s, 3 H) 2.37-2.42 (m, 4 H) 2.54-2.60 (m, 2 H) 3.15 (t, J = 7.11 Hz, 2 H) 3.33-3.44 (m, 6 H) 3.48 (t, J = 8.94 Hz, 1 H) 3.53-3.58 (m, 1 H) 3.70 (dd, J = 12.15, 5.27 Hz, 1 H) 3.83-3.89 (m, 3 H) 4.51 (d, J = 9.63 Hz, 1 H) 6.63 (s, 1 H) 6.99-7.09 (m, 4 H) 7.12 (s, 1 H). ESI m/z = 544 (M + H). |
| 7 | 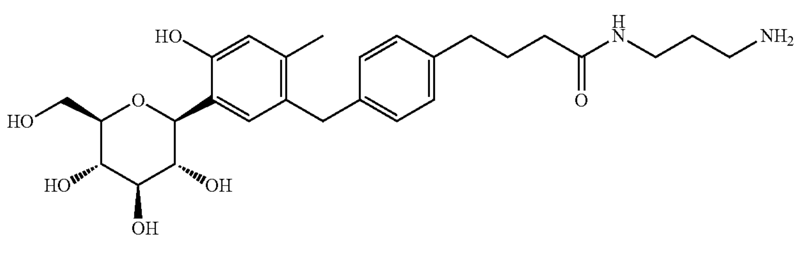 | 1H NMR (600 MHz) δ ppm 1.77-1.84 (m, 2 H) 1.85-1.93 (m, 2 H) 2.10 (s, 3 H) 2.17-2.23 (m, 2 H) 2.58 (t, J = 7.57 Hz, 2 H) 2.87-2.91 (m, 2 H), 3.24 (t, J = 6.65 Hz, 2 H) 3.37-3.51 (m, 3 H) 3.53-3.58 (m, 1 H) 3.70 (dd, J = 12.15, 5.27 Hz, 1 H) 3.84-3.88 (m, 3 H) 4.51 (d, J = 9.63 Hz, 1 H) 6.63 (s, 1 H) 7.01-7.08 (m, 4 H) 7.11 (s, 1 H). ESI m/z = 503 (M + H). |
| 8 | 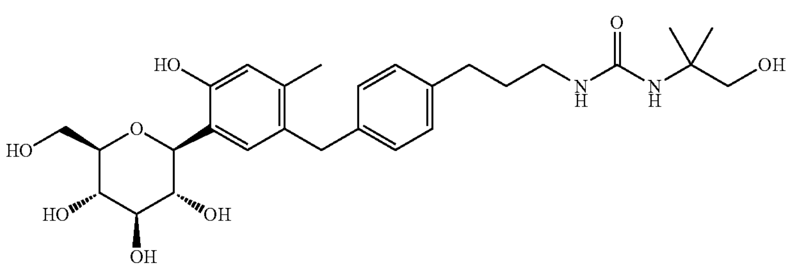 | 1H NMR (600 MHz) δ ppm 1.23 (s, 6 H) 1.68-1.76 (m, 2 H) 2.09 (s, 3 H) 2.54-2.60 (m, 2 H) 3.05 (t, J = 6.88 Hz, 2 H) 3.37-3.44 (m, 2 H) 3.45-3.58 (m, 4 H) 3.70 (dd, J = 11.92, 5.04 Hz, 1 H) 3.83-3.90 (m, 3 H) 4.51 (d, J = 9.63 Hz, 1 H) 6.63 (s, 1 H) 6.98-7.03 (m, 2 H) 7.03-7.08 (m, 2 H) 7.12 (s, 1 H). ESI m/z = 533 (M + H), 531 (M − H). |

TABLE 1-continued

| Compound No | structure | NMR (solvent, methanol-d$_4$), MS |
|---|---|---|
| 9 | 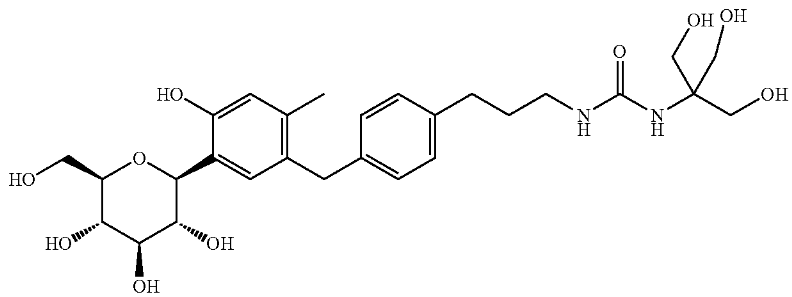 | 1H NMR (600 MHz) δ ppm 1.70-1.77 (m, 2 H) 2.09 (s, 3 H) 2.54-2.62 (m, 2 H) 3.07 (t, J = 6.88 Hz, 2 H) 3.36-3.60 (m, 5 H) 3.61-3.73 (m, 6 H) 3.82-3.91 (m, 3 H) 4.51 (d, J = 9.63 Hz, 1 H) 6.63 (s, 1 H) 6.99-7.08 (m, 4 H) 7.08-7.15 (m, 1 H). ESI m/z = 587 (M + Na). |
| 10 | 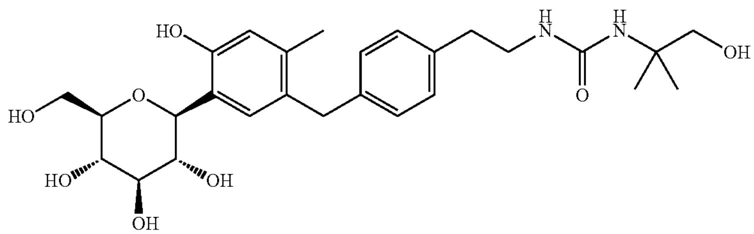 | 1H NMR (300 MHz) δ ppm 1.25 (s, 6 H) 2.13 (s, 3 H) 2.72 (t, J = 7.07 Hz, 2 H) 3.25-3.37 (m, 3 H) 3.38-3.80 (m, 6 H) 3.86-3.96 (m, 3 H) 4.56 (d, J = 9.33 Hz, 1 H) 6.68 (s, 1 H) 7.03-7.19 (m, 5 H). ESI m/z = 519 (M + H), 541 (M + Na) |
| 11 | 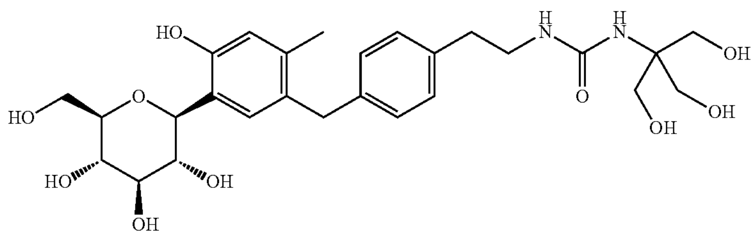 | 1H NMR (600 MHz) δ ppm 2.09 (s, 3 H) 2.68 (t, J = 7.34 Hz, 2 H) 3.24-3.32 (m, 3 H) 3.36-3.66 (m, 9 H) 3.68-3.74 (m, 1 H) 3.81-3.90 (m, 3 H), 4.52 (d, J = 9.63 Hz, 1 H) 6.64 (s, 1 H) 7.00-7.14 (m, 5 H). ESI m/z = 552 (M + H), 574 (M + Na) |
| 12 | 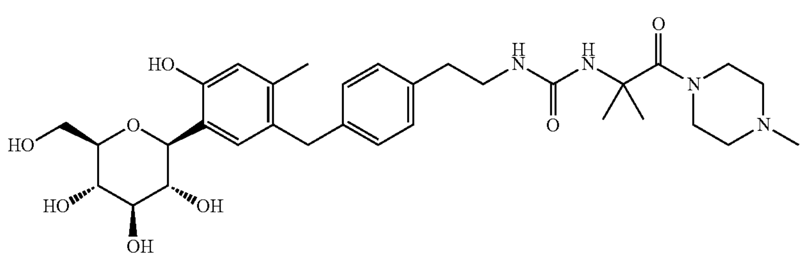 | 1H NMR (600 MHz) δ ppm 1.39 (s, 6 H) 2.10 (s, 3 H) 2.23 (s, 3 H) 2.70 (t, J = 7.11 Hz, 2 H) 3.26-3.91 (m, 18 H) 4.52 (d, J = 9.63 Hz, 1 H) 6.63 (s, 1 H) 7.02-7.14 (m, 5 H). ESI m/z = 616 (M + H), 637 (M + Na). |
| 13 | 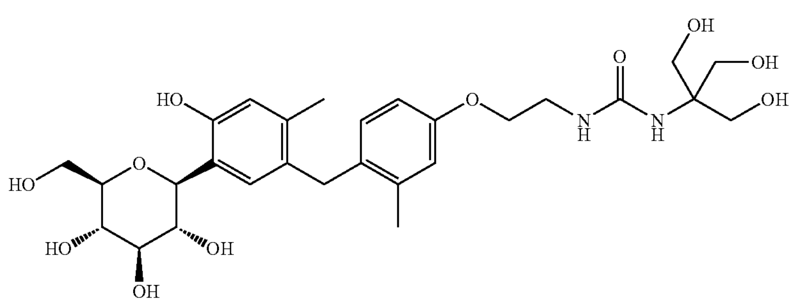 | 1H NMR (300 MHz) δ ppm 2.12 (s, 3 H) 2.25 (s, 3 H) 3.34-3.57 (m, 6 H) 3.66 (s, 6 H) 3.67-3.71 (m, 1 H) 3.77 (s, 2 H) 3.79-3.89 (m, 1 H) 3.96 (t, J = 5.28 Hz, 2 H) 4.45 (d, J = 9.48 Hz, 1 H) 6.58-6.65 (m, 1 H) 6.67 (s, 1 H) 6.69-6.81 (m, 2 H) 6.90 (s, 1 H). ESI m/z = 581 (M + H), 603 (M + Na). |

TABLE 1-continued

| Compound No | structure | NMR (solvent, methanol-d₄), MS |
|---|---|---|
| 14 | 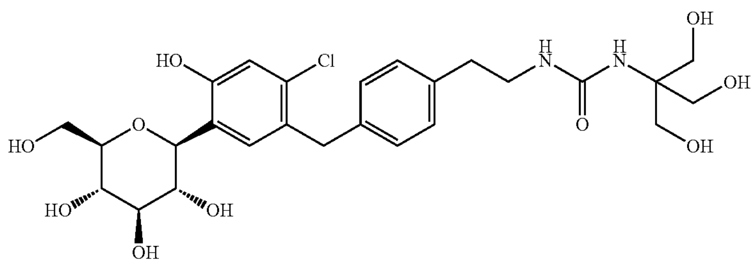 | 1H NMR (600 MHz) δ ppm 2.69 (t, J = 7.11 Hz, 2 H) 3.24-3.28 (m, 2 H) 3.34-3.41 (m, 2 H) 3.42-3.50 (m, 2 H) 3.60 (s, 6 H) 3.67 (dd, J = 12.15, 5.27 Hz, 1 H) 3.83 (dd, J = 11.92, 1.83 Hz, 1 H) 3.89-4.01 (m, 2 H) 4.51 (d, J = 9.17 Hz, 1 H) 6.81 (s, 1 H) 7.08 (s, 4 H) 7.24 (s, 1 H). ESI m/z = 571 (M + H), 593 (M + Na). |
| 15 | 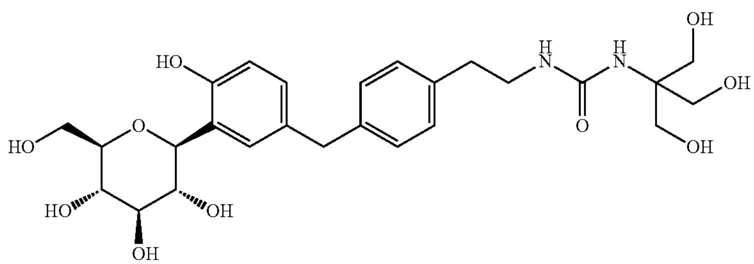 | 1H NMR (600 MHz) δ ppm 2.69 (t, J = 7.11 Hz, 2 H) 3.24-3.28 (m, 2 H) 3.34-3.43 (m, 2 H) 3.46 (t, J = 8.48 Hz, 1 H) 3.52 (t, J = 9.17 Hz, 1 H) 3.60 (s, 6 H) 3.68 (dd, J = 11.92, 5.04 Hz, 1 H) 3.77-3.89 (m, 3 H) 4.52 (d, J = 9.63 Hz, 1 H) 6.70 (d, J = 8.25 Hz, 1 H) 6.92 (dd, J = 8.25, 1.83 Hz, 1 H) 7.09 (s, 4 H) 7.18 (d, J = 2.29 Hz, 1 H). ESI m/z = 537 (M + H), 559 (M + Na). |
| 16 | 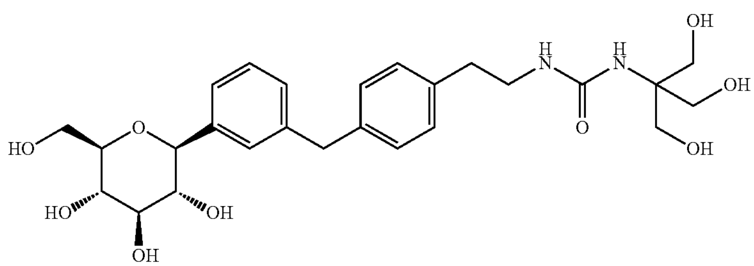 | 1H NMR (300 MHz) δ ppm 2.71 (t, J = 7.07 Hz, 2 H) 3.25-3.49 (m, 6 H) 3.62 (s, 6 H) 3.64-3.73 (m, 1 H) 3.84-3.95 (m, 3 H) 4.09 (d, J = 9.17 Hz, 1 H) 7.08-7.17 (m, 5 H) 7.21-7.31 (m, 3 H). ESI m/z = 521 (M + NH₄). |
| 17 | 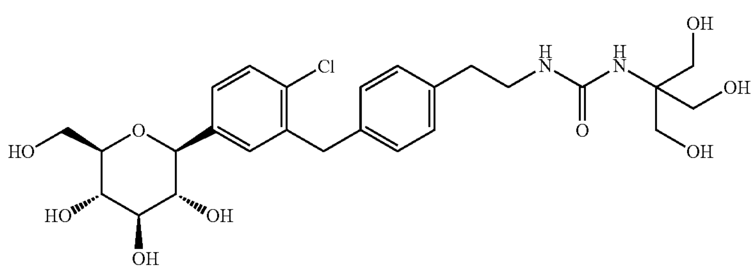 | 1H NMR (300 MHz) δ ppm 2.71 (t, J = 7.07 Hz, 2 H) 3.21-3.48 (m, 6 H) 3.61 (s, 6 H) 3.64-3.73 (m, J = 11.97, 5.13 Hz, 1 H) 3.83-3.91 (m, 1 H) 3.99-4.14 (m, 3 H) 7.12 (s, 4 H) 7.24-7.38 (m, 3 H). ESI m/z = 555 (M + H), 577 (M + Na). |
| 18 | 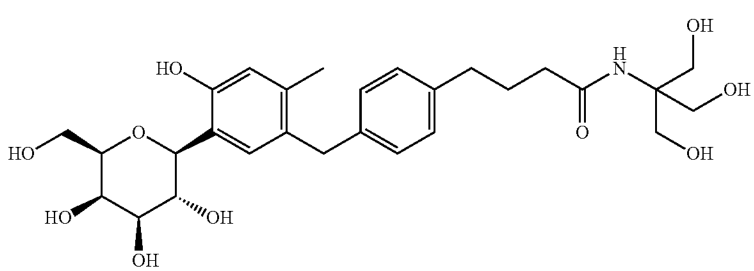 | 1H NMR (600 MHz) δ ppm 1.85-1.95 (m, 2 H) 2.10 (s, 3 H) 2.38 (t, J = 7.34 Hz, 2 H) 2.60 (t, J = 7.34 Hz, 2 H) 3.56-3.61 (m, 6 H) 3.61-3.68 (m, 1 H) 3.68-3.74 (m, 1 H) 3.74-3.80 (m, 1 H) 3.85-3.91 (m, 2 H) 3.96 (d, J = 3.21 Hz, 1 H) 4.14 (s, 2 H) 4.42 (d, J = 9.63 Hz, 1 H) 6.63 (s, 1 H) 7.00-7.09 (m, 4 H) 7.13-7.20 (m, 1 H). ESI m/z = 550 (M + H), 548 (M − H). |

TABLE 1-continued

| Compound No | structure | NMR (solvent, methanol-d₄), MS |
|---|---|---|
| 19 | 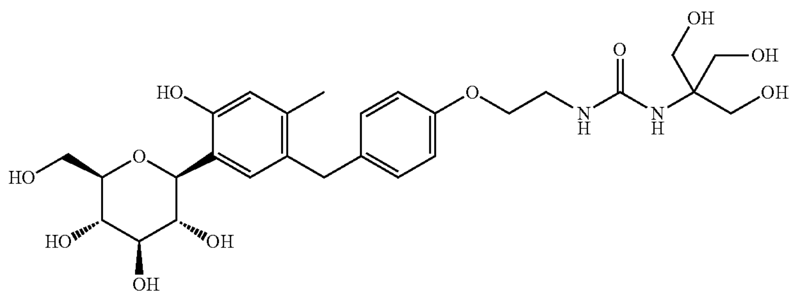 | 1H NMR (300 MHz) δ ppm 2.09 (s, 3 H) 3.37-3.51 (m, 6 H) 3.52-3.60 (m, 1 H) 3.65 (s, 6 H) 3.68-3.76 (m, 1 H) 3.80-3.91 (m, 3 H) 3.95 (t, J = 5.13 Hz, 2 H) 4.51 (d, J = 9.33 Hz, 1 H) 6.63 (s, 1 H) 6.80 (d, J = 8.24 Hz, 2 H) 7.01 (d, J = 8.24 Hz, 2 H) 7.10 (s, 1 H) |
| 20 | 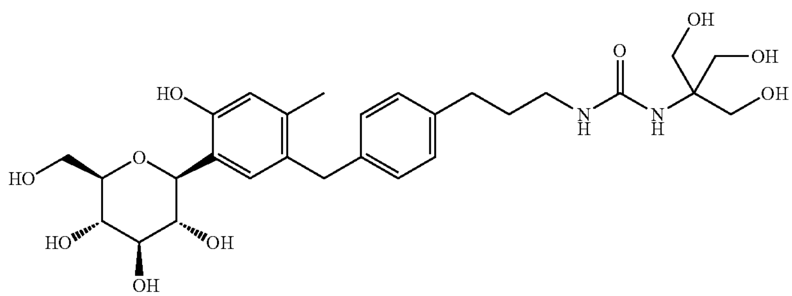 | 1H NMR (300 MHz) δ ppm 2.08 (s, 3 H) 3.38-3.61 (m, 4 H) 3.65 (s, 6 H) 3.67-3.73 (m, 1 H) 3.81-3.94 (m, 3 H) 4.22 (s, 2 H) 4.51 (d, J = 9.48 Hz, 1 H) 6.63 (s, 1 H) 7.03-7.09 (m, 2 H) 7.11-7.19 (m, 3 H). ESI m/z = 537 (M + H). |
| 21 | 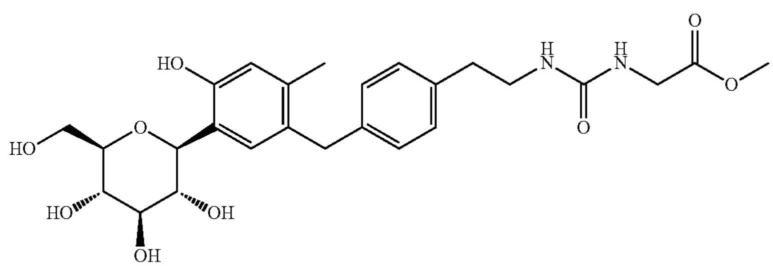 | 1H NMR (300 MHz) δ ppm 2.10 (s, 3 H) 2.72 (t, J = 7.07 Hz, 2 H) 3.29-3.37 (m, 2 H) 3.38-3.46 (m, 3 H) 3.49 (t, 1 H) 3.56 (t, J = 8.32 Hz, 1 H) 3.70 (s, 3 H) 3.81-3.91 (m, 5 H) 4.51 (d, J = 9.64 Hz, 1 H) 6.63 (s, 1 H) 7.00-7.15 (s, 1 H) 7.00-7.15 (m, 5 H). ESI m/z = 541 (M + Na). |
| 22 | 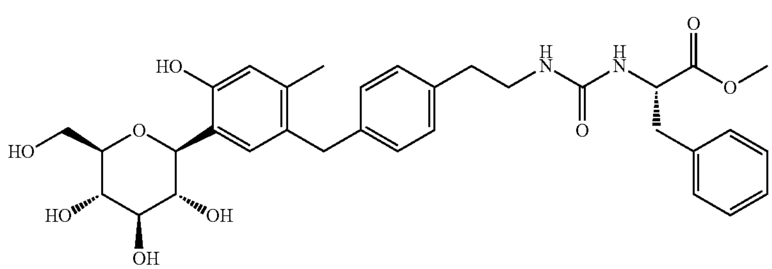 | 1H NMR (300 MHz) δ ppm 2.09 (s, 3 H) 2.66 (t, J = 7.31 Hz, 2 H) 2.93 (dd, 1 H) 3.06 (dd, 1 H) 3.21-3.28 (m, 2 H) 3.39-3.45 (m, 2 H) 3.47 (t, 1 H) 3.57 (t, J = 8.86 Hz, 1 H) 3.62-3.75 (m, 4 H) 3.87 (t, J = 5.44 Hz, 3 H) 4.47-4.59 (m, 2 H) 6.63 (s, 1 H) 6.98-7.08 (m, 4 H) 7.10-7.19 (m, 3 H) 7.18-7.30 (m, 3 H). ESI m/z = 631 (M + Na). |
| 23 | 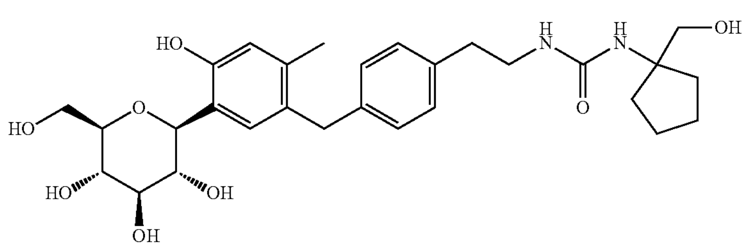 | 1H NMR (600 MHz) δ ppm 1.54-1.77 (m, 8 H) 2.07 (s, 3 H) 2.67 (t, J = 7.11 Hz, 2 H) 3.24-3.27 (m, 2 H) 3.36-3.42 (m, 2 H) 3.46 (t, J = 8.71 Hz, 1 H) 3.53 (d, J = 9.63 Hz, 1 H) 3.56 (s, 2 H) 3.68 (dd, J = 11.92, 5.50 Hz, 1 H) 3.81-3.87 (m, 3 H) 4.50 (d, J = 9.63 Hz, 1 H) 6.61 (s, 1 H) 7.02 (d, 2 H) 7.06 (d, 2 H) 7.10 (s, 1 H). ESI m/z = 567 (M + Na). 543 (M − H). |

TABLE 1-continued

| Compound No | structure | NMR (solvent, methanol-d₄), MS |
|---|---|---|
| 24 | 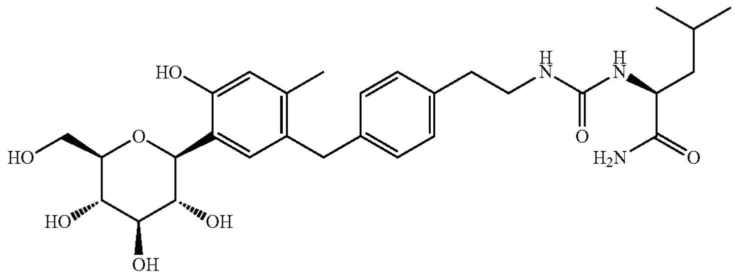 | 1H NMR (600 MHz, METHANOL-d$_3$) δ ppm 0.87-0.96 (m, 6 H) 1.40-1.55 (m, 2 H) 1.61-1.70 (m, 1 H) 2.08 (s, 3 H) 2.69 (t, J = 7.11 Hz, 2 H) 3.30-3.34 (m, 2 H) 3.35-3.42 (m, 2 H) 3.46 (t, J = 8.25 Hz, 1 H) 3.54 (t, J = 9.17 Hz, 1 H) 3.68 (dd, J = 11.92, 5.04 Hz, 1 H) 3.80-3.87 (m, 3 H) 4.18 (dd, J = 10.32, 4.81 Hz, 1 H) 4.50 (d, J = 9.63 Hz, 1 H) 6.61 (s, 1 H) 6.97-7.11 (m, 5 H). ESI m/z = 582 (M + Na). 558 (M − H). |
| 25 | 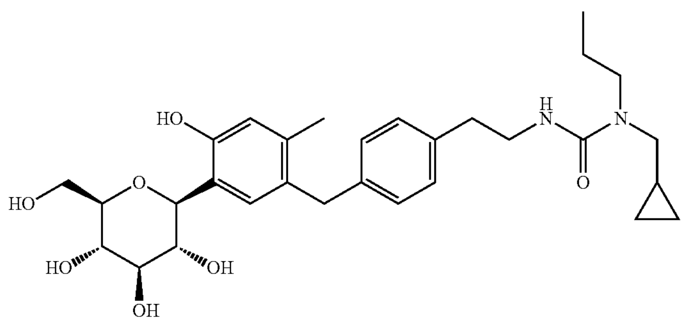 | 1H NMR (600 MHz, METHANOL-d$_3$) δ ppm 0.16 (q, 2 H) 0.44 (q, J = 5.96 Hz, 2 H) 0.83 (t, J = 7.34 Hz, 3 H) 0.86-0.96 (m, 1 H) 1.45-1.54 (m, 2 H) 2.06 (s, 3 H) 2.72 (t, J = 7.34 Hz, 2 H) 3.08 (d, J = 6.42 Hz, 2 H) 3.17 (t, 2 H) 3.32 (m, 2 H) 3.36-3.43 (m, 2 H) 3.46 (t, J = 8.71 Hz, 1 H) 3.54 (t, 1 H) 3.69 (dd, J = 11.92, 5.04 Hz, 1 H) 3.81-3.87 (m, 3 H) 4.50 (d, J = 9.63 Hz, 1 H) 6.60 (s, 1 H) 7.01 (d, J = 8.25 Hz, 2 H) 7.06 (d, 2 H) 7.11 (s, 1 H). ESI m/z = 565 (M + Na). 541 (M − H). |
| 26 | 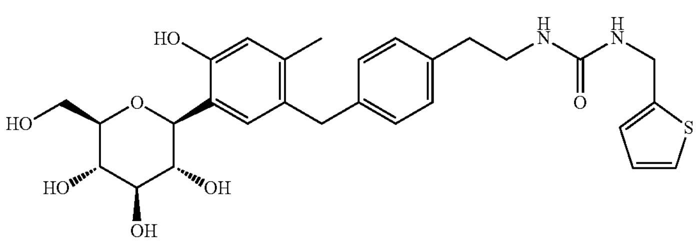 | 1H NMR (600 MHz) δ ppm 2.07 (s, 3 H) 2.69 (t, J = 7.11 Hz, 2 H) 3.29-3.33 (m, 2 H) 3.36-3.42 (m, 2 H) 3.46 (t, J = 8.71 Hz, 1 H) 3.54 (t, J = 9.40 Hz, 1 H) 3.68 (dd, J = 11.92, 5.50 Hz, 1 H) 3.81-3.87 (m, 3 H) 4.42 (s, 2 H) 4.49 (d, J = 9.63 Hz, 1 H) 6.61 (s, 1 H) 6.87-6.91 (m, 2 H) 7.01 (d, 2 H) 7.05 (d, 2 H) 7.10 (s, 1 H) 7.22 (dd, J = 4.36, 2.06 Hz, 1 H). ESI m/z = 565 (M + Na). 541 (M − H). |
| 27 | 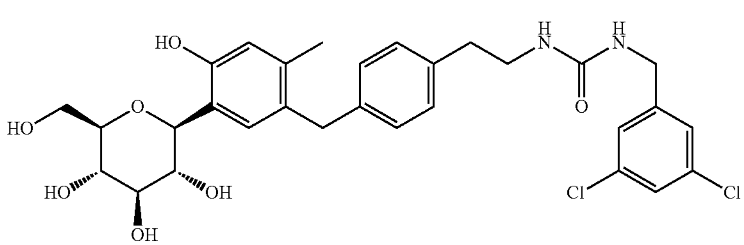 | 1H NMR (600 MHz) δ ppm 2.07 (s, 3 H) 2.70 (t, J = 6.88 Hz, 2 H) 3.30-3.34 (m, 2 H) 3.36-3.42 (m, 2 H) 3.46 (t, J = 8.71 Hz, 1 H) 3.53 (t, 1 H) 3.68 (dd, J = 11.92, 5.04 Hz, 1 H) 3.81-3.88 (m, 3 H) 4.23 (s, 2 H) 4.49 (d, J = 9.63 Hz, 1 H) 6.61 (s, 1 H) 7.02 (d, 2 H) 7.06 (d, 2 H) 7.10 (s, 1 H) 7.21 (d, 2 H) 7.27 (d, 1 H). ESI m/z = 605 (M + H). 603 (M − H). |

TABLE 1-continued

| Compound No | structure | NMR (solvent, methanol-d$_4$), MS |
|---|---|---|
| 28 | 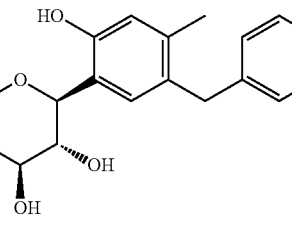 | 1H NMR (600 MHz) δ ppm 0.82-0.96 (m, 2 H) 1.13-1.30 (m, 3 H) 1.31-1.42 (m, 1 H) 1.60-1.77 (m, 5 H) 2.07 (s, 3 H) 2.68 (t, J = 7.11 Hz, 2 H) 2.89 (d, J = 6.88 Hz, 2 H) 3.23-3.32 (m, 2 H) 3.35-3.41 (m, 2 H) 3.46 (t, J = 8.71 Hz, 1 H) 3.54 (t, J = 9.17 Hz, 1 H) 3.68 (dd, J = 11.92, 5.04 Hz, 1 H) 3.80-3.87 (m, 3 H) 4.49 (d, J = 9.63 Hz, 1 H) 6.61 (s, 1 H) 7.01 (d, 2 H) 7.06 (d, 2 H) 7.10 (s, 1 H). ESI m/z = 543 (M + H). 541 (M − H). |
| 29 | 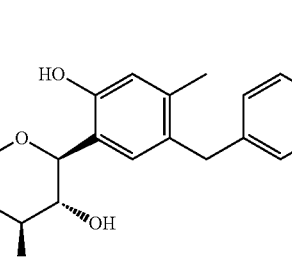 | 1H NMR (600 MHz) δ ppm 2.03-2.11 (m, 6 H) 2.52 (t, J = 6.88 Hz, 2 H) 2.69 (t, J = 7.11 Hz, 2 H) 3.24-3.27 (m, 2 H) 3.28-3.31 (m, 2 H) 3.35-3.42 (m, 2 H) 3.47 (t, 1 H) 3.53 (t, 1 H) 3.68 (dd, J = 11.92, 5.04 Hz, 1 H) 3.81-3.87 (m, 3 H) 4.50 (d, J = 9.63 Hz, 1 H) 6.61 (s, 1 H) 7.01 (d, 2 H) 7.06 (d, 2 H) 7.10 (s, 1 H). ESI m/z = 543 (M + Na). 519 (M − H). |
| 30 | 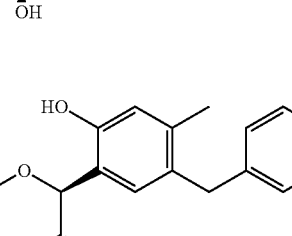 | 1H NMR (600 MHz) δ ppm 1.77 (ddd, J = 6.76, 3.32, 3.21 Hz, 4 H) 2.08 (s, 3 H) 2.51-2.57 (m, 6 H) 2.69 (t, J = 7.11 Hz, 2 H) 3.22 (t, J = 6.65 Hz, 2 H) 3.29-3.33 (m, 2 H) 3.35-3.42 (m, 2 H) 3.46 (t, J = 8.71 Hz, 1 H) 3.53 (t, J = 9.17 Hz, 1 H) 3.68 (dd, J = 12.15, 5.27 Hz, 1 H) 3.82-3.87 (m, 3 H) 4.49 (d, J = 9.63 Hz, 1 H) 6.61 (s, 1 H) 7.02 (d, 2 H) 7.06 (d, 2 H) 7.09 (s, 1 H). ESI m/z = 544 (M + H). 542 (M − H). |
| 31 | 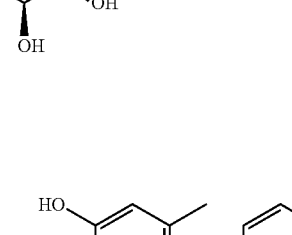 | 1H NMR (600 MHz) δ ppm 2.08 (s, 3 H) 2.68 (t, J = 7.11 Hz, 2 H) 3.23 (t, J = 5.50 Hz, 2 H) 3.24-3.33 (m, 5 H) 3.35-3.43 (m, 4 H) 3.46 (t, J = 8.71 Hz, 1 H) 3.54 (t, J = 9.17 Hz, 1 H) 3.68 (dd, 1 H) 3.80-3.88 (m, 3 H) 4.49 (d, J = 9.63 Hz, 1 H) 6.61 (s, 1 H) 7.02 (d, 2 H) 7.06 (d, 2 H) 7.10 (s, 1 H). ESI m/z = 527 (M + Na). 503 (M − H). |
| 32 | 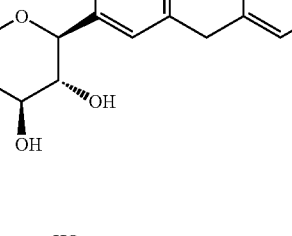 | 1H NMR (600 MHz) δ ppm 2.07 (s, 3 H) 2.45 (t, J = 6.42 Hz, 2 H) 2.67 (t, J = 7.11 Hz, 2 H) 3.21 (t, J = 6.88 Hz, 2 H) 3.30-3.35 (m, 2 H) 3.35-3.42 (m, 2 H) 3.46 (t, 1 H) 3.54 (dd, 1 H) 3.64 (s, 3 H) 3.68 (dd, J = 11.92, 5.04 Hz, 1 H) 3.80-3.90 (m, 3 H) 4.49 (d, J = 9.63 Hz, 1 H) 6.61 (s, 1 H) 7.01 (d, 2 H) 7.05 (d, 2 H) 7.10 (s, 1 H). ESI m/z = 555 (M + Na). 531 (M − H). |

TABLE 1-continued

| Compound No | structure | NMR (solvent, methanol-d₄), MS |
|---|---|---|
| 33 | 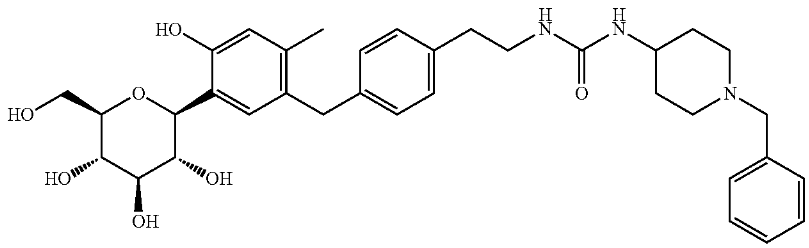 | 1H NMR (600 MHz) δ ppm 1.37-1.50 (m, 2 H) 1.80-1.89 (m, 2 H) 2.08 (s, 3 H) 2.31 (br. s., 2 H) 2.67 (t, J = 6.88 Hz, 2 H) 2.88 (br. s., 2 H) 3.25-3.34 (m, 2 H) 3.35-3.43 (m, 2 H) 3.43-3.52 (m, 2 H) 3.54 (t, 1 H) 3.59-3.71 (m, 3 H) 3.79-3.87 (m, 3 H) 4.49 (d, J = 9.63 Hz, 1 H) 6.61 (s, 1 H) 7.01 (d, 2 H) 7.05 (d, 2 H) 7.10 (s, 1 H) 7.25-7.37 (m, 5 H). ESI m/z = 620 (M + H). 618 (M − H). |
| 34 | 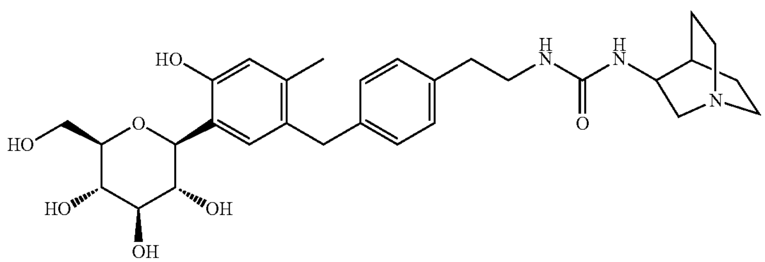 | 1H NMR (600 MHz) δ ppm 1.40-1.80 (m, 4 H) 2.08 (s, 3 H) 2.35-2.42 (m, 1 H) 2.66-2.82 (m, 5 H) 3.14-3.21 (m, 1 H) 3.29-3.35 (m, 4 H) 3.35-3.43 (m, 2 H) 3.46 (t, J = 8.94 Hz, 1 H) 3.53 (t, 1 H) 3.66-3.71 (m, 2 H) 3.81-3.88 (m, 3 H) 4.49 (d, J = 9.63 Hz, 1 H) 6.61 (s, 1 H) 7.02 (d, 2 H) 7.06 (d, 2 H) 7.11 (s, 1 H). ESI m/z = 556 (M + H). 554 (M − H). |
| 35 | 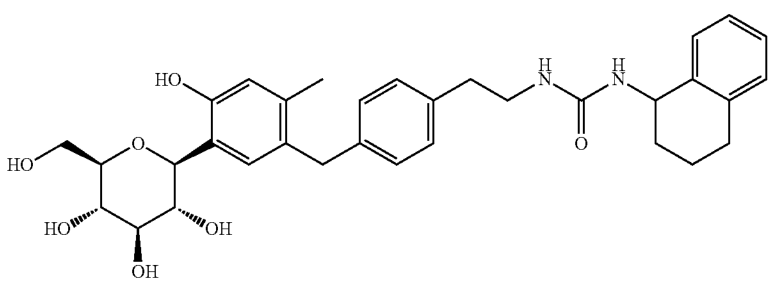 | 1H NMR (600 MHz) δ ppm 1.72 (m, 1 H) 1.73-1.80 (m, 1 H) 1.80-1.88 (m, 1 H) 1.90-1.97 (m, 1 H) 2.07 (s, 3 H) 2.65-2.81 (m, 4 H) 3.24-3.27 (m, 2 H) 3.31-3.42 (m, 3 H) 3.46 (t, J = 8.71 Hz, 1 H) 3.54 (t, J = 9.17 Hz, 1 H) 3.68 (dd, J = 11.92, 5.04 Hz, 1 H) 3.80-3.87 (m, 3 H) 4.49 (d, J = 9.63 Hz, 1 H) 6.60 (s, 1 H) 7.02 (d, J = 8.25 Hz, 3 H) 7.05-7.12 (m, 6 H). ESI m/z = 599 (M + Na). 575 (M − H). |
| 36 | 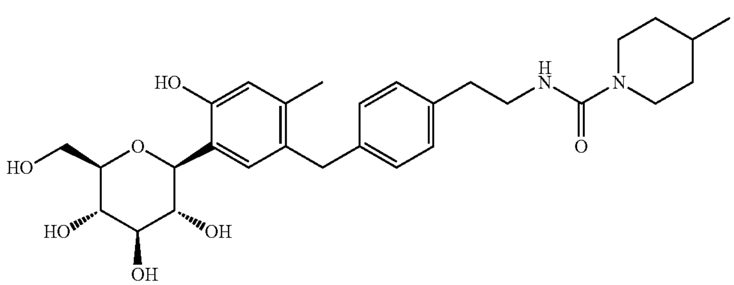 | 1H NMR (600 MHz) δ ppm 0.91 (d, J = 6.42 Hz, 3 H) 0.96-1.05 (m, 2 H) 1.47-1.56 (m, 1 H) 1.58 (d, J = 15.13 Hz, 2 H) 2.06 (s, 3 H) 2.65-2.73 (m, 4 H) 3.27-3.31 (m, 2 H) 3.35-3.43 (m, 2 H) 3.46 (t, J = 8.71 Hz, 1 H) 3.54 (t, J = 9.40 Hz, 1 H) 3.68 (dd, J = 11.92, 5.50 Hz, 1 H) 3.81-3.86 (m, 3 H) 3.89 (d, J = 12.84 Hz, 2 H) 4.50 (d, J = 9.63 Hz, 1 H) 6.60 (s, 1 H) 7.00 (d, 2 H) 7.05 (d, 2 H) 7.10 (s, 1 H). ESI m/z = 551 (M + Na). 527 (M − H). |

Example 11-1 (Another Preparation Method of the Compound of Example 11)

Preparation of (1S)-1,5-anhydro-1-[5-[4-[2-[[[2-hydroxy-1,1-bis(hydroxymethyl)ethyl]aminocarbonyl]amino]ethyl]benzyl]-2-hydroxy-4-methylphenyl]-D-glucitol

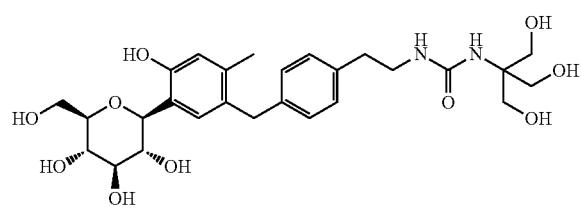

(1) Preparation of (1S)-1,5-anhydro-2,3,4,6-tetra-O-acetyl-1-[2-acetoxy-5-[4-[2-[[[2-hydroxy-1,1-bis(hydroxymethyl)ethyl]amino]carbonyl]amino]ethyl]benzyl]-4-methylphenyl]-D-glucitol To a chloroform solution (300 μL) of 1,1'-carbonyldiimidazole (7.30 mg, 0.045 mmol) were added a chloroform solution (150 μL) of (1S)-1-[5-[4-(2-aminoethyl)benzyl]-2-acetoxy-4-methylphenyl]-1,5-anhydro-2,3,4,6-tetra-O-acetyl-D-glucitol (18.4 mg, 0.030 mmol) and N-methyl morpholine (4.95 μL, 0.045 mmol), and the mixture was stirred for 30 minutes at room temperature. After that, to this reaction solution were added tris(hydroxymethyl)aminomethane (10.9 mg, 0.09 mmol) and N,N-dimethylformamide (150 μL), and this reaction mixture was stirred at 60° C. overnight. After the reaction mixture was cooled to room temperature, ethyl acetate was added thereto. And the mixture was washed with water, 1 M hydrochloric acid, and brine, and dried with anhydrous magnesium sulfate. The drying agent was filtered off, and the solvent was evaporated under reduced pressure. Thus obtained residue was purified with silica gel column chromatography (chloroform:methanol=95:5) to obtain the title compound (7.9 mg, 35%) as a colorless amorphous compound.

(2) Preparation of (1S)-1,5-anhydro-1-[5-[4-[2-[[[2-hydroxy-1,1-bis(hydroxymethyl)ethyl]aminocarbonyl]amino]ethyl]benzyl]-2-hydroxy-4-methylphenyl]-D-glucitol To a methanol solution (600 μL) of (1S)-1,5-anhydro-2,3,4,6-tetra-O-acetyl-1-[2-acetoxy-5-[4-[2-[[[[2-hydroxy-1,1-bis(hydroxymethyl)ethyl]amino]carbonyl]amino]ethyl]benzyl]-4-methylphenyl]-D-glucitol (7.9 mg, 0.0104 mmol) was added a 2.5 wt. % methanol solution of sodium methoxide (34 μL, 0.015 mmol), and the mixture was stirred for an hour at room temperature. The solvent was evaporated under reduced pressure. Thus obtained residue was purified with silica gel column chromatography (methanol) to obtain the title compound (3.0 mg, 52%) as a colorless amorphous compound.

Compounds 37 to 188 were synthesized by using corresponding amines in accordance with the method as with Example 11-1.

TABLE 2

| compound No. | X | formula | Exact MS | MS (M + H) or (M + Na) | MS (M − H) | ionization |
|---|---|---|---|---|---|---|
| 37 | X—NH₂ | C23H30N2O7 | 446.21 | 484 | 460 | ESI |
| 38 | X—NH—C(CH₂CH₃)(CH₂OH)₂ | C28H40N2O9 | 548.27 | 571 | 547 | ESI |
| 39 | X—NH—C(CH₃)₃ | C27H38N2O7 | 502.27 | 525 | 501 | ESI |
| 40 | X—NH—CH(CH₂Ph)—C(O)NH₂ | C32H39N3O8 | 593.27 | 616 | 592 | ESI |

TABLE 2-continued

| compound No. | [structure] | formula | Exact MS | MS (M + H) or (M + Na) | MS (M − H) | ionization |
|---|---|---|---|---|---|---|
| 41 | | C37H42N2O8 | 642.29 | 665 | 641 | ESI |
| 42 | | C28H34N2O8 | 526.23 | 527 | 525 | ESI |
| 43 | | C28H40N2O8 | 532.28 | 555 | 531 | ESI |
| 44 | | C29H43N3O7 | 545.31 | 546 | 544 | ESI |
| 45 | | C27H38N2O9 | 534.26 | 557 | 533 | ESI |
| 46 | | C29H42N2O8 | 546.29 | 569 | 545 | ESI |
| 47 | | C28H40N2O8S | 564.25 | 587 | 563 | ESI |
| 48 | | C32H40N2O8 | 580.28 | 603 | 579 | ESI |

TABLE 2-continued

| compound No. | formula | Exact MS | MS (M + H) or (M + Na) | MS (M − H) | ionization |
|---|---|---|---|---|---|
| 49 | C33H42N2O9S | 642.26 | 665 | 641 | ESI |
| 50 | C27H38N2O8 | 518.26 | 541 | 517 | ESI |
| 51 | C32H40N2O8 | 580.28 | 603 | 579 | ESI |
| 52 | C31H37FN2O7 | 568.26 | 591 | 567 | ESI |
| 53 | C37H42N2O7 | 626.3 | 649 | 625 | ESI |
| 54 | C30H42N2O9 | 574.29 | 597 | 573 | ESI |
| 55 | C33H42N2O9 | 610.29 | 633 | 609 | ESI |
| 56 | C26H36N2O7 | 488.25 | 511 | 487 | ESI |

TABLE 2-continued

| compound No. | [R group structure] | formula | Exact MS | MS (M + H) or (M + Na) | MS (M − H) | ionization |
|---|---|---|---|---|---|---|
| 57 | | C34H44N2O9 | 624.3 | 625 | 623 | ESI |
| 58 | | C27H39N3O7 | 517.28 | 518 | 516 | ESI |
| 59 | | C31H46N2O7 | 558.33 | 581 | 557 | ESI |
| 60 | | C32H39N3O8 | 593.27 | 616 | ND | ESI |
| 61 | | C32H36N2O7S | 592.22 | 615 | 591 | ESI |
| 62 | | C33H42N2O7 | 578.3 | 601 | 577 | ESI |
| 63 | | C31H38N2O8 | 566.26 | 589 | 565 | ESI |
| 64 | | C27H36N2O9 | 532.24 | 555 | 531 | ESI |
| 65 | | C28H38N2O8 | 530.26 | 553 | 529 | ESI |
| 66 | | C32H40N2O9 | 596.27 | 619 | 595 | ESI |

TABLE 2-continued

| compound No. | | formula | Exact MS | MS (M + H) or (M + Na) | MS (M − H) | ionization |
|---|---|---|---|---|---|---|
| 67 | X–NH–CH₂CH₂–N(piperidine) | C30H43N3O7 | 557.31 | 558 | 556 | ESI |
| 68 | X–NH–CH₂–Ph | C30H36N2O7 | 536.25 | 559 | 535 | ESI |
| 69 | X–NH–CH(Ph)–CH₂OH | C31H38N2O8 | 566.26 | 589 | 565 | ESI |
| 70 | X–NH–CH(CH₂OH)–CH(OH)–Ph | C32H40N2O9 | 596.27 | 619 | 595 | ESI |
| 71 | X–NH–CH₂CH₂–Ph | C31H38N2O7 | 550.27 | 551 | 549 | ESI |
| 72 | X–NH–(CH₂)₄–OH | C27H38N2O8 | 518.26 | 541 | 517 | ESI |
| 73 | X–NH–CH₂CH₂–N(Et)₂ | C29H43N3O7 | 545.31 | 546 | 544 | ESI |
| 74 | X–N(Bu)–CH₂CH₂OH | C29H42N2O8 | 546.29 | 569 | 545 | ESI |

TABLE 2-continued

[Structure: glycoside with phenolic ring bearing HO, methyl, benzyl-phenyl-CH2CH2-NH-C(=O)-X substituent]

| compound No. | formula | Exact MS | MS (M + H) or (M + Na) | MS (M − H) | ionization |
|---|---|---|---|---|---|
| 75 [X-NH-CH2-(2-phenyl)-S-(2-phenyl)-CH2OH] | C37H42N2O8S | 674.27 | 676 | 673 | APCI |
| 76 [X-NH-CH(CH3)-CH2OH] | C26H36N2O8 | 504.25 | 527 | 503 | ESI |
| 77 [X-NH-CH2-C(CH3)2-CH2OH] | C28H40N2O8 | 532.28 | 555 | 531 | ESI |
| 78 [X-NH-CH2CH2-S-CH2CH2-OH] | C27H38N2O8S | 550.23 | 573 | 549 | ESI |
| 79 [X-NH-CH2-CH(OH)-CH3] | C26H36N2O8 | 504.25 | 527 | 503 | ESI |
| 80 [X-NH-CH2-C(CH3)2-CH2-N(CH3)2] | C30H45N3O7 | 559.33 | 560 | 558 | ESI |
| 81 [X-NH-CH(CH2OH)2] | C26H36N2O9 | 520.24 | 543 | 519 | ESI |
| 82 [X-NH-CH2CH2CH2-OH] | C26H36N2O8 | 504.25 | 527 | 503 | ESI |
| 83 [X-N(pentyl)2] | C33H50N2O7 | 586.36 | 609 | 585 | ESI |
| 84 [X-NH-CH2-(4-(2-thienyl)phenyl)] | C34H38N2O7S | 618.24 | 641 | 617 | ESI |
| 85 [X-NH-CH2-CH(OH)-CH2-N(piperazine-N'-Boc)] | C35H52N4O10 | 688.37 | 689 | 687 | ESI |

TABLE 2-continued

| compound No. | (structure) | formula | Exact MS | MS (M + H) or (M + Na) | MS (M − H) | ionization |
|---|---|---|---|---|---|---|
| 86 | | C33H42N2O7 | 578.3 | 601 | 577 | ESI |
| 87 | | C32H46N2O8 | 586.33 | 587 | 585 | ESI |
| 88 | | C32H38N2O8 | 578.26 | 579 | 577 | ESI |
| 89 | | C36H47N3O8 | 649.34 | 672 | 648 | ESI |
| 90 | | C30H37N3O7 | 551.26 | 574 | 550 | ESI |
| 91 | | C32H40N2O7 | 564.28 | 565 | 563 | ESI |
| 92 | | C29H36N2O8 | 540.25 | 563 | 539 | ESI |
| 93 | | C29H35N3O7 | 537.25 | 560 | 536 | ESI |
| 94 | | C27H38N2O7 | 502.27 | 503 | 501 | ESI |
| 95 | | C28H41N3O7 | 531.29 | 532 | 530 | ESI |

TABLE 2-continued

| compound No. | formula | Exact MS | MS (M + H) or (M + Na) | MS (M − H) | ionization |
|---|---|---|---|---|---|
| 96 | C25H34N2O8 | 490.23 | 513 | 489 | ESI |
| 97 | C28H38N4O8 | 558.27 | 559 | 557 | ESI |
| 98 | C32H40N2O7 | 564.28 | 587 | 563 | ESI |
| 99 | C25H31F3N2O7 | 528.21 | 551 | 527 | ESI |
| 100 | C29H42N2O9 | 562.29 | 563 | 561 | ESI |
| 101 | C31H38N2O7 | 550.27 | 551 | 549 | ESI |
| 102 | C33H42N2O9 | 610.29 | 633 | 609 | ESI |
| 103 | C27H37N3O8 | 531.26 | 554 | 530 | ESI |
| 104 | C29H42N2O8 | 546.29 | 569 | 545 | ESI |
| 105 | C29H41N3O8 | 559.29 | 582 | 558 | ESI |
| 106 | C27H38N2O9 | 534.26 | 557 | 533 | ESI |

TABLE 2-continued

[Structure: HO-CH2-(tetrahydropyran with 3 OH groups)-attached to phenyl ring bearing OH, CH3, and CH2-phenyl-CH2CH2-NH-C(=O)-X]

| compound No. | [R group structure] | formula | Exact MS | MS (M + H) or (M + Na) | MS (M − H) | ionization |
|---|---|---|---|---|---|---|
| 107 | X-N(CH2CH2OEt)2 | C31H46N2O9 | 590.32 | 613 | 589 | ESI |
| 108 | X-NH-CH2-C(=O)-NH2 | C25H33N3O8 | 503.23 | 504 | 502 | ESI |
| 109 | X-NH-(CH2)3-N(2-pyrrolidinone) | C30H41N3O8 | 571.29 | 594 | 570 | ESI |
| 110 | X-NH-(CH2)3-N(imidazole) | C29H38N4O7 | 554.27 | 577 | 553 | ESI |
| 111 | X-N(CH3)-CH2CH2-OCH3 | C27H38N2O8 | 518.26 | 541 | 517 | ESI |
| 112 | X-N(Et)-CH2CH2-OH | C27H38N2O8 | 518.26 | 541 | 517 | ESI |
| 113 | X-N(CH3)-iPr | C27H38N2O7 | 502.27 | 525 | 501 | ESI |
| 114 | X-N(iPr)2 | C29H42N2O7 | 530.3 | 531 | 529 | ESI |
| 115 | X-N(CH3)-CH2CH2-(2-pyridyl) | C31H39N3O7 | 565.28 | 588 | 564 | ESI |
| 116 | X-NH-CH2CH2-(3,4-dihydroxyphenyl) | C31H38N2O9 | 582.26 | ND | 581 | ESI |

TABLE 2-continued

| compound No. | [structure] | formula | Exact MS | MS (M + H) or (M + Na) | MS (M − H) | ionization |
|---|---|---|---|---|---|---|
| 117 | | C27H38N2O9 | 534.26 | 557 | 533 | ESI |
| 118 | | C31H46N4O7 | 586.34 | 587 | ND | ESI |
| 119 | | C29H43N3O7 | 545.31 | 547 | 544 | ESI |
| 120 | | C26H34N2O9 | 518.23 | ND | 517 | ESI |
| 121 | | C30H37N3O7 | 551.26 | 574 | 550 | ESI |
| 122 | | C33H52N4O7 | 616.38 | 617 | 615 | ESI |
| 123 | | C33H44N2O7 | 580.31 | 581 | 579 | ESI |
| 124 | | C30H40N2O7 | 540.28 | 563 | 539 | ESI |
| 125 | | C28H38N2O7 | 514.27 | 537 | 513 | ESI |
| 126 | | C29H40N2O8 | 544.28 | 567 | 543 | ESI |

TABLE 2-continued

| compound No. | formula | Exact MS | MS (M + H) or (M + Na) | MS (M − H) | ionization |
|---|---|---|---|---|---|
| 127 | C29H40N2O8 | 544.28 | 567 | 543 | ESI |
| 128 | C31H44N2O7 | 556.31 | 579 | 555 | ESI |
| 129 | C30H42N2O7 | 542.3 | 565 | 541 | ESI |
| 130 | C31H44N2O8 | 572.31 | 595 | 571 | ESI |
| 131 | C35H50N2O7 | 610.36 | 633 | 609 | ESI |
| 132 | C34H43N3O7 | 605.31 | 606 | 604 | ESI |
| 133 | C31H43N3O9 | 601.3 | 624 | 600 | ESI |
| 134 | C35H45N3O7 | 619.33 | 620 | 618 | ESI |
| 135 | C27H34N2O9 | 530.23 | 553 | 529 | ESI |

TABLE 2-continued

| compound No. | | formula | Exact MS | MS (M + H) or (M + Na) | MS (M − H) | ionization |
|---|---|---|---|---|---|---|
| 136 | | C28H38N2O9S | 578.23 | 601 | 577 | ESI |
| 137 | | C36H40N2O8 | 628.28 | 651 | 627 | ESI |
| 138 | | C32H38N2O7 | 562.27 | 563 | 561 | ESI |
| 139 | | C36H38N2O8 | 626.26 | 649 | 625 | ESI |
| 140 | | C31H38N2O8 | 566.26 | 589 | 565 | ESI |
| 141 | | C31H38N2O10S | 630.22 | 653 | 629 | ESI |
| 142 | | C32H38N2O8 | 578.26 | 601 | 577 | ESI |
| 143 | | C32H44N2O7 | 568.31 | 591 | 567 | ESI |
| 144 | | C27H36N2O7S | 532.22 | 555 | 531 | ESI |

TABLE 2-continued

| compound No. | formula | Exact MS | MS (M+H) or (M+Na) | MS (M−H) | ionization |
|---|---|---|---|---|---|
| 145 | C28H38N2O7 | 514.27 | 537 | 513 | ESI |
| 146 | C34H49N3O7 | 611.36 | 613 | 610 | ESI |
| 147 | C32H45N3O7 | 583.33 | 585 | 582 | ESI |
| 148 | C32H44N2O7 | 568.31 | 591 | 567 | ESI |
| 149 | C31H46N4O7 | 586.34 | 587 | 585 | ESI |
| 150 | C32H48N4O7 | 600.35 | 601 | 599 | ESI |
| 151 | C29H40N2O8 | 544.28 | 567 | 543 | ESI |
| 152 | C33H41N3O8 | 607.29 | 630 | 606 | ESI |
| 153 | C32H39N3O9 | 609.27 | 632 | 608 | ESI |
| 154 | C35H45N3O7 | 619.33 | 642 | 618 | ESI |

TABLE 2-continued

[Structure: Glucopyranose-substituted phenol with methyl, methylene-phenyl-ethyl-NHC(=O)-X group]

| compound No. | [X group structure] | formula | Exact MS | MS (M + H) or (M + Na) | MS (M − H) | ionization |
|---|---|---|---|---|---|---|
| 155 | X—N(piperazine)N—ethyl | C29H41N3O7 | 543.29 | 566 | 542 | ESI |
| 156 | X—N(piperazine)N—CH2CH2OH | C29H41N3O8 | 559.29 | 560 | 558 | ESI |
| 157 | X—N(piperidine)-4-OH | C28H38N2O8 | 530.26 | 553 | 529 | ESI |
| 158 | X—N(piperidine)-4-CH2CH2OH | C30H42N2O8 | 558.29 | 581 | 557 | ESI |
| 159 | X—N (benz[de]isoquinoline) | C35H38N2O7 | 598.27 | 621 | 597 | ESI |
| 160 | X—N(piperidine)-4-N(morpholine) | C32H45N3O8 | 599.32 | 622 | 598 | ESI |
| 161 | X—N(piperazine)N—methyl | C28H39N3O7 | 529.28 | 552 | 528 | ESI |
| 162 | X—N(piperidine)-4-benzyl | C35H44N2O7 | 604.31 | 627 | 603 | ESI |
| 163 | X—N(isoindoline) | C31H36N2O7 | 548.25 | 571 | 547 | ESI |
| 164 | X—N(tetrahydro-β-carboline) | C34H39N3O7 | 601.28 | 624 | 600 | ESI |
| 165 | X—N(pyrrolidine) | C27H36N2O7 | 500.25 | 523 | 499 | ESI |
| 166 | X—N(morpholine) | C27H36N2O8 | 516.25 | 539 | 515 | ESI |

TABLE 2-continued

| compound No. | [structure] | formula | Exact MS | MS (M + H) or (M + Na) | MS (M − H) | ionization |
|---|---|---|---|---|---|---|
| 167 | | C28H37N3O8 | 543.26 | 566 | 542 | ESI |
| 168 | | C29H39N3O8 | 557.27 | 580 | 556 | ESI |
| 169 | | C31H42N2O9 | 586.29 | 609 | 585 | ESI |
| 170 | | C30H41N3O9 | 587.28 | 610 | 586 | ESI |
| 171 | | C33H46N4O8 | 626.33 | 649 | 625 | ESI |
| 172 | | C33H48N4O8 | 628.35 | 651 | 627 | ESI |
| 173 | | C33H41N3O7 | 591.29 | 614 | 590 | ESI |
| 174 | | C30H40N2O9 | 572.27 | 595 | 571 | ESI |
| 175 | | C32H45N3O9 | 615.32 | 638 | 614 | ESI |
| 176 | | C32H40N4O7 | 592.29 | 593 | 591 | ESI |
| 177 | | C29H39N3O8 | 557.27 | 580 | 556 | ESI |

TABLE 2-continued

| compound No. | formula | Exact MS | MS (M + H) or (M + Na) | MS (M − H) | ionization |
|---|---|---|---|---|---|
| 178 | C31H43N3O8 | 585.3 | 608 | 584 | ESI |
| 179 | C30H40N2O9 | 572.27 | 595 | 571 | ESI |
| 180 | C33H47N3O8 | 613.34 | 636 | 612 | ESI |
| 181 | C34H41FN2O7 | 608.29 | 631 | 607 | ESI |
| 182 | C35H44N2O8 | 620.31 | 643 | 619 | ESI |
| 183 | C32H43N3O9 | 613.3 | 636 | 612 | ESI |
| 184 | C30H38N2O10 | 586.25 | ND | 585 | ESI |
| 185 | C33H45N3O8 | 611.32 | 634 | 610 | ESI |
| 186 | C34H42N2O8 | 606.29 | 629 | 605 | ESI |

TABLE 2-continued

| compound No. | | formula | Exact MS | MS (M + H) or (M + Na) | MS (M – H) | ionization |
|---|---|---|---|---|---|---|
| 187 | | C31H41N3O8 | 583.29 | 606 | 582 | ESI |
| 188 | | C35H44N2O7 | 604.31 | 627 | 603 | ESI |

Furthermore, the compound (III) in which $R^B$ represents an an alkyl group substituted with an amino group can be synthesized by using ethylenediamine or N-methyl-1,3-propanediamine in accordance with the method as with Example 11-1.

Example 19

Preparation of (1S)-1,5-anhydro-1-[5-[4-[2-[(4S)-4-(cyclohexylmethyl)-2,5-dioxo imidazolidine-1-yl] ethyl]benzyl]-2-hydroxy-4-methylphenyl]-D-glucitol

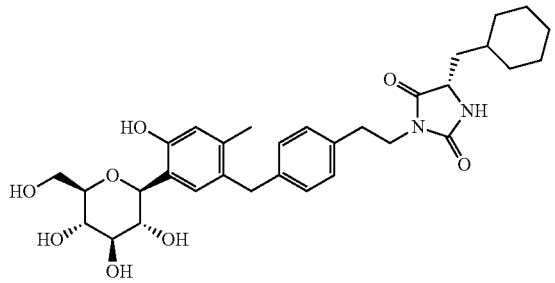

The title compound (5 mg, 29%) was obtained as a colorless oily compound according to the method as with Example 11-1 in which 3-cyclohexyl-L-alanine methyl ester hydrochloride was used instead of tris(hydroxymethyl)aminomethane.

1H NMR (600 MHz, METHANOL-$D_4$) δ ppm 0.81-1.00 (m, 2H) 1.31 (br. s., 3H) 1.38-1.47 (m, 1H) 1.48-1.55 (m, 1H) 1.56-1.78 (m, 4H) 2.05 (s, 3H) 2.83 (t, J=7.34 Hz, 2H) 3.28-3.33 (m, 2H) 3.35-3.43 (m, 2H) 3.46 (t, J=8.71 Hz, 1H) 3.54 (t, J=9.17 Hz, 1H) 3.57-3.71 (m, 3H) 3.81-3.88 (m, 3H) 3.96 (dd, J=9.40, 4.36 Hz, 1H) 4.50 (d, J=10.09 Hz, 1H) 6.60 (s, 1H) 7.00 (d, 2H) 7.04 (d, 2H) 7.08 (d, J=5.96 Hz, 1H).

ESI m/z=605(M+Na). 581(M−H).

Compounds 190 to 202 were synthesized by using corresponding amino acids in accordance with the method as with Example 19.

TABLE 3

| Compound No. | | formula | Exact MS | MS (M + H) or (M + Na) | MS (M – H) | ionization |
|---|---|---|---|---|---|---|
| 189 | | C32H42N2O8 | 582.29 | 605 | 581 | ESI |

TABLE 3-continued

| Compound No. | | formula | Exact MS | MS (M + H) or (M + Na) | MS (M − H) | ionization |
|---|---|---|---|---|---|---|
| 190 | | C32H36N2O8 | 576.25 | 599 | 575 | ESI |
| 191 | | C28H36N2O8 | 528.25 | 551 | 527 | ESI |
| 192 | | C28H36N2O8 | 528.25 | 551 | 527 | ESI |
| 193 | | C32H36N2O9 | 592.24 | 615 | 591 | ESI |
| 194 | | C31H34N2O7 | 546.24 | 569 | 545 | ESI |
| 195 | | C31H35N3O8 | 577.24 | 600 | 576 | ESI |

TABLE 3-continued

| Compound No. | | formula | Exact MS | MS (M + H) or (M + Na) | MS (M − H) | ionization |
|---|---|---|---|---|---|---|
| 196 | | C25H30N2O8 | 486.2 | 509 | 485 | ESI |
| 197 | | C27H34N2O9 | 530.23 | 553 | 529 | ESI |
| 198 | | C26H32N2O8 | 500.22 | 523 | 499 | ESI |
| 199 | | C29H36N2O10 | 572.24 | 595 | 571 | ESI |
| 200 | | C29H34N4O8 | 566.24 | 589 | 565 | ESI |
| 201 | | C36H40N4O8 | 656.28 | 679 | 655 | ESI |

TABLE 3-continued

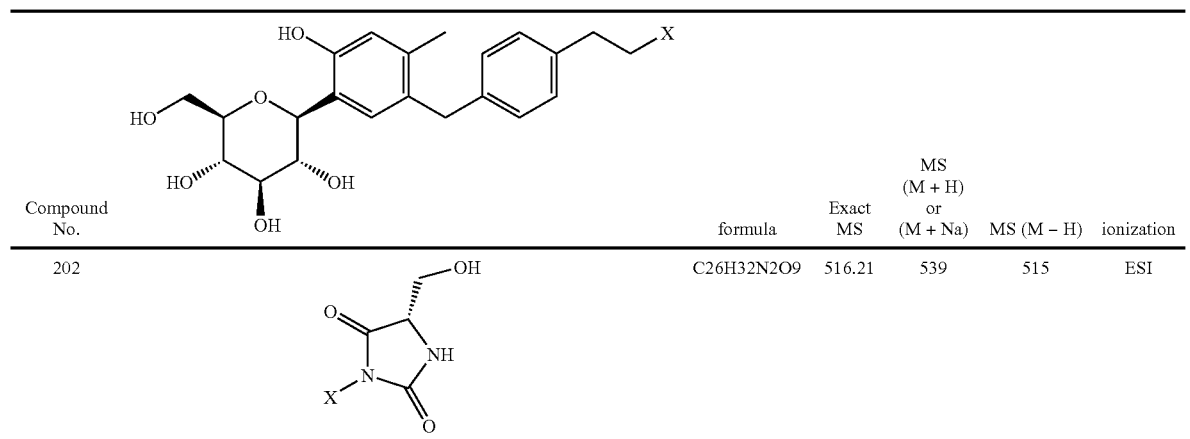

| Compound No. | formula | Exact MS | MS (M + H) or (M + Na) | MS (M − H) | ionization |
|---|---|---|---|---|---|
| 202 | C26H32N2O9 | 516.21 | 539 | 515 | ESI |

Formulation Example

TABLE 4

Formulation of tablet containing 100 mg of drug:

Content in single tablet:

| | |
|---|---|
| Drug | 108.35 mg |
| Lactose - monohydrate | 38.65 mg |
| Crystalline cellulose | 22.00 mg |
| Calcium carboxymethylcellulose | 20.00 mg |
| Hydroxypropylcellulose | 10.00 mg |
| Magnesium stearate | 1.00 mg |
| | 200.00 mg |

Preparation Method

The drug (the compound of the present invention) is mixed with lactose monohydrate, crystalline cellulose, calcium carboxymethylcellulose, and hydroxypropylcellulose. This mixture is pulverized with a pulverizer. The pulverized mixture is mixed with a mixer-granulator for 1 minute, and then granulated with water for 4 to 8 minutes. Thus obtained granulated products are dried at 70° C. for 40 minutes. The dry granulated powder is sifted with a 500 μm sieve. The sifted dry granulated powder and magnesium stearate are mixed with a V-type mixer at 30 rpm for 3 minutes. Thus obtained granule for making tablets is subjected to compression molding with a rotary tablet machine to make tablets.

TABLE 5

| | |
|---|---|
| Weight of Tablets: | 200 mg |
| Tablet size: | 8 mm, round |

Test Example 1

(1) Cloning of Human SGLT1 and SGLT2 and Introduction thereof into Expression Vector An SGLT1 sequence (NM_000343) was reverse-transcripted from human small intestinal mRNA, then amplified, and then introduced into pCMV-tag5A from Stratagene Corporation. An SGLT2 sequence (NM_003041) was prepared from human nephric mRNA as with the above method, and then introduced into pcDNA3.1+hygro from Invitrogen Corporation. Each cloned sequence was confirmed to be identical with the reported sequence.

(2) Preparation of CHO-k1 Cells Stably Expressing Human SGLT1 and Human SGLT2

The human SGLT1 and human SGLT2 expression vectors were transfected into CHO-k1 cells by using Lipofectamine 2000 from Invitrogen Corporation. The SGLT expression cells were incubated in the presence of Geneticin (SGLT1) or Hygromycin B (SGLT2) at a 500 μg/mL concentration to select resistant strains, and specific activity of sugar uptake was obtained as an indicator by the following system.

(3) Inhibition Test of Sodium-dependent Sugar Uptake in Cells

Cells stably expressing human SGLT1 and human SGLT2 were used for the inhibition test of sodium-dependent glucose uptake.

The cells were incubated in a pretreatment buffer A (200 μL for SGLT1, and 2 mL for SGLT2) for 20 minutes. The pretreatment buffer was removed and an uptake buffer B (75 μL for SGLT1, and 200 μL for SGLT2) containing a test compound was added to conduct an uptake reaction at 37° C. for 30 minutes (SGLT1) or an hour (SGLT2). After the reaction, the cells were washed with a washing buffer C twice (200 μL for SGLT1, and 2 mL for SGLT2), and then dissolved in a 0.2 M solution of NaOH (75 μL for SGLT1, and 400 μL for SGLT2). After a liquid scintilater was added thereto and mixed sufficiently, radioactivity was measured with micro-BETA (SGLT1) or a liquid scintillation counter from Beckman Coulter, Inc (SGLT2). As a control group, an uptake buffer containing no test compound was prepared. In addition, as the basic uptake buffer, an uptake buffer B containing choline chloride instead of NaCl was prepared.

A pretreatment buffer A: 140 mM choline chloride, 2 mM KCl, 1 mM $CaCl_2$, 1 mM $MgCl_2$, 10 mM HEPES/5 mM Tris, pH 7.4.

An uptake buffer B: 1 mM of methyl α-D-glucopyranoside containing [$^{14}$C]methyl α-D-glucopyranoside, 140 mM NaCl, 2 mM KCl, 1 mM $CaCl_2$, 1 mM $MgCl_2$, 10 mM HEPES/5 mM Tris, pH 7.4.

A washing buffer C: 10 mM methyl α-D-glucopyranoside, 140 mM choline chloride, 2 mM KCl, 1 mM $CaCl_2$, 1 mM $MgCl_2$, 10 mM HEPES/5 mM Tris, pH 7.4.

In order to obtain $IC_{50}$ values, test compounds having adequate 6 concentrations were used and the test compound concentrations ($IC_{50}$ values) at which sugar uptake is inhibited by 50% in comparison with the amount of sugar uptake (100%) of the control group were calculated. Test results are shown in Table 6.

TABLE 6

| compound No | SGLT1 (nM) | SGLT2 (nM) |
|---|---|---|
| 1 | 11 | 17 |
| 2 | 32 | 18 |
| 3 | 35 | 65 |
| 4 | 51 | 31 |
| 8 | 65 | 29 |
| 9 | 175 | 29 |
| 10 | 51 | 23 |
| 11 | 59 | 34 |
| 12 | 113 | 48 |
| 14 | 49 | 21 |
| 17 | 79 | 25 |
| 19 | 302 | 101 |
| 20 | 382 | 164 |
| 21 | 75 | 34 |
| 22 | 37 | 12 |
| 23 | 19 | 19 |
| 24 | 37 | 25 |
| 25 | 64 | 20 |
| 26 | 52 | 15 |
| 27 | 54 | 15 |
| 28 | 64 | 18 |
| 29 | 75 | 17 |
| 30 | 111 | 13 |
| 31 | 148 | 39 |
| 32 | 245 | 44 |
| 33 | 12 | 11 |
| 34 | 49 | 10 |
| 35 | 83 | 34 |
| 36 | 94 | 34 |

In addition, the sugar uptake inhibition rates at 100 nM concentration of the test compound in comparison with the control group are shown in Table 7.

TABLE 7

| compound No. | SGLT1 % inhibition at 100 nM | SGLT2 % inhibition at 100 nM |
|---|---|---|
| 38 | 89 | 83 |
| 39 | 80 | 83 |
| 40 | 79 | 89 |
| 41 | 78 | 86 |
| 42 | 78 | 87 |
| 43 | 77 | 86 |
| 45 | 75 | 80 |
| 46 | 74 | 91 |
| 47 | 73 | 89 |
| 48 | 73 | 87 |
| 49 | 73 | 81 |
| 50 | 71 | 77 |
| 51 | 71 | 84 |
| 52 | 71 | 84 |
| 53 | 70 | 74 |
| 54 | 79 | 73 |
| 55 | 69 | 69 |
| 56 | 68 | 77 |
| 57 | 68 | 51 |
| 59 | 67 | 86 |
| 60 | 66 | 91 |
| 61 | 65 | 95 |
| 62 | 65 | 79 |
| 63 | 63 | 81 |
| 64 | 62 | 76 |
| 65 | 62 | 76 |
| 66 | 62 | 83 |
| 67 | 61 | 82 |
| 68 | 60 | 83 |
| 69 | 60 | 83 |
| 70 | 59 | 83 |
| 71 | 59 | 86 |
| 123 | 78 | 87 |
| 124 | 71 | 79 |
| 125 | 68 | 90 |
| 132 | 90 | 90 |
| 137 | 71 | 79 |
| 138 | 65 | 84 |
| 143 | 66 | 80 |

Test Example 2

Confirmation Study of Inhibitory Effect on Elevation of Blood Glucose Level in Streptozotocin Diabetic Model Rats (1) Preparation of Diabetic Model Rats 7-week-old SD/IGS rats (from CHARLES RIVER LABORATORIES JAPAN, INC., male) were fasted for about 16 hours. Then to these rats under etherization were administered 50 mg/kg of streptozotocin (STZ) via the tail vein to prepare diabetic model rats. Similarly, to rats under etherization were administered 1 mL/kg physiological saline containing 1.25 mmol/L of citric acid via tail veins to prepare normal control rats. One week (8 weeks old) after administration of STZ or 1.25 mmol/L citric acid physiological saline, the rats were subjected to oral glucose tolerance test.

(2) Oral Glucose Tolerance Test

After the rats were fasted for about 16 hours, the medicament (1 mg/kg) suspended in a 0.5% carboxymethyl cellulose (CMC) aqueous solution was orally administered to a medicament treated group, and only a 0.5% aqueous solution of CMC was orally administered to a control group. At 5 minutes after the administration, a glucose solution (2 g/kg) was orally administered to each rat, and blood was collected at 5 points in total: before the administration (0 time), after 0.25, 0.5, 1 and 2 hours after the oral administration.

The blood was collected from the orbital sinus venosus of each rat under etherization with a heparin-coated blood collection tube and centrifuged, and then blood plasma was separated. The concentration of glucose in the blood plasma was determined with Glucose CII Test Wako from Wako Pure Chemical Industries, Ltd. As for the intensity of inhibitory effect on elevation of blood glucose level, area under the blood glucose level curve (AUC) was calculated by the trapezoidal rule based on the blood glucose levels of the medicament treated group from 0 time to 1 hour time. And a basal value is subtracted from AUC to describe the intensity as area under the blood glucose level increment (ΔAUC) and describe the intensity as a decrease rate from the ΔAUC of the control group. The results are shown in Table 8.

TABLE 8

| compound No | STZ rats-OGTT(2 g/kg) % inhibition ΔAUC0-1 h(mgh/dL) @1 mg/kg |
|---|---|
| 1 | 41.7 |
| 2 | 51.6 |
| 3 | 63.9 |
| 4 | 51.0 |

TABLE 8-continued

| compound No | STZ rats-OGTT(2 g/kg) % inhibition ΔAUC0-1 h(mgh/dL) @1 mg/kg |
|---|---|
| 8 | 45.1 |
| 11 | 69.3 |
| 9 | 50.1 |
| 10 | 67.8 |
| 12 | 48.8 |

By virtue of the present invention, it is expected to provide a preventive or therapeutic agent for diabetes comprising, as an active ingredient, a C-phenyl glycitol compound having not only a glucose absorption suppression action from the digestive tract but also a urine glucose excretion action by inhibiting a sodium dependent glucose cotransporter 1 (SGLT1) expressing on the epithelium of the small intestine and a sodium dependent glucose cotransporter 2 (SGLT2) expressing in the kidney.

The invention claimed is:

1. A C-phenyl glycitol compound represented by Formula (I) below or a pharmaceutically acceptable salt thereof,

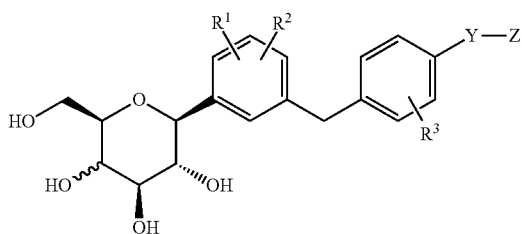

where
$R^1$ and $R^2$ are the same or different and represent a hydrogen atom, a hydroxyl group, a $C_{1-6}$ alkyl group, a $C_{1-6}$ alkoxy group or a halogen atom,
$R^3$ is a hydrogen atom, a $C_{1-6}$ alkyl group, a $C_{1-6}$ alkoxy group or a halogen atom,
Y is a $C_{1-6}$ alkylene group, —O—$(CH_2)n$- (n is an integer of 1 to 4) or a $C_{2-6}$ alkenylene group,
provided that when Z is —NHC(=NH)NH$_2$ or —NHCON($R^B$)$R^C$, n is not 1,
Z is —CONHR$^A$, —NHC(=NH)NH$_2$ or —NHCON($R^B$)$R^C$,

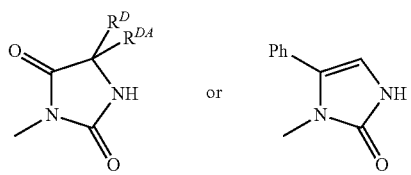

where
$R^A$ is
a $C_{1-6}$ alkyl group substituted with 1 to 3 substituents selected from the group consisting of a hydroxyl group, an amino group and a carbamoyl group,
$R^B$ is
(1) a hydrogen atom,
(2) a $C_{1-6}$ alkyl group that may be substituted with 1 to 3 substituents selected from Group A,
(3) a $C_{3-12}$ cycloalkyl group which may be substituted with 1 to 3 substituents selected from a hydroxyl group and a $C_{1-6}$ hydroxyalkyl group,
(4) a 3 to 12-membered heterocycloalkyl group or a 5 to 13-membered heteroaryl group that may be partially saturated, each of which contains one to three ring-constituting atom(s) selected from the group consisting of O, N, S, $SO_2$, CO and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group), and may be substituted with 1 to 3 substituents selected from the group consisting of a hydroxyl group and a $C_{1-6}$ hydroxyalkyl group, or
(5) a $C_{6-13}$ aryl group which may be partially saturated and may be substituted with 1 or 2 substituents selected from a hydroxyl group, and a $C_{1-6}$ alkyl group, a phenyl-$C_{1-6}$ alkyl group and a $C_{1-6}$ alkylsulfonyl group, each of which may be substituted with a hydroxyl group(s)
in which
Group A consists of
a halogen atom, a hydroxyl group, a $C_{1-6}$ alkoxy group which may be substituted with a hydroxyl group(s), a carboxyl group, a $C_{2-6}$ alkoxycarbonyl group, a carbamoyl group, an amino group, a $C_{1-6}$ alkylamino group, a di-$C_{1-6}$ alkylamino group, a $C_{2-6}$ acylamino group, a $C_{1-6}$ alkylthio group which may be substituted with a hydroxyl group(s),
a phenoxy group,
a phenyl group which may be substituted with 1 to 3 substituents selected from Group B (Group B consists of a hydroxyl group, a halogen atom, a $C_{1-6}$ alkoxy group, a $C_{1-6}$ alkyl group which may be substituted with a hydroxyl group(s), a $C_{1-6}$ alkylthio group, a thienyl group, a phenylthio group which may be substituted with a hydroxyl group(s) or a $C_{1-6}$ hydroxyalkyl group(s), and a piperidino group which may be substituted with a hydroxyl group(s) or a $C_{1-6}$ hydroxyalkyl group(s)),
a $C_{3-12}$ cycloalkyl group which may be substituted with 1 to 3 substituents selected from the group consisting of a hydroxyl group and a $C_{1-6}$ hydroxyalkyl group,
a 3 to 12-membered heterocycloalkyl group or a 5 to 13-membered heteroaryl group that may be partially saturated, each of which contains one to three ring-constituting atom(s) selected from the group consisting of O, N, S, $SO_2$, CO and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group), and may be substituted with 1 to 3 substituents selected from the group consisting of a hydroxyl group and a $C_{1-6}$ hydroxyalkyl group, and
—CONR$^{B1}$R$^{B2}$ wherein R$^{B1}$ and R$^{B2}$ together with the nitrogen atom to which they are attached form a 5 to 6 membered heterocycloalkyl group which may contain as another ring-constituting atom, an oxygen atom, a nitrogen atom or a sulfur atom and may be substituted with 1 or 2 substituents selected from the group consisting of a $C_{1-6}$ alkyl group which may be substituted with a hydroxyl group(s), a $C_{2-6}$ alkoxycarbonyl group and a phenyl$C_{1-6}$ alkyl group,
$R^C$ is
a hydrogen atom, a $C_{1-6}$ alkyl group which may be substituted with 1 or 2 substituents selected from the group consisting of a hydroxyl group, a di-$C_{1-6}$ alkylamino group, a $C_{2-6}$ alkoxycarbonyl group and a $C_{1-6}$ alkoxy group, or a $C_{3-12}$ cycloalkyl group which may be substituted with a hydroxyl group(s), and
$R^B$ and $R^C$ together with the nitrogen atom to which they are attached may form a 3 to 12 membered heterocycloalkyl group or a 5 to 13 membered heteroaryl group that may be partially saturated, each of which may contain 1 or 2 ring-constituting atom selected from O, N, $NR^{11}$, S, $SO_2$ and CO and which may be substituted with 1 or 2 substituents selected from the group consisting of a hydroxyl group, a $C_{2-6}$ alkoxycarbonyl group, a carbamoyl group, a $C_{2-6}$ acyl ($C_{1-6}$ alkyl)amino group, a di-$C_{1-6}$alkylaminocarbonyl group, a pyrrolidinyl group, a morpholino group, a pyrrolidin-1-yl-carbonyl group, a $C_{1-6}$ alkyl group that may be substituted with 1 to 3 substituents selected from the group consisting of a hydroxyl group, a pyrrolidin-1-yl group, a phenyl group and a $C_{2-6}$ alkoxycarbonyl group, and a phenyl group that may be substituted with 1 to 3 substituents selected from the group consisting of a $C_{1-6}$ alkyl group, a $C_{1-6}$ alkoxy group and a halogen atom where $R^{11}$ is a hydrogen atom, a $C_{2-6}$ acyl group, a phenyl group that may be substituted with a hydroxyl group(s), a pyridyl group, a furylcarbonyl group, an oxolanylcarbonyl group, a $C_{2-6}$ alkoxycarbonyl group or a $C_{1-6}$ alkyl group that may be substituted with 1 or 2 substituents selected from the group consisting of a hydroxyl group, a phenyl group, a di-$C_{1-6}$ alkylamino group, a morpholino group and a pyrrolidin-1-yl-carbonyl group, and $R^D$ is a hydrogen atom or a $C_{1-6}$ alkyl group which may be substituted with 1 or 2 substituents from the group consisting of a hydroxyl group, a $C_{3-12}$ cycloalkyl group, a phenyl group that may be substituted with a hydroxyl group(s), a pyridyl group, a $C_{2-6}$ alkoxycarbonyl group, an imidazolyl group and a 1-benzylimidazolyl group, and $R^{D4}$ is a hydrogen atom or a $C_{1-6}$ alkyl group.

2. The C-phenyl glycitol compound according to claim 1 which is a C-phenyl glucitol compound represented by Formula (II) below or a pharmaceutically acceptable salt thereof,

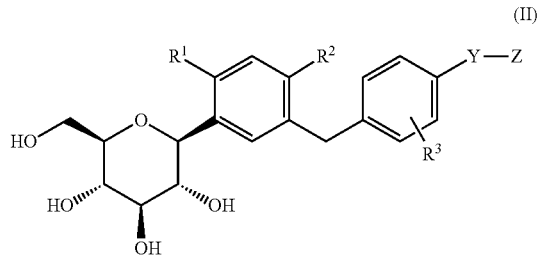

(II)

where $R^1$, $R^2$, $R^3$, Y and Z are the same as defined in claim 1.

3. The C-phenyl glycitol compound or a pharmaceutically acceptable salt thereof according to claim 2, wherein $R^1$ is a hydrogen atom, a hydroxyl group, a $C_{1-4}$ alkyl group or a $C_{1-4}$ alkoxy group, and $R^2$ is a $C_{1-4}$ alkyl group or a halogen atom.

4. The C-phenyl glycitol compound according to claim 2 or a pharmaceutically acceptable salt thereof where $R^3$ is a hydrogen atom.

5. The C-phenyl glycitol compound or a pharmaceutically acceptable salt thereof according to claim 3, wherein Y is a $C_{1-6}$ alkylene group or —O—$(CH_2)n$- (n is an integer of 2 to 4), and Z is —$NHCON(R^B)R^C$ wherein $R^B$ is
(1) a hydrogen atom,
(2) a $C_{1-6}$ alkyl group that may be substituted with 1 to 3 substituents selected from Group A,
(3) a $C_{3-12}$ cycloalkyl group which may be substituted with 1 to 3 substituents selected from a hydroxyl group and a $C_{1-6}$ hydroxyalkyl group, (4) a 3 to 12-membered heterocycloalkyl group or a 5 to 13-membered heteroaryl group that may be partially saturated, each of which contains one to three ring-constituting atom(s) selected from the group consisting of O, N, S, $SO_2$, CO and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group), and may be substituted with 1 to 3 substituents selected from the group consisting of a hydroxyl group and a $C_{1-6}$ hydroxyalkyl group, or
(5) a $C_{6-13}$ aryl group which may be partially saturated and may be substituted with 1 or 2 substituents selected from a hydroxyl group, and a $C_{1-6}$ alkyl group, a phenyl-$C_{1-6}$ alkyl group and a $C_{1-6}$ alkylsulfonyl group, each of which may be substituted with a hydroxyl group(s)

in which

Group A consists of a halogen atom, a hydroxyl group, a $C_{1-6}$ alkoxy group which may be substituted with a hydroxyl group(s), a carboxyl group, a $C_{2-6}$ alkoxycarbonyl group, a carbamoyl group, an amino group, a $C_{1-6}$ alkylamino group, a di-$C_{1-6}$ alkylamino group, a $C_{2-6}$ acylamino group, a $C_{1-6}$ alkylthio group which may be substituted with a hydroxyl group(s), a phenoxy group, a phenyl group which may be substituted with 1 to 3 substituents selected from Group B (Group B consists of a hydroxyl group, a halogen atom, a $C_{1-6}$ alkoxy group, a $C_{1-6}$ alkyl group which may be substituted with a hydroxyl group(s), a $C_{1-6}$ alkylthio group, a thienyl group, a phenylthio group which may be substituted with a hydroxyl group(s) or a $C_{1-6}$ hydroxyalkyl group(s), and a piperidino group which may be substituted with a hydroxyl group(s) or a $C_{1-6}$ hydroxyalkyl group(s)), a $C_{3-12}$ cycloalkyl group which may be substituted with 1 to 3 substituents selected from the group consisting of a hydroxyl group and a $C_{1-6}$ hydroxyalkyl group, a 3 to 12-membered heterocycloalkyl group or a 5 to 13-membered heteroaryl group that may be partially saturated, each of which contains one to three ring-constituting atom(s) selected from the group consisting of O, N, S, $SO_2$, CO and $NR^{10}$ ($R^{10}$ is a hydrogen atom, a $C_{1-6}$ alkyl group, a phenyl-$C_{1-6}$ alkyl group or a $C_{2-6}$ alkoxycarbonyl group), and may be substituted with 1 to 3 substituents selected from the group consisting of a hydroxyl group and a $C_{1-6}$ hydroxyalkyl group, and —$CONR^{B1}R^{B2}$ wherein $R^{B1}$ and $R^{B2}$ together with the nitrogen atom to which they are attached form a 5 to 6 membered heterocycloalkyl group which may contain as another ring-constituting atom, an oxygen atom, a nitrogen atom or a sulfur atom and may be substituted with 1 or 2 substituents selected from the group consisting of a $C_{1-6}$ alkyl group which may be substituted with a hydroxyl group(s), a $C_{2-6}$ alkoxycarbonyl group and a phenyl$C_{1-6}$ alkyl group, $R^C$ is a hydrogen atom, a $C_{1-6}$ alkyl group which may be substituted with 1 or 2 substituents selected from the group consisting of a hydroxyl group, a di-$C_{1-6}$ alkylamino group, a $C_{2-6}$ alkoxycarbonyl group and a $C_{1-6}$ alkoxy group, or a $C_{3-12}$ cycloalkyl group which may be substituted with a hydroxyl group(s), and $R^B$ and $R^C$ together with the nitrogen atom to which they are attached may form a 3 to 12 membered heterocycloalkyl group or a 5 to 13 membered heteroaryl group that may be partially saturated, each of which may contain 1 or 2 ring-constituting atom selected from O, N, NR$^{11}$, S, SO$_2$ and CO and which may be substituted with 1 or 2 substituents selected from the group consisting of a hydroxyl group, a C$_{2-6}$ alkoxycarbonyl group, a carbamoyl group, a C$_{2-6}$ acyl(C$_{1-6}$ alkyl)amino group, a di-C$_{1-6}$ alkylaminocarbonyl group, a pyrrolidinyl group, a morpholino group, a pyrrolidin-1-yl-carbonyl group, a C$_{1-6}$ alkyl group that may be substituted with 1 to 3 substituents selected from the group consisting of a hydroxyl group, a pyrrolidin-1-yl group, a phenyl group and a C$_{2-6}$ alkoxycarbonyl group, and a phenyl group that may be substituted with 1 to 3 substituents selected from the group consisting of a C$_{1-6}$ alkyl group, a C$_{1-6}$ alkoxy group and a halogen atom where R$^{11}$ is a hydrogen atom, a C$_{2-6}$ acyl group, a phenyl group that may be substituted with a hydroxyl group(s), a pyridyl group, a furylcarbonyl group, an oxolanylcarbonyl group, a C$_{2-6}$ alkoxycarbonyl group or a C$_{1-6}$ alkyl group that may be substituted with 1 or 2 substituents selected from the group consisting of a hydroxyl group, a phenyl group, a di-C$_{1-6}$ alkylamino group, a morpholino group and a pyrrolidin-1-yl-carbonyl group, and R$^D$ is a hydrogen atom or a C$_{1-6}$ alkyl group which may be substituted with 1 or 2 substituents from the group consisting of a hydroxyl group, a C$_{3-12}$ cycloalkyl group, a phenyl group that may be substituted with a hydroxyl group(s), a pyridyl group, a C$_{2-6}$ alkoxycarbonyl group, an imidazolyl group and a 1-benzylimidazolyl group, and R$^{DA}$ is a hydrogen atom or a C$_{1-6}$ alkyl group.

6. The C-phenyl glycitol compound or a pharmaceutically acceptable salt thereof according to claim 3, wherein Y is a C$_{1-6}$ alkylene group or —O—(CH$_2$)n- (n is an integer of 2 to 4), and Z is —NHCON(R$^B$)R$^C$, where R$^B$ is (1) a C$_{1-6}$ alkyl group which may be substituted with 1 to 3 substituents selected from Group A, (2) a C$_{3-12}$ cycloalkyl group which may be substituted with 1 to 3 substituents selected from a hydroxyl group and a C$_{1-6}$ hydroxyalkyl group, (3) a 3 to 12-membered heterocycloalkyl group or a 5 to 13-membered heteroaryl group that may be partially saturated, each of which contains one to three ring-constituting atom(s) selected from the group consisting of O, N, S and NR$^{10}$ (R$^{10}$ is a hydrogen atom, a C$_{1-6}$ alkyl group, a phenyl-C$_{1-6}$ alkyl group or a C$_{2-6}$ alkoxycarbonyl group) and may be substituted with 1 to 3 substituents selected from the group consisting of a hydroxyl group and a C$_{1-6}$ hydroxyalkyl group, or (4) a C$_{6-13}$ aryl group which may be partially saturated and may be substituted with 1 or 2 substituents selected from a hydroxyl group, and a C$_{1-6}$ alkyl group, a phenyl-C$_{1-6}$ alkyl group and a C$_{1-6}$ alkylsulfonyl group, each of which may be substituted with a hydroxyl group(s) in which Group A consists of a halogen atom, a hydroxyl group, a C$_{1-6}$ alkoxy group which may be substituted with a hydroxyl group(s), a C$_{2-6}$ alkoxycarbonyl group, a carbamoyl group, a di-C$_{1-6}$ alkylamino group, a C$_{1-6}$ alkylthio group which may be substituted with a hydroxyl group(s), a phenoxy group, a thienyl group, benzothienyl group, furyl group, a phenyl group which may be substituted with 1 to 3 substituents selected from the group consisting of a hydroxyl group, a halogen atom, a C$_{1-6}$ alkoxy group, a C$_{1-6}$ alkyl group which may be substituted with a hydroxyl group(s), a C$_{1-6}$ alkylthio group, a phenylthio group which may be substituted with a hydroxyl group(s) or a C$_{1-6}$ hydroxyalkyl group(s), and a piperidino group which may be substituted with a hydroxyl group(s) or a C$_{1-6}$ hydroxyalkyl group(s), a C$_{3-12}$ cycloalkyl group which may be substituted with 1 to 3 substituents selected from the group consisting of a hydroxyl group and a C$_{1-6}$ hydroxyalkyl group, a 3 to 12-membered heterocycloalkyl group which contains one to three ring-constituting atom(s) selected from the group consisting of O, N, S and NR$^{10}$ (R$^{10}$ is a hydrogen atom, a C$_{1-6}$ alkyl group, a phenyl-C$_{1-6}$ alkyl group or a C$_{2-6}$ alkoxycarbonyl group) and may be substituted with 1 to 3 substituents selected from the group consisting of a hydroxyl group and a C$_{1-6}$ hydroxyalkyl group, and 4-C$_{1-6}$ alkylpiperadine-1-ylcarbonyl group, R$^C$ is a hydrogen atom, and R$^B$ and R$^C$ together with the nitrogen atom to which they are attached may form a piperidine group which may be substituted with a pyrrolidinyl group or a C$_{1-6}$ alkyl group which is substituted with a diC$_{1-6}$alkylamino group or a pyrrolidin-1-yl group, or a thiomorpholine group or a decahydroisoquinoline group.

7. The C-phenyl glycitol compound or a pharmaceutically acceptable salt thereof according to claim 2, wherein Y is a C$_{1-6}$ alkylene group, Z is —CONHR$^A$, where R$^A$ is a C$_{1-6}$ alkyl group substituted with 1 to 3 substituents selected from the group consisting of a hydroxyl group and a carbamoyl group.

8. The C-phenyl glycitol compound or a pharmaceutically acceptable salt thereof according to claim 2, wherein Y is a C$_{1-6}$ alkylene group, and Z is —NHC(=NH)NH$_2$.

9. The C-phenyl glycitol compound or a pharmaceutically acceptable salt thereof according to claim 2, wherein Y is a C$_{1-6}$ alkylene group, and Z is

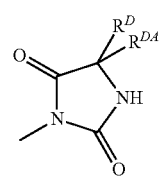

R$^D$ is a C$_{1-6}$ alkyl group which is substituted with a C$_{3-12}$ cycloalkyl group or a phenyl group and R$^{DA}$ is a hydrogen atom or a C$_{1-6}$ alkyl group.

10. The C-phenyl glycitol compound according to claim 1 which is a C-phenyl galacitol compound represented by Formula (III) below or a pharmaceutically acceptable salt thereof,

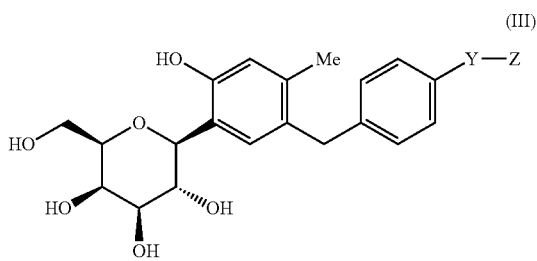

(III)

where
Y is
a $C_{1-6}$ alkylene group, and
Z is
—CONHR$^A$,
where
R$^A$ is a $C_{1-6}$ alkyl group substituted with 1 to 3 substituents selected from the group consisting of a hydroxyl group and a carbamoyl group.

11. The C-phenyl glycitol compound according to claim 1 which is a C-phenyl glucitol compound represented by Formula (IV) below or a pharmaceutically acceptable salt thereof,

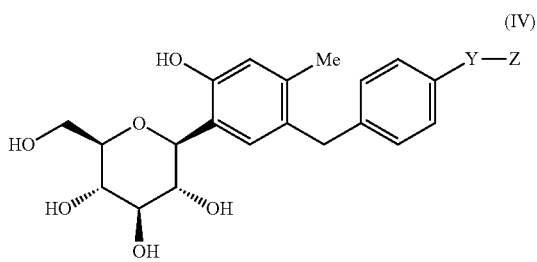

(IV)

where
Y is a $C_{1-6}$ alkylene group, and
Z is —CONHR$^{A1}$, —NHC(=NH)NH$_2$ or —NHCOR$^{B1}$,
where
R$^{A1}$ is a $C_{1-6}$ alkyl group substituted with 1 to 3 substituents selected from the group consisting of a hydroxyl group, an amino group and a carbamonyl group, and
R$^{B1}$ is
a $C_{1-6}$ alkylamino group which may be substituted with 1 to 3 hydroxyl groups or a 4-$C_{1-6}$ alkylpiperazin-1-yl-carbonyl group, or a 4-$C_{1-6}$ alkylpiperazin-1-yl group.

12. The C-phenyl glycitol compound according to claim 11 or a pharmaceutically acceptable salt thereof, wherein,
Y is a $C_{1-6}$ alkylene group,
Z is —CONHR$^{A1}$ or —NHC(=NH)NH$_2$, or

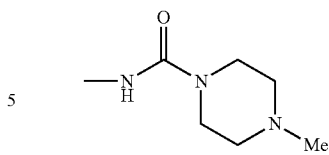

where
R$^{A1}$ is a $C_{1-6}$ alkyl group substituted with 1 to 3 substituents selected from the group consisting of a hydroxyl group, an amino group and a carbamonyl group.

13. The C-phenyl glycitol compound according to claim 11 or a pharmaceutically acceptable salt thereof, wherein
Y is a $C_{1-6}$ alkylene group, and
Z is —CONHR$^{A1}$
where R$^{A1}$ is a $C_{1-6}$ alkyl group substituted with 1 to 3 substituents selected from the group consisting of a hydroxyl group, an amino group and a carbamonyl group.

14. The C-phenyl glycitol compound according to claim 11 or a pharmaceutically acceptable salt thereof, wherein
Y is a $C_{1-6}$ alkylene group, and
Z is —NHC(=NH)NH$_2$.

15. The C-phenyl glycitol compound according to claim 11 or a pharmaceutically acceptable salt thereof, wherein
Y is a $C_{1-6}$ alkylene group, and
Z is —NHCOR$^{B1}$ (where R$^{B1}$ is a $C_{1-6}$ alkylamino group substituted with 1 to 3 hydroxyl groups or a 4-$C_{1-6}$ alkylpiperazin-1-yl-carbonyl group, or a 4-$C_{1-6}$ alkylpiperazin-1-yl group).

16. The C-phenyl glycitol compound according to claim 11 or a pharmaceutically acceptable salt thereof, wherein
Y is a $C_{1-6}$ alkylene group, and
Z is represented by

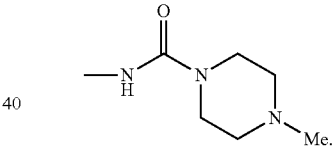

17. A pharmaceutical preparation, which comprises the C-phenyl glycitol compound according to claim 1 or a pharmaceutically acceptable salt thereof as an active ingredient, and a pharmaceutically acceptable carrier.

18. A method of inhibiting a sodium dependent glucose cotransporter 1 (SGLT1) activity and a sodium dependent glucose cotransporter 2 (SGLT2) activity which comprises applying the C-phenyl glycitol compound according to claim 1 or a pharmaceutically acceptable salt thereof to a subject in need thereof.

19. A method of treating diabetes which comprises applying the C-phenyl glycitol compound according to claim 1 or a pharmaceutically acceptable salt thereof to a subject in need thereof.

* * * * *